United States Patent
May et al.

(10) Patent No.: US 10,228,378 B2
(45) Date of Patent: Mar. 12, 2019

(54) DIAGNOSTIC AND THERAPEUTIC METHODS AND PRODUCTS RELATED TO ANXIETY DISORDERS

(71) Applicants: The University of Vermont and State Agricultural College, Burlington, VT (US); Emory University, Atlanta, GA (US)

(72) Inventors: Victor May, Essex, VT (US); Kerry J. Ressler, Atlanta, GA (US); Sayamwong E. Hammack, Essex Junction, VT (US); Donna Toufexis, So. Burlington, VT (US); Karen M. Braas, Essex, VT (US)

(73) Assignees: The University of Vermont and State Agricultural College, Burlington, VT (US); Emory University, Atlanta, GA (US)

( * ) Notice: Subject to any disclaimer, the term of this patent is extended or adjusted under 35 U.S.C. 154(b) by 0 days.

(21) Appl. No.: 15/614,448

(22) Filed: Jun. 5, 2017

(65) Prior Publication Data

US 2017/0343561 A1    Nov. 30, 2017

Related U.S. Application Data

(63) Continuation of application No. 13/983,114, filed as application No. PCT/US2012/023450 on Feb. 1, 2012, now Pat. No. 9,939,449.

(60) Provisional application No. 61/438,380, filed on Feb. 1, 2011.

(51) Int. Cl.
*G01N 33/68* (2006.01)
*C12Q 1/68* (2018.01)
*C12Q 1/6883* (2018.01)

(52) U.S. Cl.
CPC ....... *G01N 33/6893* (2013.01); *C12Q 1/6883* (2013.01); *C12Q 2600/112* (2013.01); *C12Q 2600/154* (2013.01); *C12Q 2600/156* (2013.01); *C12Q 2600/158* (2013.01); *G01N 2333/5757* (2013.01); *G01N 2800/301* (2013.01)

(58) Field of Classification Search
None
See application file for complete search history.

(56) References Cited

U.S. PATENT DOCUMENTS

| | | | |
|---|---|---|---|
| 5,486,472 | A | 1/1996 | Suzuki et al. |
| 6,911,430 | B2 | 6/2005 | Gandhi |
| 7,615,219 | B2 | 11/2009 | Freson et al. |
| 2004/0014095 | A1 | 1/2004 | Gerber et al. |
| 2005/0129687 | A1 | 6/2005 | Vizzard et al. |
| 2005/0209142 | A1* | 9/2005 | Bertilsson ............ A61K 31/675 514/8.3 |
| 2007/0149439 | A1 | 6/2007 | DiCicco-Bloom et al. |
| 2008/0070239 | A1 | 3/2008 | Wood |
| 2009/0305434 | A1 | 12/2009 | Fetissov et al. |
| 2010/0113379 | A1 | 5/2010 | Rubinsztein et al. |
| 2010/0129372 | A1 | 5/2010 | Freson et al. |
| 2015/0309050 | A1 | 10/2015 | May et al. |

OTHER PUBLICATIONS

Bangasser et al., Sex differences in corticotropin-releasing factor receptor signaling and trafficking: potential role in female vulnerability to stress-related psychopathology. Mol Psychiatry. Sep. 2010;15(9):877, 896-904. doi: 10.1038/mp.2010.66. Epub Jun. 15, 2010.

Beebe et al., Discovery and SAR of hydrazide antagonists of the pituitary adenylate cyclase-activating polypeptide (PACAP) receptor type 1 (PAC1-R). Bioorg Med Chem Lett. Mar. 15, 2008;18(6):2162-6. doi: 10.1016/j.bmcl.2008.01.052. Epub Jan. 18, 2008.

Binder et al., Association of FKBP5 polymorphisms and childhood abuse with risk of posttraumatic stress disorder symptoms in adults. JAMA. Mar. 19, 2008;299(11):1291-305. doi: 10.1001/jama.299.11.1291.

Bradley et al., Influence of child abuse on adult depression: moderation by the corticotropin-releasing hormone receptor gene. Arch Gen Psychiatry. Feb. 2008;65(2):190-200. doi: 10.1001/archgenpsychiatry.2007.26.

Cassell et al., Neuronal architecture in the rat central nucleus of the amygdala: a cytological, hodological, and immunocytochemical study. J Comp Neurol. Apr. 22, 1986;246(4):478-99.

Choi et al., Prelimbic cortical BDNF is required for memory of learned fear but not extinction or innate fear. Proc Natl Acad Sci U S A. Feb. 9, 2010;107(6):2675-80. doi: 10.1073/pnas.0909359107. Epub Jan. 25, 2010.

Dogrukol-AK et al., Passage of VIP/PACAP/secretin family across the blood-brain barrier: therapeutic effects. Curr Pharm Des. 2004;10(12):1325-40. Abstract.

Fahrenkrug et al., Pituitary adenylate cyclase activating polypeptide immunoreactivity in capsaicin-sensitive nerve fibres supplying the rat urinary tract. Neuroscience. Apr. 1998;83(4):1261-72.

Gillespie et al., Risk and resilience: genetic and environmental influences on development of the stress response. Depress Anxiety. 2009;26(11):984-92. doi: 10.1002/da.20605.

Girard et al., Noncompensation in peptide/receptor gene expression and distinct behavioral phenotypes in VIP- and PACAP-deficient mice. J Neurochem. Oct. 2006;99(2):499-513.

Green et al., Long-term administration of PACAP receptor antagonist, PACAP(6-27), impairs glucose tolerance and insulin sensitivity in obese diabetic ob/ob mice. Peptides. Sep. 2006;27(9):2343-9. Epub May 24, 2006.

Hammack et al., Roles for pituitary adenylate cyclase-activating peptide (PACAP) expression and signaling in the bed nucleus of the stria terminalis (BNST) in mediating the behavioral consequences of chronic stress. J Mol Neurosci. Nov. 2010;42(3):327-40. doi: 10.1007/s12031-010-9364-7. Epub Apr. 20, 2010.

(Continued)

*Primary Examiner* — Adam Weidner
(74) *Attorney, Agent, or Firm* — Wolf, Greenfield & Sacks, P.C.

(57) ABSTRACT

The present disclosure provides methods for diagnosing and treating anxiety disorders in female subjects. Diagnosis and treatment of such anxiety disorders are based, in part, on an analysis of pituitary adenylate cyclase-activating polypeptide (PACAP) expression levels in tissue collected from female subjects.

6 Claims, 25 Drawing Sheets

Specification includes a Sequence Listing.

(56) References Cited

OTHER PUBLICATIONS

Hammack et al., Chronic stress increases pituitary adenylate cyclase-activating peptide (PACAP) and brain-derived neurotrophic factor (BDNF) mRNA expression in the bed nucleus of the stria terminalis (BNST): roles for PACAP in anxiety-like behavior. Psychoneuroendocrinology. Jul. 2009;34(6):833-43. doi: 10.1016/j.psyneuen.2008.12.013. Epub Jan. 31, 2009.

Hashimoto et al., Pituitary adenylate cyclase-activating polypeptide is associated with schizophrenia. Mol Psychiatry. Nov. 2007;12(11):1026-32. Epub Mar. 27, 2007.

Maguschak et al., Beta-catenin is required for memory consolidation. Nat Neurosci. Nov. 2008;11(11):1319-26. doi: 10.1038/nn.2198. Epub Sep. 28, 2008.

Myers et al., A survey of genetic human cortical gene expression. Nat Genet. Dec. 2007;39(12):1494-9. Epub Nov. 4, 2007.

Ressler et al., Post-traumatic stress disorder is associated with PACAP and the PAC1 receptor. Nature. Feb. 24, 2011;470(7335):492-7. doi: 10.1038/nature09856.

Roman et al., PAC1 receptor antagonism in the bed nucleus of the stria terminalis (BNST) attenuates the endocrine and behavioral consequences of chronic stress. Psychoneuroendocrinology. Sep. 2014;47:151-65. doi: 10.1016/j.psyneuen.2014.05.014. Epub May 27, 2014.

Rothschild, Post-Traumatic Stress Disorder: Identification and Diagnosis. 1998. Accessed from www.healing-arts.org.

Shneider et al., Differential expression of PACAP receptors in postnatal rat brain. Neuropeptides. Dec. 2010;44(6):509-14. doi: 10.1016/j.npep.2010.09.001. Epub Oct. 23, 2010.

\* cited by examiner

| SNP | Chr7 position | Distance between SNPs (bp) | N (females) | p-value (females) | N (males) | p-value (males) |
|---|---|---|---|---|---|---|
| rs7784067 | 31084099 | | 502 | 0.834 | 297 | 0.291 |
| rs17159861 | 31085162 | 1063 | 491 | 0.457 | 293 | 0.176 |
| rs1981701 | 31089060 | 3898 | 496 | 0.729 | 290 | *0.021 |
| rs12670991 | 31089447 | 387 | 508 | 0.603 | 297 | 0.71 |
| rs12670977 | 31089583 | 136 | 503 | 0.525 | 299 | *0.014 |
| rs741051 | 31093792 | 4209 | 492 | 0.879 | 289 | *0.022 |
| rs10241138 | 31096363 | 2571 | 499 | 0.948 | 295 | 0.883 |
| rs17723231 | 31107448 | 11085 | 489 | 0.466 | 294 | 0.288 |
| rs10277350 | 31109768 | 2320 | 495 | 0.86 | 297 | 0.135 |
| rs10268647 | 31114877 | 5109 | 494 | 0.794 | 292 | 0.935 |
| rs2267727 | 31116266 | 1389 | 499 | 0.546 | 292 | 0.834 |
| rs7804302 | 31117646 | 1380 | 506 | 0.48 | 299 | 0.226 |
| rs7805043 | 31118094 | 448 | 498 | 0.995 | 300 | 0.483 |
| rs7804958 | 31118186 | 92 | 498 | 0.23 | 293 | 0.992 |
| rs10081254 | 31121671 | 3485 | 503 | 0.239 | 295 | 0.845 |
| rs1541516 | 31122542 | 871 | 494 | 0.858 | 287 | 0.941 |
| rs10269014 | 31128737 | 6195 | 498 | 0.228 | 296 | 0.701 |
| rs11979764 | 31131353 | 2616 | 507 | 0.508 | 297 | 0.565 |
| rs2267733 | 31134809 | 3456 | 505 | 0.11 | 295 | 0.76 |
| rs2267735 | 31135504 | 695 | 506 | **0.0002 | 297 | 0.763 |
| rs2267737 | 31136610 | 1106 | 508 | 0.557 | 298 | 0.669 |
| rs2267738 | 31136824 | 214 | 502 | 0.493 | 294 | 0.099 |
| rs2267740 | 31137003 | 179 | 499 | 0.52 | 295 | 0.864 |
| rs7786118 | 31139148 | 2145 | 508 | 0.63 | 297 | 0.918 |
| rs2041568 | 31141418 | 2270 | 502 | 0.149 | 294 | 0.611 |
| rs1541518 | 31148279 | 6861 | 507 | 0.064 | 297 | 0.974 |
| rs4503014 | 31149140 | 861 | 505 | 0.843 | 297 | 0.366 |

*p<.05, **p<.0005

Canonical ERE     cnaGGTCAnggTGaCCt
rs2267735     tcaGGTCAgagaGgaCg

| rs2267735 – PTSD | N (1237) | Wald $x^2$ | p-value |
|---|---|---|---|
| Male original | 295 | 0.036 | 0.85 |
| Male replication | 179 | 0.57 | 0.45 |
| Male combined | 474 | 0.123 | 0.73 |
| Female original | 503 | 13.7 | 0.00021 |
| Female replication | 260 | 4.8 | 0.029 |
| Female combined | 763 | 18.4 | 0.000018 |

SEQUENCE LISTING

<160> NUMBER OF SEQ ID NOS: 93

<210> SEQ ID NO 1
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 1

Phe Thr Asp Ser Tyr Ser Arg Tyr Arg Lys Gln Met Ala Val Lys Lys
1               5                   10                  15

Tyr Leu Ala Ala Val Leu Gly Lys Arg Tyr Lys Gln Arg Val Lys Asn
            20                  25                  30

Lys

<210> SEQ ID NO 2
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 2

Phe Thr Asp Ser Tyr Ser Arg Tyr Arg Lys Gln Met Ala Val Lys Lys
1               5                   10                  15

Tyr Leu Ala Ala Val Leu
            20

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 3

Tyr Lys Gln Arg Val Lys Asn Lys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Cys Tyr Lys Gln Arg Val Lys Asn Lys
1               5

<210> SEQ ID NO 5
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: variation
<222> LOCATION: (9)..(9)
<223> OTHER INFORMATION: g or c
<220> FEATURE:
<221> NAME/KEY: misc_feature
<222> LOCATION: (9)..(9)
<223> OTHER INFORMATION: n is a, c, g, or t

<400> SEQUENCE: 5
tcaggtcana gaggacg                                                17

<210> SEQ ID NO 6
<211> LENGTH: 17
<212> TYPE: DNA
<213> ORGANISM: Artificial Sequence
<220> FEATURE:
<223> OTHER INFORMATION: Synthetic Oligonucleotide

```
<220> FEATURE:
<221> NAME/KEY: variation
<222> LOCATION: (9)..(9)
<223> OTHER INFORMATION: c or g
<220> FEATURE:
<221> NAME/KEY: misc_feature
<222> LOCATION: (9)..(9)
<223> OTHER INFORMATION: n is a, c, g, or t

<400> SEQUENCE: 6
cgtcctctnt gacctga                                                    17

<210> SEQ ID NO 7
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 7
catgtgtagc ggagcaaggt t                                               21

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 8
gtcttgcagc gggtttcc                                                   18

<210> SEQ ID NO 9
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 9
tggatctcac cttccacctt ctg                                             23

<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 10
ccgataatct ccatcagttt cctg                                            24

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
ctgggacagg gccacccac                                                  19

<210> SEQ ID NO 12
<211> LENGTH: 19
<212> TYPE: DNA
<213> ORGANISM: Artificial Sequence
```

<220> FEATURE:
<223> OTHER INFORMATION: Synthetic Polynucleotide

<400> SEQUENCE: 12
ctatcacaag gacagaaaa                                              19

<210> SEQ ID NO 13
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 13
gtttgtcaag gccacagga                                              19

<210> SEQ ID NO 14
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 14
tacagtcaaa gtgagccag                                              19

<210> SEQ ID NO 15
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 15
atgggtcaga gtctcctgc                                              19

<210> SEQ ID NO 16
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 16
gccctagaag gtcaagtgc                                              19

<210> SEQ ID NO 17
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 17
tggggtcaga tggccagag                                              19

<210> SEQ ID NO 18
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 18
ggcttacaag gtcagagct                                              19

```
<210> SEQ ID NO 19
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 19
ctagcccaag gacacacag                                                     19

<210> SEQ ID NO 20
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 20
gaagatcaag gtcatctat                                                     19

<210> SEQ ID NO 21
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 21
cctggacaag gtggccata                                                     19

<210> SEQ ID NO 22
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 22
tatggccacc ttgtccagg                                                     19

<210> SEQ ID NO 23
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 23
acaggtaaag gtggcctag                                                     19

<210> SEQ ID NO 24
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 24
ctaggccacc tttacctgt                                                     19

<210> SEQ ID NO 25
<211> LENGTH: 19
<212> TYPE: DNA
<213> ORGANISM: Artificial Sequence
<220> FEATURE:
<223> OTHER INFORMATION: Synthetic Polynucleotide
```

```
<400> SEQUENCE: 25
cagggacaca cggaccccg                                                19

<210> SEQ ID NO 26
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 26
ggagggcaac ttgccctgg                                                19

<210> SEQ ID NO 27
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 27
ccagggcaag ttgccctcc                                                19

<210> SEQ ID NO 28
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 28
catcctgaag gtcaagcta                                                19

<210> SEQ ID NO 29
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 29
cctccccaag gtcagtgag                                                19

<210> SEQ ID NO 30
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 30
ccagccccag gtcaatgaa                                                19

<210> SEQ ID NO 31
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 31
ggaggtgaca atgagtttc                                                19
```

```
<210> SEQ ID NO 32
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 32
ggagggcaag gtcataaag                                                  19

<210> SEQ ID NO 33
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 33
caaggtcata aagggcggg                                                  19

<210> SEQ ID NO 34
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 34
atcctccaag gccaactca                                                  19

<210> SEQ ID NO 35
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 35
actcctccag gtcaggaga                                                  19

<210> SEQ ID NO 36
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 36
caaggtcatg ctgcagagt                                                  19

<210> SEQ ID NO 37
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 37
cttccccaag gtcatgctg                                                  19

<210> SEQ ID NO 38
<211> LENGTH: 19
<212> TYPE: DNA
<213> ORGANISM: Artificial Sequence
<220> FEATURE:
<223> OTHER INFORMATION: Synthetic Polynucleotide
```

```
<400> SEQUENCE: 38
actttccaag gtcacacaa                                                      19

<210> SEQ ID NO 39
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 39
ccagtgctag gtcacgcca                                                      19

<210> SEQ ID NO 40
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 40
gagggacaca aagacccct                                                      19

<210> SEQ ID NO 41
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 41
cgggggcaag accacctcc                                                      19

<210> SEQ ID NO 42
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 42
gcagggcatt gtgggctgg                                                      19

<210> SEQ ID NO 43
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 43
gtgggtgagg ctgtcctca                                                      19

<210> SEQ ID NO 44
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 44
tgaggacagc ctcacccac                                                      19
```

```
<210> SEQ ID NO 45
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 45
gtgaggcatc cagaccaca                                                    19

<210> SEQ ID NO 46
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 46
ggaggtcagg gtgtgaagg                                                    19

<210> SEQ ID NO 47
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 47
agggtgaaag gtcatacag                                                    19

<210> SEQ ID NO 48
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 48
tgacagcaag gtcaatgct                                                    19

<210> SEQ ID NO 49
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 49
ctggccaaag gtcagctga                                                    19

<210> SEQ ID NO 50
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 50
gtgtttcaag gacatcagc                                                    19

<210> SEQ ID NO 51
<211> LENGTH: 19
<212> TYPE: DNA
<213> ORGANISM: Artificial Sequence
<220> FEATURE:
<223> OTHER INFORMATION: Synthetic Polynucleotide
```

```
<400> SEQUENCE: 51
ataggccagt gtgatcagc                                                    19

<210> SEQ ID NO 52
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 52
cgaggtcaca gggccactt                                                    19

<210> SEQ ID NO 53
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 53
cactgccgag gtcacaggg                                                    19

<210> SEQ ID NO 54
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 54
cacggtcaac atgggctgc                                                    19

<210> SEQ ID NO 55
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 55
ctctttcaag gacatgatg                                                    19

<210> SEQ ID NO 56
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 56
ctgtgacatc atgtccttg                                                    19

<210> SEQ ID NO 57
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 57
gctggacacc cccaccttg                                                    19
```

<210> SEQ ID NO 58
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 58
tctcaccaag gtcaccagc                                            19

<210> SEQ ID NO 59
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 59
ttaggccacg ctggcctag                                            19

<210> SEQ ID NO 60
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 60
ctaggccagc gtggcctaa                                            19

<210> SEQ ID NO 61
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 61
aagcaccaag gacagggag                                            19

<210> SEQ ID NO 62
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 62
ccaggtcaca tggccacac                                            19

<210> SEQ ID NO 63
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 63
ctaaggccag gtcacatgg                                            19

<210> SEQ ID NO 64
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 64
gcatgtcagc tggaccttg                                           19

<210> SEQ ID NO 65
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 65
agtaggcaca agaccgcg                                            18

<210> SEQ ID NO 66
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 66
cgcggtcatt gtgcctact                                           19

<210> SEQ ID NO 67
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 67
tgtggccaag gccacctcc                                           19

<210> SEQ ID NO 68
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 68
gaagaggaag gtcaggtgg                                           19

<210> SEQ ID NO 69
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 69
actggtgata ctgactttt                                           19

<210> SEQ ID NO 70
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 70
tcatcccaag gacactcac                                           19

<210> SEQ ID NO 71
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 71
tcctgtcatt gtgccttgt                                                    19

<210> SEQ ID NO 72
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 72
ctgatgctag gtcaccta                                                     19

<210> SEQ ID NO 73
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 73
tcggggcagc tctacctct                                                    19

<210> SEQ ID NO 74
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 74
cagacacaag ggcagtgtc                                                    19

<210> SEQ ID NO 75
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 75
cagggtctcc ttgaccctg                                                    19

<210> SEQ ID NO 76
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 76
cagggtcaag gagaccctg                                                    19

<210> SEQ ID NO 77
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 77
tcaggtcaga gaggacgag                                            19

<210> SEQ ID NO 78
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 78
gtaggtcagg gttaactgg                                            19

<210> SEQ ID NO 79
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 79 tgggggccaag gagacccca                                           19

<210> SEQ ID NO 80
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 80
agatgtcaga atgtcttaa                                            19

<210> SEQ ID NO 81
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 81
gaaggtcaac ttgggtgtc                                            19

<210> SEQ ID NO 82
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 82
ggctgtgaag gtcaacttg                                            19

<210> SEQ ID NO 83
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 83
acagtccaag ggcaacacc                                            19

```
<210> SEQ ID NO 84
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 84
ctaggacacc tggaccatg                                                19

<210> SEQ ID NO 85
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 85
ggtggagaag gtcaagtca                                                19

<210> SEQ ID NO 86
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 86
ttaatccaag gccatttaa                                                19

<210> SEQ ID NO 87
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 87
catagtcagt ctcaccaga                                                19

<210> SEQ ID NO 88
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 88
ccccatccag gtcatggtg                                                19

<210> SEQ ID NO 89
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 89
ccaggtcatg gtgtatttc                                                19

<210> SEQ ID NO 90
<211> LENGTH: 19
<212> TYPE: DNA
<213> ORGANISM: Artificial Sequence
<220> FEATURE:
<223> OTHER INFORMATION: Synthetic Polynucleotide
```

```
<400> SEQUENCE: 90
caaggtcaag ggcataaaa                                                19

<210> SEQ ID NO 91
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 91
gtgagtcaag gtcaagggc                                                19

<210> SEQ ID NO 92
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 92
actggccaag gacacagag                                                19

<210> SEQ ID NO 93
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 93
cnaggtcang gtgacct                                                  17
```

DIAGNOSTIC AND THERAPEUTIC METHODS AND PRODUCTS RELATED TO ANXIETY DISORDERS

RELATED APPLICATIONS

This application is a continuation of U.S. application Ser. No. 13/983,114, filed Nov. 21, 2013, which is a national stage filing under U.S.C. § 371 of PCT International Application PCT/US2012/023450, filed Feb. 1, 2012. Application PCT/US2012/023450 claims priority under 35 U.S.C. § 119(e) to U.S. Provisional Application Ser. No. 61/438,380, entitled "DIAGNOSTIC AND THERAPEUTIC METHODS AND PRODUCTS RELATED TO ANXIETY DISORDERS" filed on Feb. 1, 2011. Each of the foregoing applications is herein incorporated by reference in its entirety.

FEDERALLY SPONSORED RESEARCH

This invention was made with government support under National Institutes of Health, Grant Nos. MH071537, NS37179, and HD27468. The government has certain rights in the invention

FIELD OF INVENTION

This invention relates to methods and products for the diagnosis, prognosis and therapy of anxiety disorders. The methods and products relate to pituitary adenylate cyclase activating polypeptide (PACAP) as well as PACAP inhibitors and PACAP receptor antagonists.

BACKGROUND OF INVENTION

The physiological and behavioral maladaptations to stress have long-term detrimental health consequences with an enormous burden to society. One behavioral manifestation of stress is anxiety-related disorders, which affect approximately 40 million American adults with an estimated annual cost greater than 47 billion dollars. In particular, severe stress and psychological trauma is a necessary component for the development of post-traumatic stress disorder (PTSD), an extreme maladaptive and debilitating psychiatric disorder affecting up to 40% of individuals over lifetime exposure to severe or traumatic stressors. Currently, there are no reliable biochemical or molecular diagnostic tools or targeted treatments for PTSD and other stress-related disorders. Further, current treatments are limited and have not yet been targeted based on the underlying pathophysiology.

SUMMARY OF INVENTION

The invention in some aspects relates to the discovery that PACAP (Adcyap1) and its cognate PAC1 receptor (Adcyap1r1) and/or VPAC receptors (Vipr1, Vipr2) are important mediators of abnormal stress responses that underlie anxiety disorders such as PTSD.

In some aspects, provided herein are methods for diagnosing an anxiety disorder in a female subject. The diagnostic methods may comprise: collecting a tissue sample from the subject; analyzing PACAP protein expression levels in the tissue sample; and diagnosing the anxiety disorder in the subject having elevated tissue PACAP expression levels as compared to a control tissue sample obtained from a subject who does not have an anxiety disorder.

In one aspect, the anxiety disorder is PTSD.

In another aspect, the female subject exhibits at least one endophenotype of PTSD. In yet another aspect, the at least one PTSD endophenotype may be intrusive re-experiencing, avoidance, hyperarousal, or fear discrimination.

In still another aspect, the PACAP expression levels in the tissue samples may reflect PACAP-38 peptide or PACAP-27 peptide expression levels, or both. In a further aspect, the PACAP expression levels reflect only PACAP38 peptide expression levels.

The analyzing of PACAP protein expression levels in the tissue sample may be by radioimmunoassay, or by another analytical assay known in the art.

In one aspect, the tissue sample may be from blood, serum, plasma, or cerebrospinal fluid (CSF). In another aspect, the tissue sample is blood.

In yet another aspect, the subject has been exposed to a trauma.

In some aspects, provided herein are methods for identifying a subject at risk of developing an anxiety disorder. These methods may comprise: collecting a DNA sample from the subject; analyzing the DNA sample for the presence of a SNP in a PAC1 receptor gene; and diagnosing the anxiety disorder in the subject having the SNP in the PAC1 receptor gene.

In one aspect, the anxiety disorder is PTSD.

In another aspect, the gene encoding the PAC1 receptor is ADCYAP1R1.

In yet another aspect, the SNP is located at position rs2267735 of the ADCYAP1R1 gene. The SNP may be a G→C allelic mutation.

In still another aspect, the subject may have been exposed to a trauma.

In other aspects, provided herein, are methods for identifying a subject at risk of developing an anxiety disorder. These methods may comprise: collecting a DNA sample from the subject; analyzing the DNA sample for epigenetic methylation at a first site within a ADCYAP1R1 CpG island; and diagnosing the anxiety disorder in the subject having elevated levels of epigenetic methylation. In one aspect, the anxiety disorder is PTSD.

In some aspects, provided herein, are methods of treating an anxiety disorder in a female subject in need thereof, which may comprise administering to the subject a therapeutically effective amount of a PACAP inhibitor. In one aspect, the anxiety disorder is PTSD.

In another aspect, the PACAP inhibitor is truncated PACAP peptide. The truncated PACAP peptide may be PACAP-38 or PACAP-27.

In yet another aspect, the PACAP inhibitor is a small molecule drug, small interfering RNA (siRNA), or an antibody. In other aspects, the PACAP inhibitor may be, but is not limited to, a deletion variant of maxadilan, an acyl hydride, a JNK/p38 inhibitor, a histone deactylase inhibitor, sodium butyrate, trichostatin A, or a BMP molecule. A deletion variant of maxadilan may be MaxD4 or M65.

Also provided herein, are DNA amplification kits for diagnosing an anxiety disorder in a female subject. Such kits may comprises: two or more oligonucleotide primers capable of binding to DNA sequence flanking position rs2267735 of the ADCYAP1R1 gene, optimization buffer, optionally polymerase, and optionally deoxyribonucleotide triphophates (dNTPs). Each element of the kit may be arranged in one or more containers.

Also provided are immunoassays kits for diagnosing an anxiety disorder in a female subject. These kits may comprise a primary IgG anti-PACAP antibody, an anti-IgG immuno-conjugated secondary antibody, optionally diluent and wash buffers, optionally chromagen, and one or more pre-coated microplate(s). Each element of the kit may be arranged in one or more containers.

According to aspects herein, gene chips or micro gene chips are provided. Those gene chips may comprise a solid surface, having attached thereto a plurality of oligonucleotides. The oligonucleotides may have a sequence complementary to a portion of a PAC1 receptor gene or a flanking sequence thereof. Portions of the PAC1 receptor gene may have a SNP. As used herein, gene chips may comprise a molecular array or microarray.

In some aspects, provided herein are gene chip kits for diagnosing an anxiety disorder in a female subject. These gene chip kits may comprise any one or more of the a gene chips or micro gene chips described herein, a hybridization buffer, optionally a stain solution; and optionally a wash buffer. Each element of the kit may be arranged in one or more containers.

In some aspects, provided herein are compositions comprising an 8 or 9 amino acid peptide of SEQ ID NO:3 or SEQ ID NO:4. In some embodiments, provided herein are antibodies that bind specifically to an epitope at the carboxy-terminal end of PACAP. In certain embodiments, the epitope is SEQ ID NO:3 or SEQ ID NO:4. In some embodiments, provided herein are compositions comprising an antibody that binds specifically to a peptide of SEQ ID NO:3 or SEQ ID NO:4.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The present invention may be more easily and completely understood when taken in conjunction with the accompanying figures.

DETAILED DESCRIPTION OF THE INVENTION

Figure 1A:
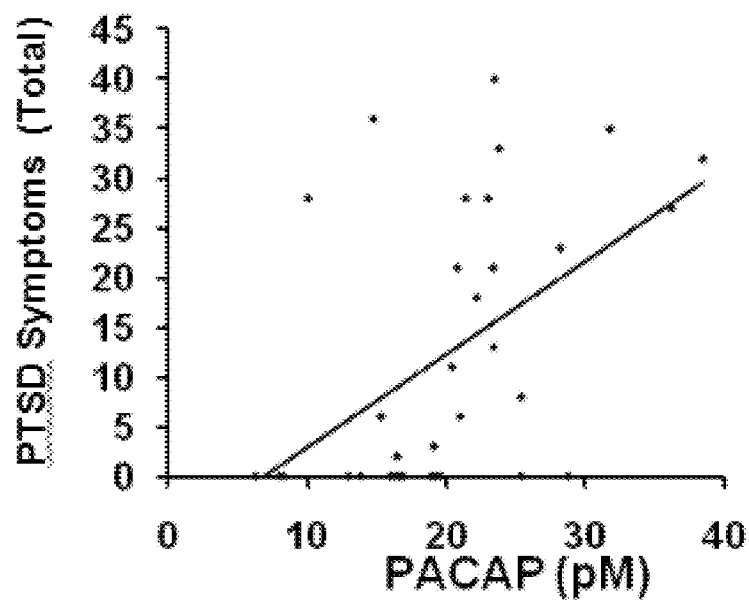
FIG. 1A shows PTSD symptom levels (y-axis, using the PTSD Symptom Scale, range 0-51), relative to Plasma PACAP38 blood levels (x-axis, pM). In females, continuous plasma PACAP38 varies with continuous PTSD symptoms (N=34; r=0.497, p<0.005).

It has been discovered according to the invention that pituitary adenylate cyclase activating polypeptide (PACAP, encoded by Adcyap1, e.g., NCBI Reference sequence NM_001099733.1) and PAC1 receptor (encoded by Adcyap1r1, e.g., NCBI Reference sequence NM_001199635) and/or VPAC receptors (VPAC1, encoded by Vipr1, e.g., NCBI Reference Sequence: NM_004624.3; VPAC2, encoded by Vipr2, e.g., NCBI Reference Sequence: NM_003382.4) play an important role in abnormal stress responses involved in anxiety disorders such as PTSD, particularly in female patients. For example, it was demonstrated experimentally (shown in the Examples presented herein) that 1) blood PACAP peptide levels are elevated in females with PTSD diagnosis; and 2) PTSD diagnosis in females is associated with a unique single nucleotide polymorphism (SNP) in the PAC1 receptor gene. In view of the discoveries described herein it may now be possible to diagnose anxiety disorders in female subjects using protein or DNA based assays. For instance, radioimmunoassays, enzyme linked immunosorbent assay (ELISA) or any related biochemical assays to measure PACAP peptide levels in blood or other tissues, may be used as a diagnostic tool to facilitate identification of anxiety disorder and PTSD; and 2) molecular array, polymerase chain reaction (PCR) or related genetic approaches used to examine the identified SNP for variants in the PAC1 receptor gene may be used as a means for the diagnosis of PTSD, and possibly other anxiety disorders.

The biochemical and molecular/genetic assays for PACAP and PAC1 receptor and/or VPAC receptors are envisioned to complement current clinical diagnostics for PTSD and anxiety-related disorders. The assays are also contemplated to be used as potential screens for people entering high stress occupations or environments. From the invention assays, identified individuals who fall within susceptibility criteria may be limited or restricted from severe stress situations to avert future development of PTSD or other anxiety-related disorder. One example of this utility may be in the armed services; the identification of individuals susceptible to chronic anxiety/PTSD would allow preventative or interventional measures to preclude repeated high stress combat exposures and the development of combat-related PTSD and anxiety.

Therapeutic methods related to these discoveries are also described herein. The invention in these aspects relates to methods of treating an anxiety disorder in a female subject by administering the female subject in need of such treatment a PACAP inhibitor or a PAC1 receptor antagonist and/or a VPAC receptor antagonist.

PACAP is a polypeptide hormone that stimulates adenylate cyclase in pituitary cells. Two forms of PACAP, PACAP-38 and PACAP-27 are known, and are thought to be equally potent in stimulating adenylate cyclase in pituitary cells. PACAP-38 contains 38 amino acid residues, whereas PACAP-27 carries the N-terminal 27 residues of PACAP-38. PACAP is a neuropeptide and is a member of a superfamily that includes several regulatory peptides, e.g., VIP, secretin and glucagon. PACAP is present, not only in various areas of the central nervous system, including the hypothalamus, posterior pituitary, cerebral cortex, and hippocampus, but also in peripheral tissues, such as the testis, adrenal gland, and the gut. At least two types of binding sites have been reported for PACAP in mammalian tissues, type I and type II, further divided into subtypes (PAC1, VPAC1, VPAC2). Type I receptors selectively recognize PACAP much more potently than VIP, but type II receptors display similar high affinity for PACAP-27, PACAP-38 and VIP. Type I PACAP receptors (PAC1) are abundant in the CNS whereas the amount of type II receptors is low. Type II (VIP-PACAP) receptors almost exclusively interact with adenylate cyclase. At least two effector systems, however, exist for type I PACAP-preferring receptors. It appears that type I receptors stimulate both adenylate cyclase and phospholipase C, this coupling to dual signaling cascades involving interactions with G proteins of the $G_s$ and $G_q$ types.

A PACAP inhibitor is any molecular species that interferes with normal PAC1 receptor activity, and includes for instance, PACAP inhibitors and PAC1 receptor antagonists. In some embodiments, a PACAP inhibitor may interfere with normal VPAC receptor activity. In certain embodiments, a PACAP inhibitor may act as a VPAC receptor antagonist. The PACAP inhibitor can be a PACAP or PACAP receptor binding molecule that interferes with the interaction between PACAP and PAC1. For instance it may be a peptide PACAP binding molecule such as short peptides and antibodies, including fragments of antibodies, such as Fc, which selectively bind to and inhibit the activity of the PACAP receptor (collectively referred to herein as "peptide substrates").

The PACAP inhibitor may function by preventing the transcription of PACAP or a PACAP receptor gene, preventing the processing or translation of PACAP or a PACAP receptor mRNA or preventing the processing, trafficking, or activity of a PACAP receptor protein when administered in vivo or in vitro to a mammalian cell which is otherwise competent to express active PACAP receptor. Thus, for example, PACAP inhibitors include repressors which prevent induction and/or transcription of the PACAP receptor gene, antisense sequences which selectively bind to PACAP receptor DNA or RNA sequences and which prevent the transcription or translation of the PACAP receptor gene, competitive and non-competitive inhibitors of the activity of the PACAP receptor protein. For example, an antisense molecule can be an oligonucleotide of between 5-100, preferably 10-50, preferably about 30 nucleotides in length, and complementary to a portion of the mRNA sequence (including the coding sequence) of the PACAP receptor gene. An siRNA molecule is preferably a double-stranded RNA molecule with a 19 base pair double-stranded region (corresponding to a sequence on the target gene or mRNA) with a 2 base overhang at both ends (preferably a TT dimer overhang at each end). Such molecules are described in greater detail herein. The term "PACAP inhibitor" is not intended to embrace non-selective suppressors of all gene expression or protein synthesis, or general toxins.

In addition, small molecules, peptide or non-peptides which structurally mimic the natural substrates of the PACAP receptor, but which do not activate the receptor fall within the class of PACAP inhibitors. This class of compounds also includes molecular species which do not mimic the natural substrates of the PACAP receptor, but which interact with the substrate binding domain or other regions of the PACAP receptor, preventing its activity. The PACAP receptor binding molecules may be easily prepared or identified by those of ordinary skill in the art using routine experiments since the PACAP receptor is a known compound which has been described structurally in the prior art.

Thus a PACAP inhibitor maybe an agent, ligand, agonist, or antagonist that binds to or exhibits an affinity for the PACAP receptor (PAC1) and does not activate the receptor. The PACAP inhibitors include, but are not limited to PACAP antagonists such as peptide substrates that bind to the receptor. Examples of peptide substrates useful according to the invention include: PACAP6-38, PACAP6-27 and mixtures thereof. PACAP6-38 (Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys SEQ ID NO:1) is a PAC1-specific receptor selective antagonist that is a truncated version of the PACAP peptide that is missing the first six amino acids of the carboxylic terminus. PACAP6-27 (Phe-Thr-Asp-Ser-Tyr-Ser-Arg-Tyr-Arg-Lys-Gln-Met-Ala-Val-Lys-Lys-Tyr-Leu-Ala-Ala-Val-Leu SEQ ID NO:2) is a selective PACAP antagonist that is a truncated version of the PACAP peptide. The truncations are on both the carboxy and the amino termini.

Other peptide substrates can easily be identified without undue experimentation in vitro based on their ability to bind or activate the PACAP receptor. To determine whether a peptide binds to the PACAP receptor any known binding assay may be employed. For example, in the case of a peptide that binds to the PACAP receptor the peptide may be immobilized on a surface and then contacted with a labeled PACAP receptor (or vice versa). The amount of PACAP receptor which interacts with the peptide or the amount which does not bind to the peptide may then be quantified to determine whether the peptide binds to PACAP receptor. A surface having a known peptide that binds to PACAP receptor such as a monoclonal antibody immobilized thereto may serve as a positive control.

The activation of the PACAP receptor can be assayed by measuring the increase of intracellular cAMP concentration, increase of the inositol-3-phosphate concentration, or expansion of nervous processes. The following descriptions are non-limiting examples only. The activation of the PACAP receptor can be assayed by incubating the cells in medium (e.g., DMEM, HANKS) in the presence of such a peptide at a temperature of about 37° C. for several minutes (e.g., 10 minutes). The time course of production of cAMP, inositol-3-phosphate and $Ca^{2+}$ can be detected by measuring methods well known in the art (Masmoudi et al., *FASEB*, 17:17-27 (2003)). Assays for measuring the production of cAMP, inositol-3-phosphate metabolism and $Ca^{2+}$ cellular concentration have been described in the art.

The "PACAP receptor" as used herein refers to the membrane-bound PAC1 protein. Cells where PACAP receptors are expressed, methods for preparing the cells, and cDNA vectors for their expression are well known in the art (Pisgna et al., *PNAS* 90: 6245-6249 (1993), Sreedharan et al., *Biochem. Biophys. Res. Commun.* 193:546-553 (1993)). In brief, PACAP receptors can be prepared from rat brain tissue from which the cerebellum is removed by homogenization at 4° C. Following centrifugation (1,000×g, 10 minutes, 4° C.), the supernatant is centrifuged at 30,000×g for 45 minutes at 4° C. and the pellet is washed and resuspended in 50 mM Tris-HCl buffer. Other methods are known to those of ordinary skill in the art. The receptors mentioned in the invention include not only those disclosed in these literature references, but also those which are derived from other various mammals and can be prepared according to the description of these literature references.

Another type of PACAP inhibitor is an siRNA which functions by RNA interference (RNAi). The process is known to occur in a wide variety of organisms, including embryos of mammals and other vertebrates. It has been demonstrated that dsRNA is processed to RNA segments 21-23 nucleotides (nt) in length, and furthermore, that they mediate RNA interference in the absence of longer dsRNA. Thus, these 21-23 nt fragments are sequence-specific mediators of RNA degradation. This present invention encompasses the use of these fragments (or recombinantly produced or chemically synthesized oligonucleotides of the same or similar nature) to enable the targeting of PACAP mRNAs for degradation in mammalian cells useful in the therapeutic applications discussed herein.

The methods for design of the RNA's that mediate RNAi and the methods for transfection of the RNAs into cells and animals is well known in the art and are readily commercially available (Verma N. K. et al., *J. Clin. Pharm. Ther.,* 28(5):395-404 (2004), Mello C. C. et al. *Nature,* 431(7006) 338-42 (2004), Dykxhoorn D. M. et al., *Nat. Rev. Mol. Cell Biol.* 4(6):457-67 (2003) Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK)). The RNAs are preferably chemically synthesized using appropriately protected ribonucleoside phosphoramidites and a conventional DNA/RNA synthesizer. Most conveniently, siRNAs are obtained from commercial RNA oligo synthesis suppliers listed herein. In general, RNAs are not too difficult to synthesize and are readily provided in a quality suitable for RNAi. A typical 0.2 μmol-scale RNA synthesis provides about 1 milligram of RNA, which is sufficient for 1000 transfection experiments using a 24-well tissue culture plate format.

The PACAP specific siRNA may be designed by selecting a sequence that is not within 50-100 bp of the start codon and the termination codon, avoids intron regions, avoids stretches of 4 or more bases such as AAAA, CCCC, avoids regions with GC content <30% or >60%, avoids repeats and low complex sequence, and it avoids single nucleotide polymorphism sites. The PACAP siRNA may be designed by a search for a 23-nt sequence motif $AA(N_{19})$. If no suitable sequence is found, then a 23-nt sequence motif $NA(N_{21})$ and convert the 3' end of the sense siRNA to TT. Alternatively, the PACAP siRNA can be designed by a search for $NAR(N_{17})YNN$. The target sequence should have a GC content of around 50%. The siRNA targeted sequence is further evaluates using a BLAST homology search to avoid off target effects on other genes or sequences. Negative controls are designed by scrambling targeted siRNA sequences. The control RNA has the same length and nucleotide composition as the siRNA but has at least 4-5 bases mismatched to the siRNA. The RNA molecules of the present invention can comprise a 3' hydroxyl group. The RNA molecules can be single-stranded or double stranded; such molecules can be blunt ended or comprise overhanging ends (e.g., 5', 3') from about 1 to about 6 nucleotides in length (e.g., pyrimidine nucleotides, purine nucleotides). In order to further enhance the stability of the RNA of the present invention, the 3' overhangs can be stabilized against degradation. The RNA can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

The RNA molecules used in the methods of the present invention can be obtained using a number of techniques known to those of skill in the art. For example, the RNA can be chemically synthesized or recombinantly produced using methods known in the art. Such methods are described in U.S. Published Patent Application Nos. US2002-0086356A1 and US2003-0206884A1 which are hereby incorporated by reference in their entirety.

The methods described herein are used to identify or obtain RNA molecules that are useful as sequence-specific mediators of PACAP mRNA degradation and, thus, for inhibiting PACAP and PACAP receptor activity. Expression of the PACAP receptor can be inhibited in humans in order to prevent the disease or condition from occurring, limit the extent to which it occurs or reverse it. The diseases and conditions that can be treated in this manner include but are not limited to anxiety disorders such as PTSD. Using the PACAP sequence, RNAs can be produced and tested for their ability to mediate RNAi in a cell, such as a human or other primate cell. Those RNA molecules shown to mediate RNAi can be tested, if desired, in an appropriate animal model to further assess their in vivo effectiveness.

The RNA molecules can be isolated using a number of techniques known to those of skill in the art. For example, gel electrophoresis can be used to separate RNAs from the combination, gel slices comprising the RNA sequences removed and RNAs eluted from the gel slices. Alternatively, non-denaturing methods, such as non-denaturing column chromatography, can be used to isolate the RNA produced. In addition, chromatography (e.g., size exclusion chromatography), glycerol gradient centrifugation, affinity purification with antibody can be used to isolate RNAs.

Any dsRNA can be used in the methods of the present invention, provided that it has sufficient homology to the PACAP gene or PACAP receptor gene to mediate RNAi. The dsRNA for use in the present invention can correspond to the entire PACAP or PACAP receptor gene or portions thereof. There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length. In certain embodiments the preferred length of the RNA of the invention is 21 to 23 nucleotides.

The PACAP inhibitors of the invention also encompass antisense oligonucleotides that selectively bind to a PACAP receptor nucleic acid molecule, and dominant negative constructs used to reduce the expression of the PACAP receptor. Antisense oligonucleotides are useful, for example, for reducing the expression of PACAP receptor proteins in PACAP receptor expressing cells.

As used herein, the term "antisense oligonucleotide" or "antisense" describes an oligonucleotide which hybridizes under physiological conditions to DNA comprising a particular gene or to an RNA transcript of that gene and, thereby, inhibits the transcription of that gene and/or the translation of the mRNA. The antisense molecules are designed so as to hybridize with the target gene or target gene product and thereby, interfere with transcription or translation of the target mammalian cell gene. Those skilled in the art will recognize that the exact length of the antisense oligonucleotide and its degree of complementarity with its target will depend upon the specific target selected, including the sequence of the target and the particular bases which comprise that sequence. The antisense must be a unique fragment. A unique fragment is one that is a 'signature' for the larger nucleic acid. It, for example, is long enough to assure that its precise sequence is not found in molecules outside of the PACAP receptor gene. As will be recognized by those skilled in the art, the size of the unique fragment will depend upon its conservancy in the genetic code. Thus, some regions of the PACAP receptor gene will require longer segments to be unique while others will require only short segments, typically between 12 and 32 base pairs (e.g. 12, 13, 14, 15, 16, 17, 18, 19, 20, 21, 22, 23, 24, 25, 26, 27, 28, 29, 30, 31 and 32 bases long).

It is preferred that the antisense oligonucleotide be constructed and arranged so as to bind selectively with the target under physiological conditions, i.e., to hybridize substantially more to the target sequence than to any other sequence in the target cell under physiological conditions. Based upon the known sequence of a gene that is targeted for inhibition by antisense hybridization, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 and, more preferably, at least 15 consecutive bases which are complementary to the target. Most preferably, the antisense oligonucleotides comprise a complementary sequence of 20-30 bases. Although oligonucleotides (complementary) may be chosen which are antisense to any region of the gene or RNA (e.g., mRNA) transcript, in preferred embodiments the antisense oligonucleotides are complementary to 5' sites, such as translation initiation, transcription initiation or promoter sites, that are upstream of the gene that is targeted for inhibition by the antisense oligonucleotides. In addition, 3'-untranslated regions may be targeted. Furthermore, 5' or 3' enhancers may be targeted. Targeting to mRNA splice sites has also been used in the art but may be less preferred if alternative mRNA splicing occurs. In at least some embodiments, the antisense is targeted, preferably, to sites in which mRNA secondary structure is not expected (see, e.g., Sainio et al., *Cell Mol. Neurobiol.*, (1994) 14(5):439-457) and at which proteins are not expected to bind. The selective binding of the antisense oligonucleotide to a mammalian target cell nucleic acid effectively decreases or eliminates the transcription or translation of the mammalian target cell nucleic acid molecule.

The PACAP inhibitor may be isolated from natural sources or synthesized or produced by recombinant means. Methods for preparing or identifying molecules which bind to a particular target are well-known in the art. Molecular imprinting, for instance, may be used for the de novo construction of macro molecular structures, such as peptides, which bind to a particular molecule. See for example, Kenneth J. Shea, *Molecular Imprinting of Synthetic Network Polymers: The De novo Synthesis of Molecular Binding In Catalytic Sites*, Trip, to May 1994; Klaus, Mosbach, Molecular Imprinting, Trends in *Biochem. Sci.,* 19(9), January 1994; and Wulff, G., In Polymeric Reagents and Catalysts (Ford, W. T., ed.) *ACS Symposium Series* No. 308, P. 186-230, *Am. Chem. Soc.* 1986. Binding peptides, such as antibodies, may easily be prepared by generating antibodies to the PACAP receptor or by screening libraries to identify peptides or other compounds which bind to the PACAP receptor.

Although the examples below are directed to a preferred embodiment of the invention, namely, PACAP peptide substrates and associated methods of use for inhibiting PACAP receptor activation, it should be understood that this description is illustrative only and is not intended to limit the scope of the instant invention. Any peptide or other molecule which binds to the PACAP receptor and inhibits activation of the PACAP receptor is encompassed by the methods of the invention. For example, the molecules of the invention include the peptide substrates, e.g. PACAP6-38, PACAP6-27 antibodies and functionally active fragments of antibodies and other small peptides exhibiting PACAP receptor specificity, as well as non-peptide compounds.

The PACAP inhibitor is an isolated molecule. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation, the molecular species may comprise only a small percentage by weight of the preparation. The molecular species is nonetheless substantially pure in that it has been substantially separated from the substances with which it may be associated in living systems.

Identification of molecules useful according to the invention, also can be carried out utilizing a competition assay. If a molecule being tested competes with the PACAP6-38, PACAP or an anti-PACAP monoclonal antibody, as shown by a decrease in binding of the PACAP6-38, PACAP or the monoclonal antibody, then it is likely that the molecule, PACAP6-38, PACAP and the monoclonal antibody bind to the same, or a closely related, epitope.

In some embodiments the PACAP inhibitor is an antibody, or a functionally active antibody fragment, or a peptide substrate Antibodies are well known to those of ordinary skill in the science of immunology. As used herein, the term "antibody" means not only intact antibody molecules but also fragments of antibody molecules retaining PACAP receptor binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983)).

In certain embodiments, the peptide fragment to which an antibody is directed is the carboxyl-terminal end of PACAP. For example, a PACAP inhibitor may be an antibody directed to the carboxy-terminal end of PACAP38. In particular embodiments, the amino acid sequence to which an antibody is directed is Tyr-Lys-Gln-Arg-Val-Lys-Asn-Lys-NH2 (SEQ ID NO:3) or Cys-Tyr-Lys-Gln-Arg-Val-Lys-Asn-Lys-NH2 (SEQ ID NO:4). Such sequences are useful, for example, for producing antibodies.

In general, the PACAP inhibitors of the invention are useful for treating anxiety disorders characterized by the increased expression of PACAP. In particular the inhibitors of the invention are useful for treating anxiety disorders such as PTSD in female subjects. The term "treatment" and "treating" is intended to encompass also prophylaxis, therapy and cure. The terms "treatment" and "treating" as used herein refer to inhibiting completely or partially the expression or activity of PACAP and/or PACAP receptor, as well as inhibiting an increase in the expression or activity of PACAP and/or PACAP receptor. In some embodiments, the efficacy of treatment with a PACAP inhibitor or PAC1 receptor antagonist and/or VPAC receptor antagonist is monitored by assessing a subject's weight gain or loss. For example, in some embodiments, weight gain in a subject is indicative that treatment with a PACAP inhibitor or PAC1 receptor antagonist and/or VPAC receptor antagonist is effective for treating a particular anxiety disorder in the subject, whereas no weight gain, or weight loss, is indicative that treatment is not effective.

The terms "reduce" or "eliminate" refers to reducing or eliminating the symptoms of the disorders as determined by known psychological assessments. In addition the reduction and elimination of the disorders can be determined from the observation of clinical symptoms. These factors are well known to those of ordinary skill in the art and can be addressed with no more than routine experimentation and examination.

An "anxiety disorder" as used herein refers to a disorder characterized by increased anxiety. Anxiety disorders include but are not limited to social phobia, post-traumatic stress disorder, panic disorder, panic attacks, and obsessive-compulsive disorder. Anxiety disorders can be associated with a variety of physical systems, including a faster heart rate, skipped heartbeats, rapid breathing, sweating, trembling, dizziness, dry mouth, and weight loss. Post traumatic stress disorder (PTSD) as used herein refers to disorder that occurs after exposure to a traumatic event and results in the subject feeling scared, confused, and/or angry to the extent that daily activities are difficult to perform. Traumatic events include but are not limited to combat or military exposure, child sexual or physical abuse, terrorist attacks, sexual or physical assault, serious accidents, and natural disasters (such as a fire, tornado, hurricane, flood, or earthquake).

The agents of the invention are administered in "effective amounts". The "effective amount" is that amount which is capable of at least partially preventing, reversing, reducing, decreasing, ameliorating, or otherwise suppressing the particular disorder being treated. A therapeutically effective amount can be determined on an individual basis and will be based, at least in part, on consideration of the species of mammal, the mammal's age, sex, size, and health; the PACAP inhibitor used, the type of delivery system used; the time of administration relative to the severity of the disease; and whether a single, multiple, or controlled-release dose regiment is employed. In general, an effective amount for treating an anxiety disorder will be that amount necessary to inhibit the onset or progression of, or to reduce or eliminate the disorder. This can be determined by observing symptoms of anxiety. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

A variety of administration routes are available. The particular mode selected will depend of course, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. The PACAP inhibitors of the invention can be administered by any method which allows the inhibitor to reach the target cells, e.g., PACAP receptor presenting cells. These methods include, e.g., injection, infusion, deposition, implantation, anal or vaginal supposition, oral ingestion, inhalation, topical administration, administration by catheter or any other method of administration where access to the target cell by the inhibitor is obtained. The term "parenteral" includes intravenous, intradermal, subcutaneous, intramuscular, or intraperitoneal injections. In some embodiments, the injections can be given at multiple locations.

The active agents thus can be provided in pharmaceutical preparations. When administered, the pharmaceutical preparations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicyclic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts. Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The pharmaceutical preparations of the present invention contain an effective amount of an agent included with a pharmaceutically-acceptable carrier. The term "pharmaceutically-acceptable carrier" as used herein means one or more compatible solid or liquid filler, diluents or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy. Carrier formulations suitable for oral, topical, subcutaneous, intravenous, intramuscular, etc. can be found in Remington's Pharmaceutical Sciences, Mack Publishing Company, Easton, Pa., USA.

The compounds useful in the invention may be used alone, without other active agents. They also may be used together with other active agents, such as anti-anxiety medications known to be useful in treating the conditions described herein. The agents may be delivered separately from one another or in the form of a cocktail of two or more agents. A cocktail is a mixture of any one of the compounds useful with this invention with another active agent.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another therapeutic, for instance, a chelating agent that can bind up additional chemicals in the body, a sub-therapeutic dosage of either or both of the molecules may be used. A "sub-therapeutic dose" as used herein refers to a dosage which is less than that dosage which would produce a therapeutic result in the subject if administered in the absence of the other agent.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration. The present invention involves administration of the therapeutic compounds orally.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

According to the methods of the invention, the compound may be administered in a pharmaceutical composition. In general, a pharmaceutical composition comprises the compound of the invention and a pharmaceutically-acceptable carrier. Pharmaceutically-acceptable carriers are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by Sawhney et al. (*Macromolecules,* 26, 581-587 (1993)), the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Therapeutic formulations of the active compounds may be prepared for storage by mixing an active compound having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

A peptide, for instance, may be administered directly to a cell or a subject, such as a human subject alone or with a suitable carrier. Alternatively, a peptide may be delivered to a cell in vitro or in vivo by delivering a nucleic acid that expresses the peptide to a cell. Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. For certain uses, it is preferred to target the nucleic acid molecule to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

The active compound of the invention may also be expressed directly in mammalian cells using a mammalian expression vector. Such a vector can be delivered to the cell or subject and the peptide expressed within the cell or subject. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the α-fetoprotein promoter.

As used herein, a "vector" may be any of a number of nucleic acid molecules into which a desired sequence may be inserted by restriction and ligation for expression in a host cell. Vectors are typically composed of DNA although RNA vectors are also available. Vectors include, but are not limited to, plasmids, phagemids and virus genomes. An expression vector is one into which a desired DNA sequence may be inserted by restriction and ligation such that it is operably joined to regulatory sequences and may be expressed as an RNA transcript.

A "subject" shall mean a human or non-human mammal, including but not limited to, a dog, cat, horse, cow, pig, sheep, goat, chicken, primate, rat, and mouse. In preferred embodiments the subject is a human female.

The materials for use in the invention, such as the PACAP inhibitors are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a peptide, antibody, DNA or RNA which selectively binds to PACAP or a PACAP receptor. The kit may be a diagnostic or therapeutic kit. For instance, the kit may also have containers comprising PACAP inhibitors and a substrate for detecting activation of the PACAP receptor. Additionally the kit may include containers for buffer(s) useful in the assay. In other examples, the kit may comprise packaging material and a formulation comprising an PACAP inhibitor, wherein the packaging material comprises a label or package insert that states that the formulation can be used for the diagnostic or prognostic methods described herein or administered to a subject having anxiety for a duration effective to reduce or eliminate the anxiety.

In another example of the invention, the kit may comprise packaging material and a formulation that comprises a diagnostic or therapeutic agent described herein, wherein the packaging material comprises a label or package insert that describes the methods of the invention.

The invention also involves methods for diagnosing an anxiety disorder in a female subject. Diagnostic methods include the collection or analysis of a tissue sample from the subject. The tissue sample may be any biological sample from a subject, and includes whole or partial tissue, multiple tissues in whole or in part, cells or cell extracts. Thus, in some embodiments the tissue sample may be a DNA sample. In some embodiments it is preferred that the sample be one that is easily obtained from a subject, such as, for instance, blood, plasma, CSF. The term collection, as used herein refers to the removal of a sample from the body. In some instances the invention may involve the analysis of the biological sample in the body using in vivo diagnostic methods.

The diagnostic methods involve analyzing one or more components identified herein as providing information on a subject's stress response. For instance, PACAP protein expression levels may be examined in the tissue sample in order to diagnose the anxiety disorder. Elevated tissue PACAP expression levels as compared to a control value are indicative of a subject having anxiety disorder. A control value may be obtained from a tissue sample of a subject who does not have an anxiety disorder, or alternatively may be a baseline value, known in the art. A control value may also be a level known to exist in to subject prior to a stress inducing incident.

The anxiety disorder may be a PTSD, as described in more detail above. In order to determine whether a subject has a PTSD it is possible to observe endophenotypes of PTSDs. An endophenotype is a biomarker of a psychiatric condition. Typically an endophenotype associated with a PTSD includes at least some of the following criteria: association with PTSD in the population, it is heritable, it is primarily state-independent (manifests in an individual whether or not PTSD is active, and within families, endophenotype and PTSD co-segregate. Endophenotypes associated with PTSD include but are not limited to intrusive re-experiencing, avoidance, hyperarousal, or fear discrimination. In some instances the subject may be identified as one that has been exposed to a trauma.

Another diagnostic method is one for identifying a subject at risk of developing an anxiety disorder by analyzing a DNA sample of a subject. One method for analyzing the DNA involves the identification of the presence or absence of a SNP in a PAC1 receptor gene; and diagnosing the anxiety disorder in the subject having the SNP in the PAC1 receptor gene. The gene encoding the PAC1 receptor is referred to as ADCYAP1R1. The sequence for the ADCYAP1R1 is found (NCBI Reference sequence NM_001199635).

A single nucleotide polymorphism, or SNP, is a region of DNA which includes a single nucleotide difference between the DNA of different members of a species. SNPs are sometimes associated with phenotypic changes in a subject. One SNP that is useful in the methods of the invention is located at position rs2267735 of the ADCYAP1R1 gene. The SNP may be a G-C allelic mutation and has the following sequence: 5'-tcaggtca(g/c)agaggacg-3' (SEQ ID NO:5). It's complement has the following sequence: 5'-cgtcctct(c/g)tgacctga-3' (SEQ ID NO:6). The presence of the SNP of SEQ ID NO:5 in a subject correlates with the risk of the subject developing anxiety or PTSD.

The DNA sample may also be analyzed for epigenetic methylation at important sites. For instance, epigenetic methylation of a first site within a ADCYAP1R1 CpG island is useful for diagnosing an anxiety disorder. Specifically a subject having elevated levels of epigenetic methylation is at risk of an anxiety disorder.

The methods for analyzing PACAP and PAC expression, as well as the presence of SNPs or epigenetic methylation are well known in the art. Examples of such methods are provided in the Examples section. However, any art known method may be used to accomplish the methods described herein.

The levels of protein or nucleic acid or the presence or absence of proteins or nucleic acids may be measured using any of a number of techniques available to the person of ordinary skill in the art, e.g., direct physical measurements (e.g., mass spectrometry), binding assays (e.g., immunoassays, agglutination assays, and immunochromatographic assays), Polymerase Chain Reaction (PCR) technology, branched oligonucleotide technology, Northern blot technology, oligonucleotide hybridization technology, and in situ hybridization technology. The method may also comprise measuring a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Hybridization methods for nucleic acids, for instance, are well known to those of ordinary skill in the art (see, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York). The nucleic acid molecules hybridize under stringent conditions to nucleic acid markers expressed in cells.

Binding assays for measuring levels of protein may use solid phase or homogenous formats. Suitable assay methods include sandwich or competitive binding assays. Examples of sandwich immunoassays are described in U.S. Pat. No. 4,168,146 to Grubb et al. and U.S. Pat. No. 4,366,241 to Tom et al., both of which are incorporated herein by reference. Examples of competitive immunoassays include those disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

In general, immunoassays involve the binding of proteins in a sample to a solid phase support such as a plastic surface. Detectable antibodies are then added which selectively binding to the protein of interest. Detection of the antibody indicates the presence of the protein. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described in Immunoassays for the 80's, A. Voller et al., Eds., University Park, 1981, which is incorporated herein by reference.

The methods may also be accomplished using in situ hybridization or in vivo imaging methods. In situ hybridization technology involves the addition of detectable probes which contain a specific nucleotide sequence to fixed cells. If the cells contain complementary nucleotide sequences, the probes, which can be detected, will hybridize to them. In vivo imaging involves the labeling of nucleic acids or proteins in vivo. The probes used in such methods are typically labeled for detection.

A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as P32 or H3, luminescent markers such as fluorochromes, optical or electron density markers, etc., or epitope tags such as the FLAG epitope or the HA epitope, biotin, avidin, and enzyme tags such as horseradish peroxidase, galactosidase. The label may be bound to a peptide during or following its synthesis. There are many different labels and methods of labeling known to those of ordinary skill in the art. Examples of the types of labels that can be used in the methods described herein include enzymes, radioisotopes, fluorescent compounds, colloidal metals, chemiluminescent compounds, and bioluminescent compounds.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

To examine whether the PACAP/PAC1 pathway is associated with PTSD, PACAP peptide levels were examined in peripheral blood samples from a highly traumatized, at risk population that was matched on age, sex, and trauma histories (n=64). A Demographic Form was used to assess subject age, self-identified race, marital status, education, income, employment, disability status, and questions about lifetime and current substance abuse.

This highly traumatized, civilian, cross-sectional cohort was previously described in candidate gene-association studies of PTSD and depression (Binder et al., *JAMA* 299, 1291-305 (2008), Bradley et al., *Arch Gen Psychiatry* 65, 190-200 (2008), Gillespie et al., *Depress Anxiety* 26, 984-92 (2009)). The Traumatic Events Inventory (TEI (Schwartz et al., *Psychiatr Serv* 56(2):212-215 (2005), Schwartz et al., *Psychosomatics* March-April 47(2): 136-142 (2006); Binder et al., *JAMA* 299, 1291-305 (2008)) was used to identify subjects in the cohort. TEI is a 14-item screening instrument for lifetime history of traumatic events. For each traumatic event, the TEI assesses experiencing and witnessing of events separately. The total number or types of trauma exposure variable was created and used.

Research interviews and salivary DNA and blood samples were collected from patients receiving services in primary care clinics. DNA came from saliva collected in Oragene vials (DNA Genotek Inc., Ontario Canada) or from whole blood collected in EDTA tubes. For genotyping, 500 µl of whole blood and 200 µl of oragene saliva were used for extraction. DNA from saliva was extracted using the DNAdvance extraction kit and DNA from blood was extracted using the Genfind v2 kit (Beckman Coulter Genomics, Danvers Mass.). Both extraction methods utilized automation methods on the Biomek NX (Beckman Coulter Inc., Brea, Calif.).

Plasma was collected in EDTA blood collection tubes, put on ice immediately, centrifuged at 3000 rpm for 15 min, then aliquoted into 1 ml samples and placed at −80° C. To minimize degradation of the plasma, repeat freezing/thawing of the plasma was avoided.

PTSD measures were based on the PTSD Symptom Scale (PSS) (Bangasser et al., *Mol Psychiatry* 15, 877, 896-904 (2010)), which was validated within this population using the Clinician Administered PTSD Scale. The PTSD Symptom Scale is a psychometrically valid 17-item self-report scale assessing PTSD symptomotology (Binder et al., *JAMA* 299, 1291-305 (2008); Coffey et al., *J Trauma Stress*. 11(2): 393-399 (1998); Falsetti et al., *The Behavior Therapist* 1993:161-162; Foa et al., *J Trauma Stress* 13, 181-91 (2000); Schwartz et al., *Psychiatr Serv.* 56(2): 212-215 (2005), Schwartz et al. *Psychosomatics* 47(2): 136-142 (2006)) over the two weeks prior to the study. The PSS frequency items ("0: not at all" to "3: >5 times a week") were summed to obtain a continuous measure of PTSD symptom severity ranging from 0-51. For this sample, previously described in Gillespie et al. (Gillespie et al., *Depress Anxiety* 26, 984-92 (2009)), the PSS frequency items had a standardized alpha coefficient of 0.93 (M=13.46, SD=12.18). Each subscale (Intrusive, Avoidant, Hyperarousal) may also be summed to obtain a symptom subscale score, as in FIGS. 1C-1E. The categorical diagnosis of PTSD was determined based on DSM-IV A-E criterion responses to the PSS questionnaire (A, presence of trauma; B, presence of at least 1 re-experiencing symptom; C, presence of at least 3 avoidance/numbing symptoms; D, presence of at least 2 hyperarousal symptoms; and E, present for at least 1 month).

PACAP peptide levels were examined using radioimmunoassay (RIA). PACAP38 RIA (1:30,000, Peninsula Laboratories, Belmont, Calif.) was performed using double antibody immunoprecipitation (Girard et al., *J Neurochem* 99(2): 449-513 (2006)). PACAP38, denoting the 38-amino acid peptide form of PACAP, in human plasma samples was concentrated on C18 Sep-Pak solid-phase cartridge minicolumns (Waters, Milford, Mass.) (Brandenburg et al., *J Neurosci* 17(11): 4045-55 (1997)). Briefly, the samples were recycled 3 times onto the minicolumns, washed with 0.1% trifluoroacetic acid (TFA) and eluted with 80%/0.1% TFA. The eluates were dried under reduced pressure and resuspended in 0.1 M sodium phosphate buffer (pH 7.4) containing 0.5% bovine serum albumin and 0.3 mg/ml phenylmethylsulfonylfluoride, immediately before assay. Peptide recovery from the Sep-Pak cartridges was 85%. Each sample was assayed over a dilution range to ensure data interpolation within the linear range of the standard curve; assay midpoint was 3.5 fmol. With the initial sample, the median level was 20 pM, such that 'low' PACAP were those <20 pM, and 'high' PACAP were those with levels >20 pM.

An additional 93 subjects were analyzed from the same initial population for a replication of the PACAP-PTSD association analysis. For the replication sample, the same RIA methods above were used. Due to increased variability in the overall second assay, the extreme tails of the samples (the lowest 10% and highest 10%) of the PACAP pM levels in the replication cohort (blinded to patient status) were removed to avoid spurious high or low readings. These data were analyzed in the same way, with the identification of subjects with high vs. low PACAP levels to predict level of PTSD symptoms. The median was 17.2 pM, such that 'low' PACAP were those <17.2 pM, and 'high' PACAP were those with levels >17.2 pM.

Figure 1B:
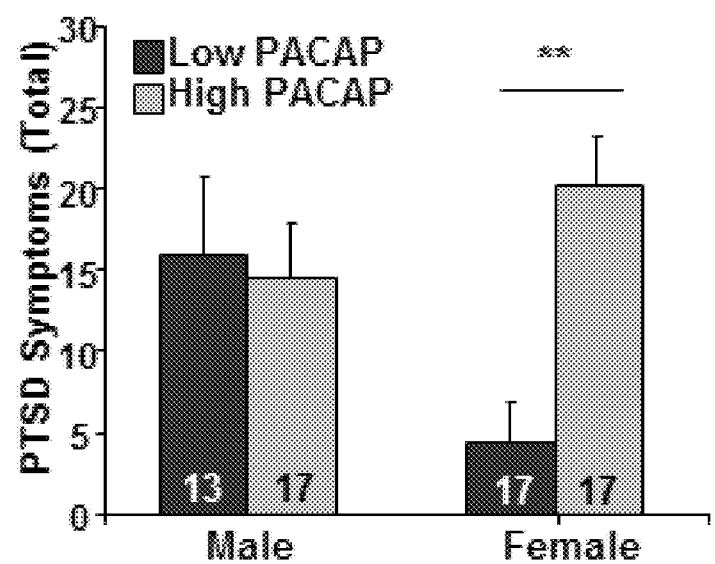
FIG. 1B shows a graph of total PTSD symptoms (y axis) relative to sex and levels of plasma PACAP38 (N=64, low: <20 pM, high: >20 pM); females with high PACAP blood levels have increased PTSD symptoms (**, p<0.0005).
Figure 1C:
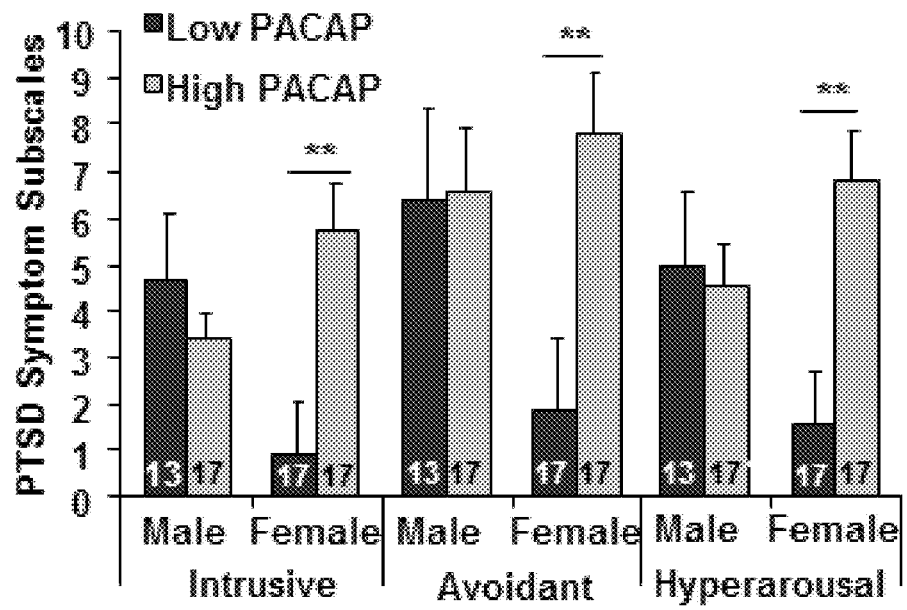
FIG. 1C shows a graph of PACAP levels (low vs. high) differentially associated with PTSD Intrusive, Avoidance, and Hyperarousal symptoms in females (N=64,** p<0.005).
Figure 1D:
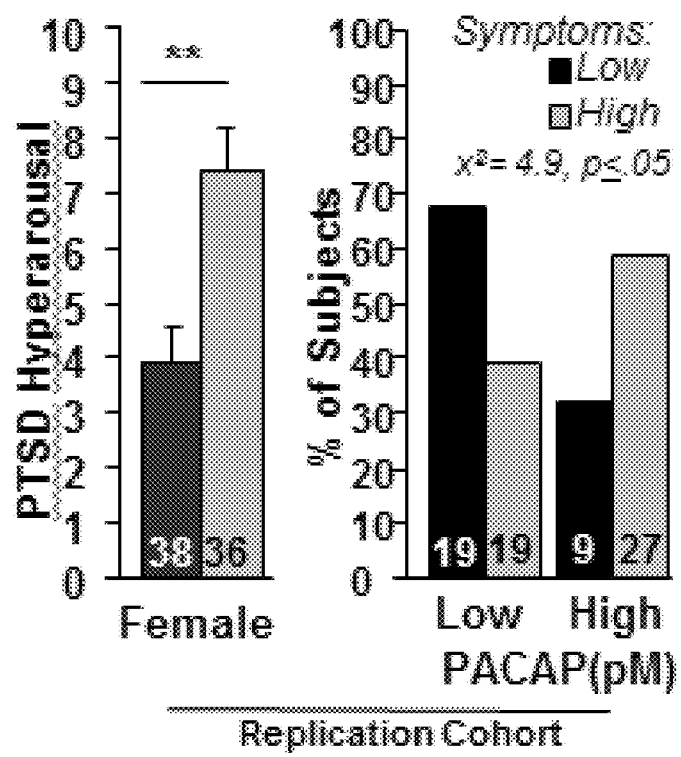
FIG. 1D shows a graph of PACAP levels (low vs. high) examined in a replication sample of additional highly traumatized women, with differential association in hyperarousal symptoms (left, N=74,** p=0.002) and in clinically significant PTSD symptoms (right, $\chi2$=4.9, p<0.05).

PTSD symptoms were significantly correlated with PACAP38 blood levels in females ($p<0.005$, $r=0.497$, FIG. 1A), but not in males ($p>0.5$). Also in females, PTSD diagnosis was associated with PACAP38 levels ($p<0.001$), with higher PACAP38 found in the PTSD cohort. Furthermore, PACAP levels (median split, low vs. high) were differentially associated with PTSD symptoms in females (FIG. 1B). PACAP38 levels also predicted differential response on all three symptom clusters necessary to fulfill diagnostic criteria for PTSD (intrusive re-experiencing (e.g., trauma flashbacks), avoidance (e.g., avoidance of trauma reminders) and hyperarousal (e.g., increased startle response)) in females but not males (FIG. 1C). These analyses were repeated in a second, all female cohort (N=74) with similar findings (FIG. 1D; high vs. low PACAP38 levels, controlling for age, substance abuse and total trauma exposure, one-tailed t-tests: total symptoms, $p<0.05$, hyperarousal symptoms, $p<0.001$; and % with clinically significant symptoms, $\chi2=4.9$, $p<0.05$). Common stress related phenomena (depression and history of substance abuse) were controlled for, and the effect of PACAP level on PTSD remained ($p<0.05$). In contrast, there did not appear to be an effect of PACAP level on depression symptoms or substance abuse when controlling for PTSD.

Example 2

Figure 1E:
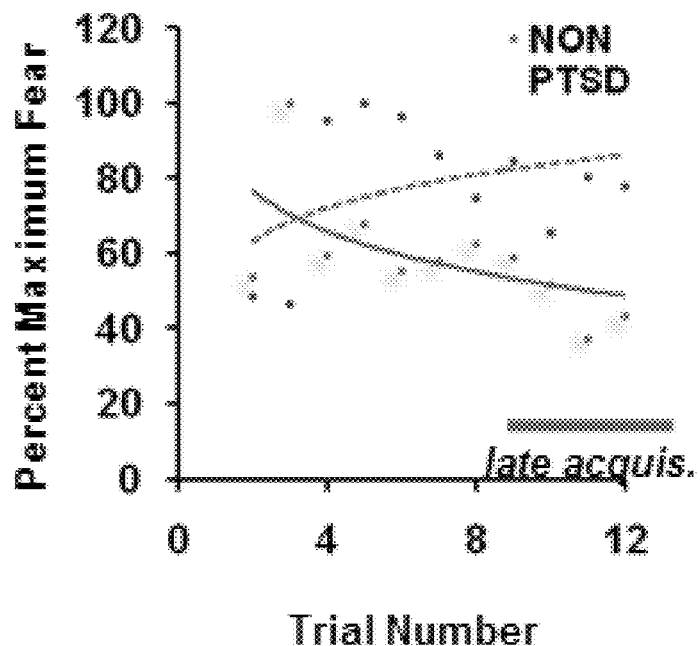
FIG. 1E shows a graph of subjects with PTSD having increased fear responses (measured with acoustic startle reflex (EMG) in humans), in contrast to those without PTSD habituate over time, most notable in late acquisition (bar).

Subjects with PTSD have been found to have abnormally high conditioned fear responses. To assess the physiological (electromyographic) levels of conditioned fear for 27 participants (16 male, 11 female) with high PACAP blood levels, fear potentiation was determined. The acoustic startle reflex was measured in the presence of startle cues alone, or startle cues combined with stimuli paired (conditioned stimulus, CS+) or unpaired (CS–) with an aversive airblast (FIG. 1E). The human startle response data were acquired at a 1000 Hz sampling frequency using the electromyography (EMG) module of the Biopac MP150 for Windows (Biopac Systems, Inc., Aero Camino, Calif.). The acquired data were filtered, rectified, and smoothed using MindWare software (MindWare Technologies, Ltd., Gahanna, Ohio) and exported for statistical analyses. The EMG signal was filtered with low- and high-frequency cutoffs at 28 and 500 Hz, respectively. The maximum amplitude of the eyeblink muscle contraction 20-200 ms after presentation of the startle probe was used as a measure of the acoustic startle response.

The eyeblink component of the acoustic startle response was measured by EMG recordings of the right orbicularis oculi muscle with two 5-mm Ag/AgCl electrodes filled with electrolyte gel (Jovanovic et al., *Biol Psychiatry* 57(12): 1559-64 (2005); Jovanovic et al., *Behav Neurosci.* 120(5): 995-1104 (2006)). One electrode was positioned 1 cm below the pupil of the right eye and the other was 1 cm below the lateral canthus. Impedance levels were less than 6 kilo-ohms for each participant. The startle probe was a 108-dB (A) SPL, 40 ms burst of broadband noise with near instantaneous rise time, delivered binaurally through headphones.

The fear-potentiated startle task included two phases: habituation and conditioning. The habituation phase consisted of six startle probes presented alone (noise-alone trials, NA). Immediately following habituation, participants underwent the conditioning phase, which consisted of three blocks, each of which included four trials of each CS type and four NA trials for a total of 12 trials per block. All CS+ (i.e., danger cue) trials were reinforced with the unconditioned stimulus (US), while the CS– (i.e. safety cue) trials were not reinforced. Both conditioned stimuli were different colored shapes presented on a computer monitor and were six seconds in duration. The US was a 250 ms air blast with an intensity of 140 psi directed to the larynx. The air blast was emitted by a compressed air tank attached to the polyethylene tubing and controlled by a solenoid switch. In all phases of the experiment, inter-trial intervals were of randomized duration ranging from 9 to 22 seconds.

Figure 1F:
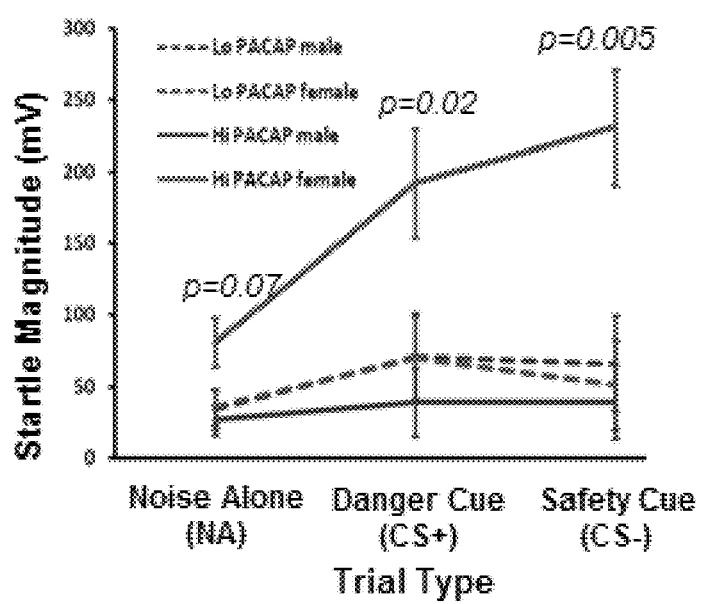
FIG. 1F shows a graph across all subjects, females, but not males, having high PACAP levels showing enhanced startle responses to both fear (CS+, p=0.02) cues and safety (CS−, p=0.005) cues during the late acquisition period (N=27 (16 male, 11 female)). Bars represent mean±SEM, N's for each group are shown at bottom of bar graph.

The data demonstrates that female (but not male) subjects with high PACAP38 levels demonstrated markedly increased startle reflex responses to both CS+ and CS– cues. This was particularly pronounced during the late acquisition phase when normal subjects had habituated to the fearful stimuli (FIG. 1F).

Example 3

To assess a genetic association of PTSD with polymorphisms in either the PACAP (ADCYAP1) or PAC1 receptor (ADCYAP1R1) locus, a tag-SNP analysis (r2=0.8; MAF=0.1) was conducted across the PACAP (ADCYAP1) or PAC1 receptor (ADCYAP1R1) genes with a total of 44 SNPs (14 ADCYAP1 and 30 ADCYAP1R1 SNPs). Logistic regression was used to determine SNP association with PTSD diagnosis in this cohort of highly traumatized urban civilian subjects (n=798) (Gillespie et al., *Gen Hosp Psychiatry* 31, 505-14 (2009)) in total, or stratified by gender (females: n=503; males: n=295).

Pairwise tagging (R2>0.8, MAF>0.1) was used to choose tag-SNPs for both ADCYAP1 and ADCYAP1R1 (P. I. W. de Bakker et al., *Nature Genetics* 37(11):1217-23 Nov. 2005)). The coordinates were chr18:885000-906000 and chr7: 31048667-31117836 for ADCYAP1 and ADCYAP1R1, respectively (NCBI B36) which includes approximately 10 kb upstream and 5 kb downstream of the coding regions for both genes. To capture tag-SNPs in the African American population, tag-SNPs for both the YRI (Yoruba in Ibadan, Nigeria) and CEU (Utah residents with Northern and Western European ancestry from the CEPH collection populations) populations were included. SNPs were generated from HapMap Data Phase III/Rel#2, February 9, dbSNP b126. Coding SNPs were also included in the genotyping panel. Genotypes for the tag-SNPs were generated using SEQUENOM iPLEX®. Further genotyping for rs2267735 (ADCYAP1R1) was done using TAQMAN®. SEQUENOM® genotypes were collected using the iPLEX® chemistries and the MassARRAY® system (Sequenom, Inc., San Diego, Calif.). SNP assays that had a <90% call rate for any of the chips were not analyzed (8/42 for ADCYAP1R1; 5/22 for ADCYAP1). SNP assays that were non-polymorphic or failed HWE at p<0.02 were also removed and not analyzed (4/34 for ADCYAP1R1; 3/17 for ADCYAP1). The averaged call rate ranged from 93-98%. For TAQMAN®, SNP assays with a call rate less than 95% were excluded. TAQMAN® reactions were performed using TAQMAN® SNP Genotyping Assays along with TAQMAN® Genotyping Master Mix (Applied Biosystems Inc., Foster City, Calif.). Alleles were discerned using the 7900HT Fast Real-Time PCR system.

Negative controls and within- and across-plate duplicates were used for quality control. Discordant samples were removed prior to analysis. For all SEQUENOM® genotypes there was a 11.9% duplication rate and 0.005% discordance rate. The duplication rate for TAQMAN® genotypes was 6.8%. There were no within method discordants. ADCYAP1R1 receptor SNP rs2267735 was genotyped using both TAQMAN® and SEQUENOM® with an across method duplication rate of 6.8% and a discordance rate of 0.1%. All negative controls passed quality control.

Figure 2A:
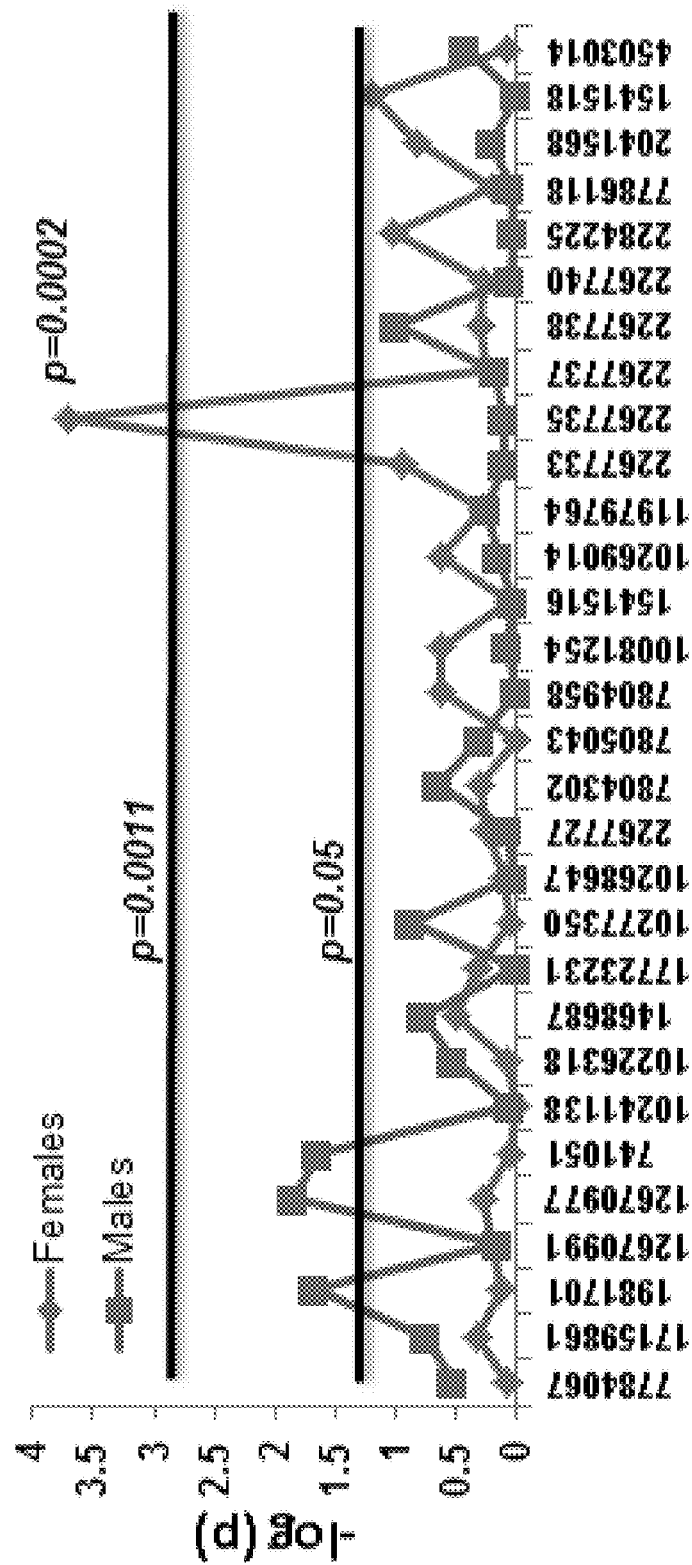
FIG. 2A shows 30 single nucleotide polymorphisms (SNPs) spanning the ADCYAP1R1 gene on the x-axis, with the −log(p-value) of the logistic regression for the association of each SNP with PTSD diagnosis (based on the DSM-IV criteria from the PTSD Symptom Scale). Subjects were analyzed with logistic regression in females only (N=503) or males only (N=295). The two horizontal lines represent the nominal p=0.05 or the p-value corrected for 44 SNPs, p=0.0011 (correcting for 30 ADCYAP1R1 SNPs and 14 ADCYAP1 SNPS (FIG. 6)). A single polymorphism, rs2267735 is the only SNP surviving testing for multiple corrections (p=0.0002).
Figures 2B, 2C:
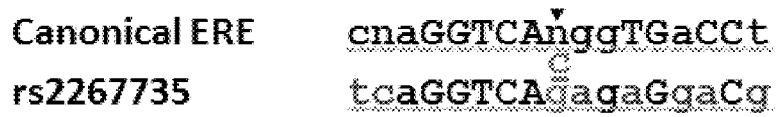
FIG. 2B shows a table of p-values resulting from the association of each genotyped, ADCYAP1R1 SNP with PTSD diagnosis (by gender). The location, on Chromosome 7 (GRCh37), for each SNP including the distance (bp) between the SNPs is given. The average distance between SNPs is 2.2 kb. SNP rs2267735 is located in an intron of ADCYAP1R1, and is not in LD with other SNPS (for African Americans in our population, data not shown).
FIG. 2C shows a SNP rs2267735 (C/G) (SEQ ID NO: 5), located within a canonical estrogen response element (ERE) binding site (SEQ ID NO: 93).
Figure 6:
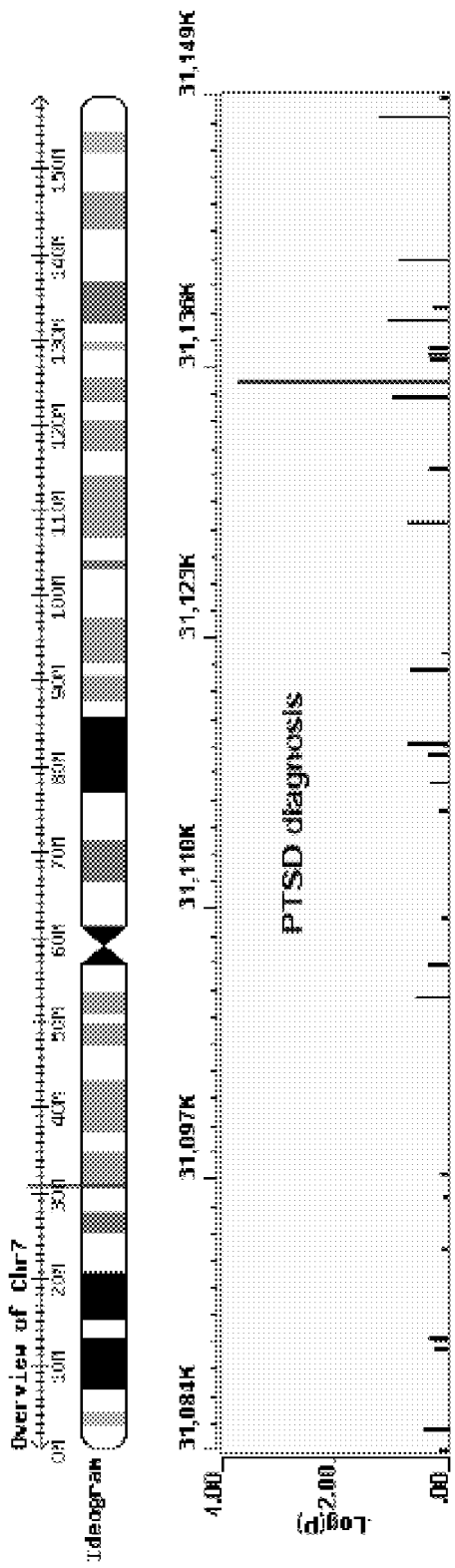
FIG. 6 depicts ADCYAP1R1 Tag SNP location and LD plot.
Figure 6:
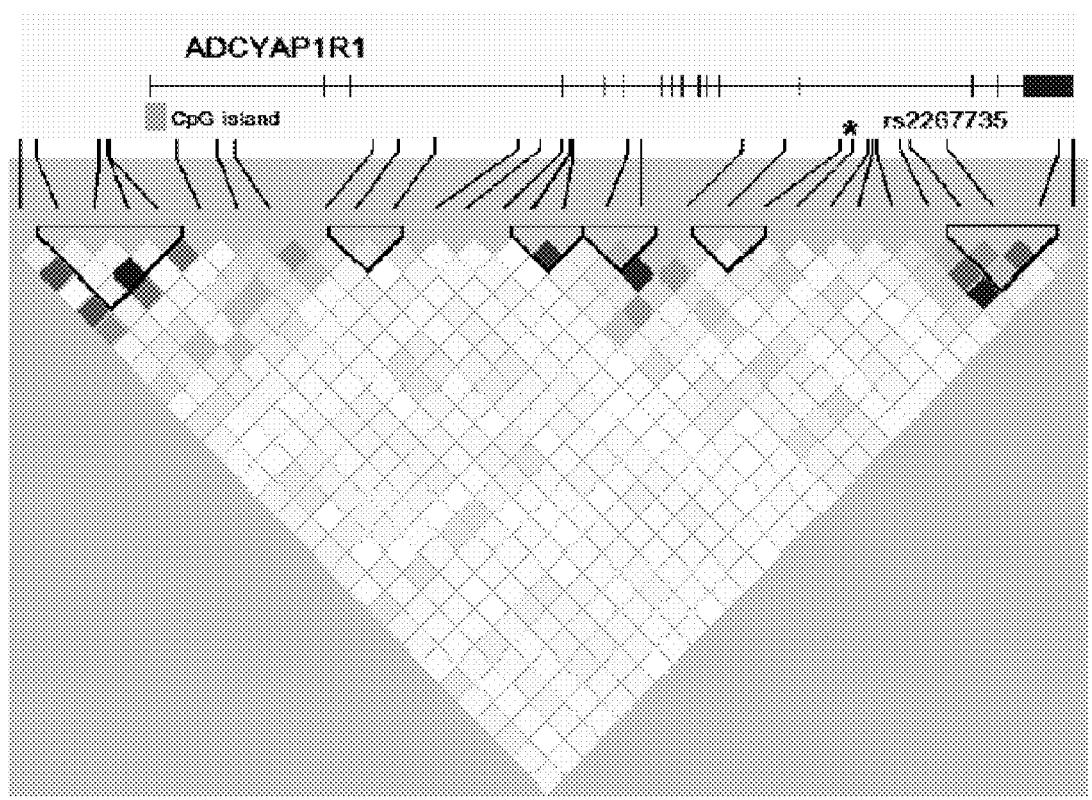
Figure 7:
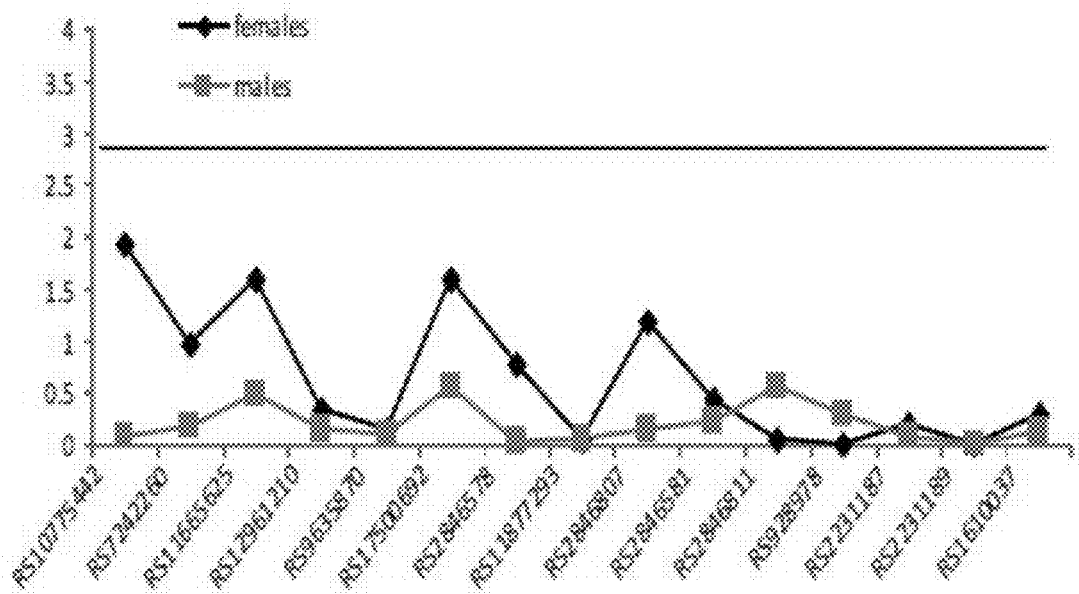
FIG. 7 shows a graph of ADCYAP1 Tag SNP occurrence in females and males.

The ADCYAP1R1 receptor SNP rs2267735 (SEQ ID NO:5 and SEQ ID NO:6) (p=0.0002 in females; NS in males) was significant after experiment-wide multiple correction for sex and 44 independent tests (FIGS. 2A-2B and FIG. 6). No SNPs in the ADCYAP1 gene met experiment-wide criteria for association (FIG. 7).

Figures 3A, 3B:
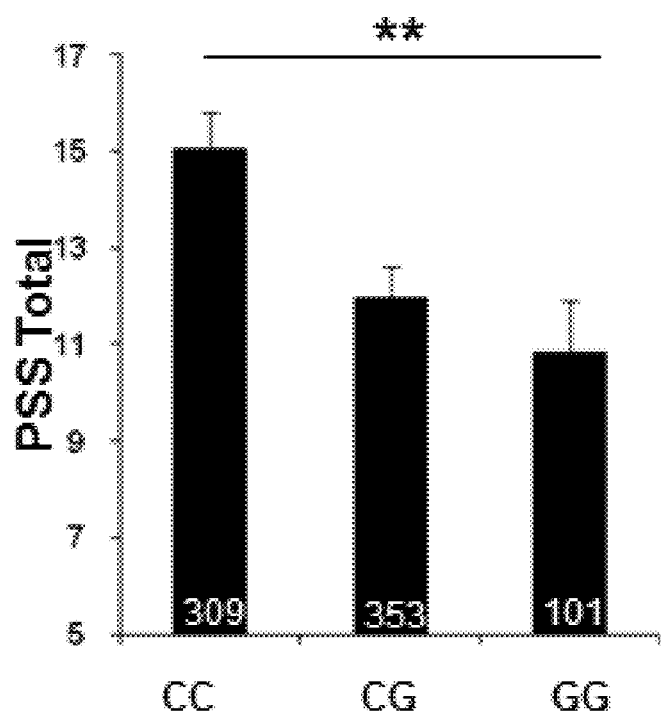
FIG. 3A shows a table demonstrating the N, Wald $\chi2$, and p-value, in males and females, in the original, replication, and combined samples for logistic regression of the main effect of rs2267735 on PTSD diagnosis.
FIG. 3B shows a graph of total PTSD symptoms (PSS total, y axis) differentially associated with rs2267735 genotypes, in females (p<0.001).
Figure 3C:
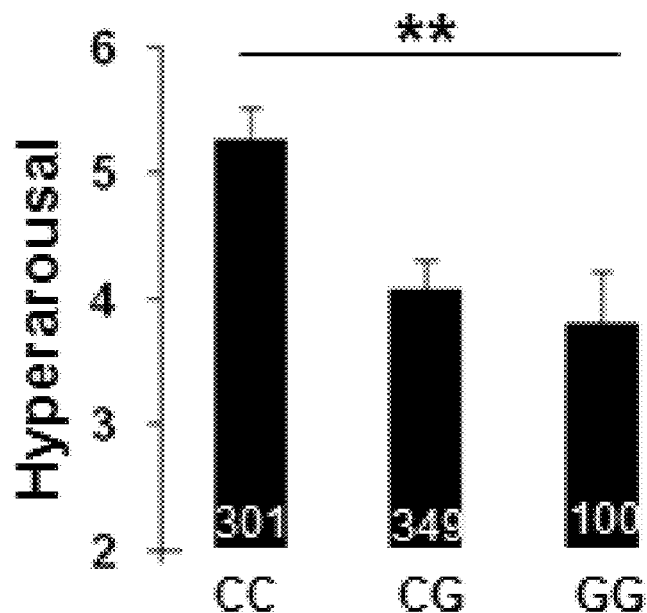
FIG. 3C shows a graph of hyperarousal symptoms (y-axis), the PTSD subscale symptoms, most differentially associated with rs2267735 genotypes (p=0.0009).
Figure 3D:
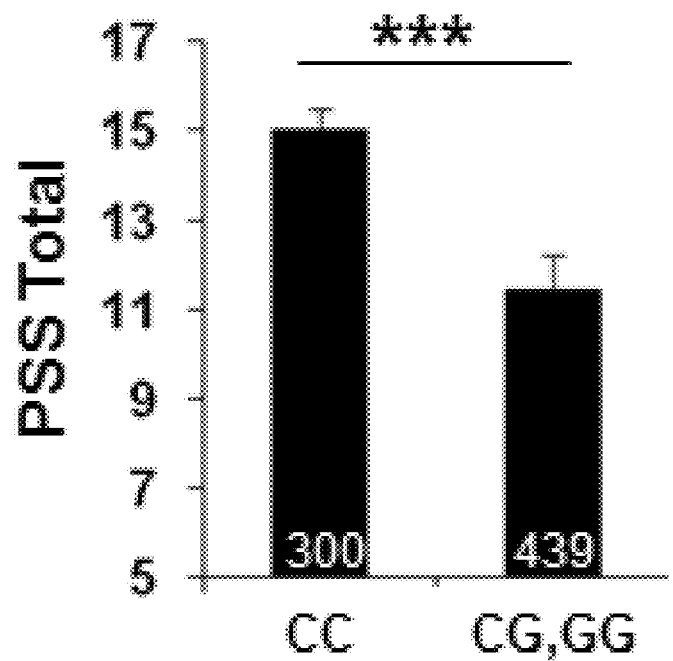
FIG. 3D shows a graph of a dominant/recessive model, indicating that even after controlling for childhood trauma, adult trauma, and age, genotype predicts total PTSD symptoms (p<0.001).

It was next determined if the association between rs2267735 and PTSD diagnosis may be replicated in an additional 439 subjects. These subjects were from the same overall study, but were interviewed and had DNA collected after the original discovery population. Thus they served as a replication source from the same population but distinct in time and with different interviewing staff. The table in FIG. 3A shows the logistic regression results for males and females separately in the initial population described in the tag-SNP analysis, the replication sample from the same population, and the combined sample of 1237 individuals. The main effect of the SNP on PTSD diagnosis could be replicated in women (p<0.05) and combining both samples increased the significance of the association (N=763, p<0.00002). As in the discovery sample, no effects were observed in males (male combined sample N=474, p=0.7).

Example 4

Given the gender differences observed above, the distribution of estrogen response elements (EREs) within ADCYAP1R1 gene was also examined (Table 4). A 65 kb region (chr7:31084099-31149140; GRCh37/hg19) spanning ADCYAP1R1 was used in MatInspector (Matrix Family Library Version 8.2; Genomatix Software GmbH, Munich, Germany) to detect predicted estrogen response elements (EREs). Core similarity and matrix similarity scores are reported for each predicted ERE. In addition, it was noted whether or not a SNP is located within the sequence (Table 4). Core similarity refers to the degree of similarity within the core sequence. The core sequence consists of the highest conserved, consecutive positions within the whole sequence. In FIG. 2 the core sequence is represented by capitalized bases. The matrix similarity score takes into account the conservation across the entire sequence such that mismatches in highly conserved positions of the matrix decrease the matrix similarity more than mismatches in less conserved regions. The maximum core similarity of 1.0 is only reached when the highest conserved bases of a matrix match exactly in the sequence. Matrix similarity scores above 0.80 are considered "good" matches (Cartharius K, et al., Bioinformatics. 21, 2933-42 (2005)). Results showed that rs2267735 is present within a predicted ERE (FIG. 2C, Genomatix; matrix similarity=0.877, core similarity=1.0).

Example 5

Figure 3E:
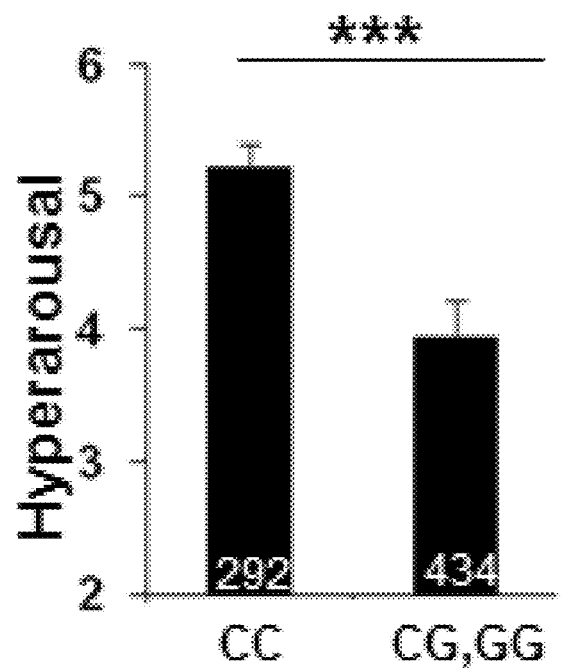
FIG. 3E shows a graph of a dominant/recessive model, indicating that even after controlling for childhood trauma, adult trauma, and age, genotype predicts PTSD hyperarousal symptoms (p<0.0001).

To further examine ADCYAP1R1 rs2267735 SNP associations with continuous PTSD symptom levels in females, both an additive and a dominant model with total PTSD symptoms and symptom subscales using the combined samples (FIG. 3B-E) were examined. The 'CC' allele was most robustly associated with total PTSD symptoms and among subscales, hyperarousal symptoms were the most strongly associated with rs2267735. Notably, even after controlling for childhood trauma history and adult trauma, age and race, (which slightly reduces total N due to missing data) the rs2267735 'CC' allele was associated with higher levels of PTSD hyperarousal symptoms compared to 'G' carriers in women (p=0.0008, FIG. 3E), but not men (p=0.51).

The above analysis was repeated with the 21-item Beck Depression Inventory (BDI) (Beck et al., Arch Gen Psychiatry 4:561-571 (1961)), a commonly used continuous measure of level of depressive symptoms (Beck et al., Clinical Psychology Review 8:77-100 (1988)). For this sample, previously described in Gillespie et al. (Gillespie et al., Depress Anxiety 26, 984-92 (2009)), the BDI had a standardized alpha coefficient of 0.92 (M=10.86, SD=11.71). No associations with these measures and rs2267735 were found.

Example 6

To address whether rs2267735 might be associated with other severe psychiatric illnesses, analyses using bipolar disorder, schizophrenia, and Alzheimer's disease samples were performed.

To test the association of rs2267735 with schizophrenia and bipolar disorder, the genome-wide genotyping data has been produced with the AFFYMETRIX® 6.0 platform for the Genetic Association Information Network (GAIN) schizophrenia and bipolar studies was used. This data is accessible through the National Institutes of Health website. The study accession numbers are phs000021.v3.p2 (schizophrenia) and phs000017.v3.p1 (bipolar disorder). To test the association of rs2267735 with schizophrenia, the available pre-computed analyses in 1378 European ancestry (EA) cases, 1351 EA controls, 954 African American (AA) cases, and 1195 AA controls were used (analysis accession number: pha002857.1 and pha002859.1). For association analyses with bipolar disorder, 1001 EA cases, 1034 EA controls, 363 AA cases, 671 AA controls were available (analysis accession number: pha002858.1 and pha002863.1). All pre-computed p-values for associations of rs2267735 with schizophrenia or bipolar disorder in the two ethnic groups were higher than 0.01, indicating no major contribution of this variant to these disorders.

A significant association of this SNP with these two disorders in subjects with African American (954 cases, 1195 controls) or European (1378 cases, 1351 controls) ancestry was not observed. All pre-computed p-values for associations of rs2267735 with schizophrenia or bipolar disorder were higher than the multiple-testing correction p-value of 0.01, indicating no major contribution of this variant.

Additionally, the association of rs2267735 and Alzheimer's disease in a previously characterized Alzheimer's disease sample was examined. Genomic DNA from Alzheimer's disease samples was prepared using the DNeasy Tissue Kit (Qiagen, cat #: 69504). Genotyping of rs2267735 in an additional Alzheimer's disease cohort was done using TAQ-MAN® assays and a 7900 system (Applied Biosystems, Foster City, Calif.). DNA samples had been previously screened (Corneaveaux et al., Hum Mol Genet 19, 3295-301 (2010)) to eliminate samples with gender errors, poor quality samples (as assessed by low call rates) or whose genotypes did not match reported ethnicity. Samples were obtained from the following sites: Newcastle Brain Tissue Resource (funding via the Medical Research Council, local NHS trusts and Newcastle University); C. M. Morris, MD, Ian G McKeith, Robert H Perry MRC London Brain Bank for Neurodegenerative Diseases (funding via the Medical Research Council); and Simon Lovestone, MD, PhD, Safa Al-Sarraj. MD, Claire Troakes.

In this cohort of 342 subjects, no association with rs226735 and Alzheimer's disease diagnosis using either the additive genetic model (p=0.19) or the dominant/recessive model (p=0.89) was found. Other findings indicate that there is also no association with depression symptoms, substance abuse, Alzheimer's disease, bipolar disorder, and schizophrenia across different samples.

Example 7

Figure 3F:
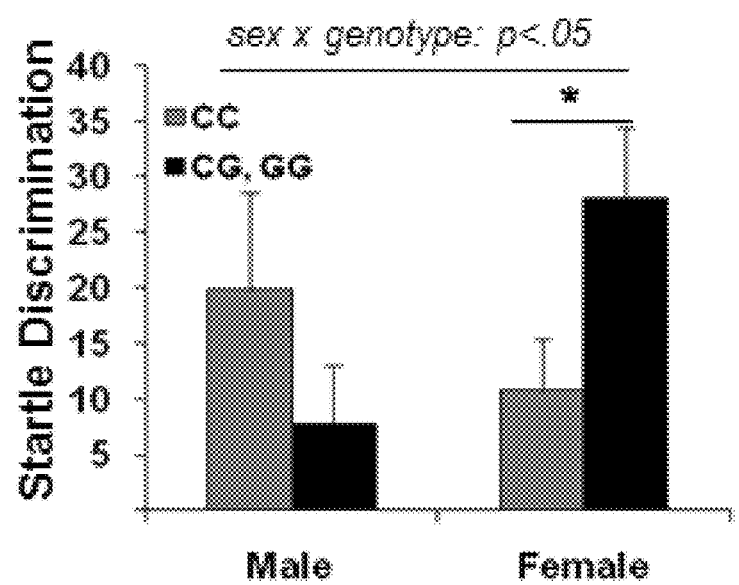
FIG. 3F shows a graph of fear Discrimination (y axis, CS+Startle—CS− Startle) significantly impaired in females with rs2267735 'CC' genotype.

It is known that in PTSD, but not depression, fear response to an inhibitory CS−, or 'safety signal', is exaggerated. To examine whether physiological measures of fear are differentially associated with the ADCYAP1R1 re2267735 SNP, further studies examined whether rs2267735 was associated with impaired fear discrimination late in conditioned acquisition, during the same period noted in FIG. 1E. The discrimination between CS+ and CS− improved across the training procedure in controls, but not in those with PTSD. Females with the 'CC' genotype were significantly less able to discriminate CS+ from CS− signals (FIG. 3F, sex by genotype interaction, p<0.05, and 'CC' vs. 'G' carriers in females, p<0.05).

Example 8

Another set of studies was designed to examined whether a difference in dark-enhanced startle, a measure of increased anxiety in humans that is similar to light-enhanced startle in rodents, was differentially associated with rs2267735. The dark-enhanced startle task included five phases: habituation, light phase 1, dark phase 1, light phase 2, and dark phase 2. The habituation phase consisted of 8 startle probes presented alone at 108 dB (noise-alone trials, NA). Immediately following habituation, participants underwent alternative exposure to the light and dark phases with counterbalanced order of presentation of phases. During each 1-min light and dark phase, participants were exposed to 4 trials of the 108-dB noise probe for a total of 24 trials in the experimental session. Transition from light and dark phases was controlled by a digital timer and there was no perceptible ambient light in the startle booth during the dark phase. Participants were monitored throughout the experiment with the use of a closed circuit camera. In all phases of the experiment, inter-trial intervals were of randomized duration ranging from 9 to 22 seconds.

Figure 3G:
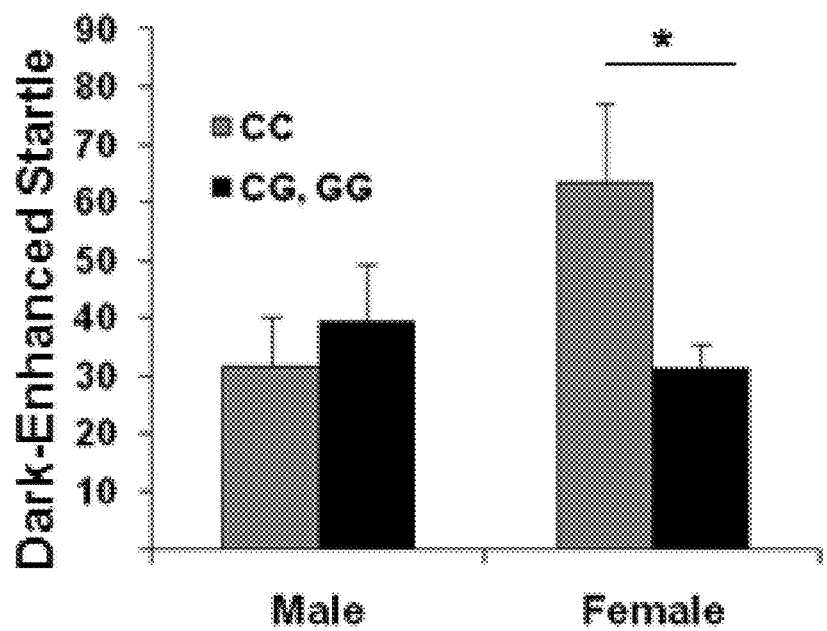
FIG. 3G shows a graph of dark enhanced startle (Startle in Dark—Startle in Light) significantly increased in females with rs2267735 'CC' genotype. N's are shown at base of each bar, bars represent mean±SEM.

Females, but not males, with the 'CC' genotype showed significantly more startle in the dark compared to the light (FIG. 3G, males, N=35, p=0.71; females, N=53, p=0.02).

Example 9

To investigate other mechanisms that may moderate long-term effects of trauma exposure (e.g., genetic and epigenetic mechanisms), DNA methylation of the ADCYAP1R1 gene was investigated. DNA was extracted from peripheral blood at the first site within the ADCYAP1R1 CpG island. For methylation analysis, 700 μl of whole blood was used for DNA extraction using the MagAttract DNA Blood M48 kit (Qiagen, Valencia, Calif.). All DNA for methylation was extracted at the same time and used immediately for bisulfate treatment (refer to Methylation Analyses). DNA concentration was determined by PicoGreen quantitation using the Quant-iT dsDNA Assay Kit (Invitrogen, Carlsbad, Calif.) on a SpectraMax Gemini XPS plate reader (Molecular Devices, Sunnyvale, Calif.). Samples were resolved on a 1% agarose gel to verify that the DNA was of high molecular weight (at least 2 kb). One μg DNA was bisulfite-treated for cytosine to thymine conversion using the EZ DNA Methylation-Gold kit (Zymo Research, Orange, Calif.). The DNA was whole-genome amplified, fragmented, and hybridized to the HumanMethylation27 BeadChip (Illumina, San Diego, Calif.). The XStain was performed on a Tecan Evo 150 liquid handling robot. Individual samples were stratified to BeadChips according to PTSD status to limit bias. The BeadChips were scanned using a BeadStation 500GX, and the methylation level (beta value) was calculated using the Methylation Module of the BeadStudio software.

Samples with probe detection call rates <90% were excluded from further analysis as were those with an average intensity value of either <50% of the experiment-wide sample mean or <2000 arbitrary units (AU). One sample of pooled female DNA was included on each BeadChip as a control throughout the experiment and assessed for reproducibility using a Pearson $R^2$ coefficient. For individual sample I, and CpG site j, the signals from methylated (M) and unmethylated (U) bead types are used to calculate a b value: $\beta_{ij}=M/(U+M+100)$, which can be treated as an approximation of the proportion of CpG dinucleotides methylated at a particular site.

To identify CpG sites for which methylation varied significantly with each outcome, we fit a separate linear mixed effects model for each CpG site. To ensure that our dependent variable was roughly normally distributed, we worked with the log ratio of β-values, log $(\beta/(1-\beta))$. For each CpG site, we regressed log $(\beta/(1-\beta))$ on the variable of interest, as well as sex and age. We included chip-specific random effects to allow for chip-to-chip differences in measurement of the proportion of DNA methylated. We fit the above model for all 27,578 CpG sites.

Figure 8A:
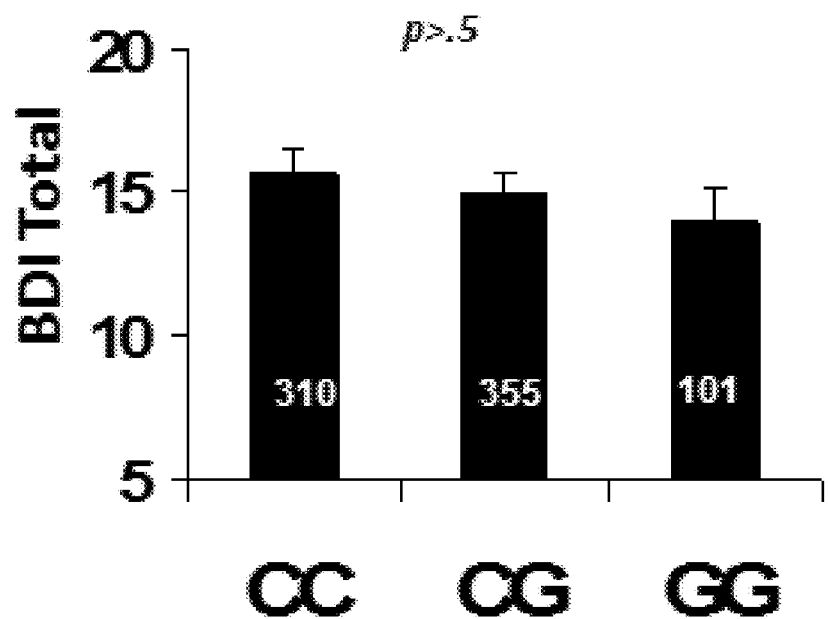
FIG. 8A shows a graph of rs2267735 correlation with depression.
Figure 8B:
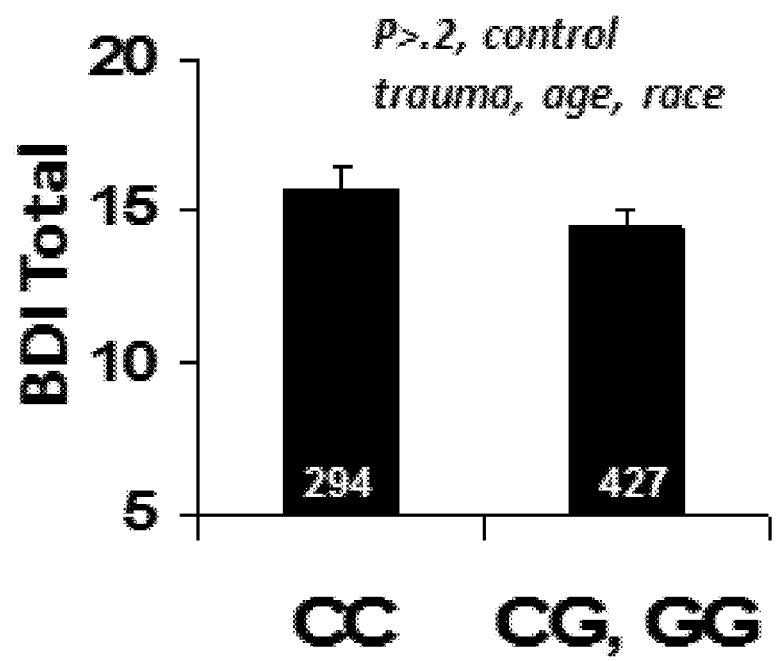
FIG. 8B shows a graph of rs2267735 correlation with depression.
Figure 8C:
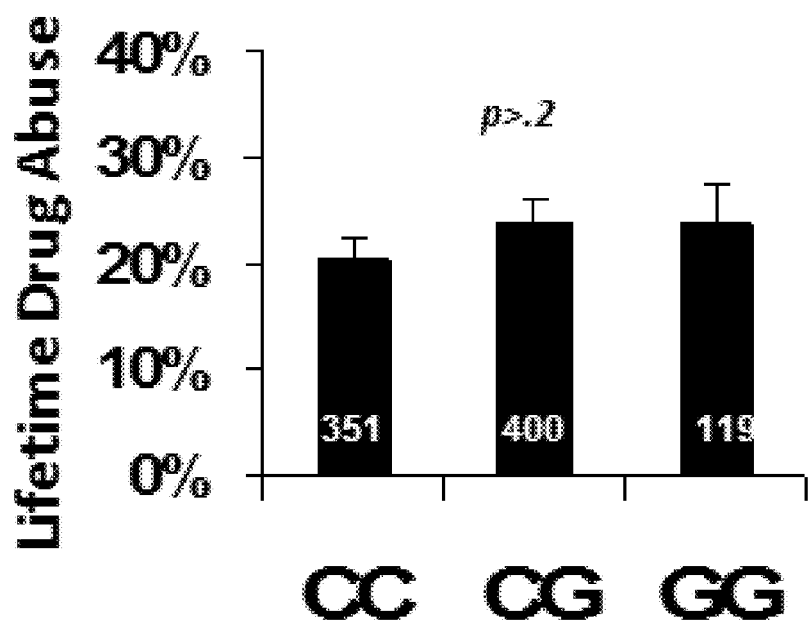
FIG. 8C shows a graph of rs2267735 correlation with drug abuse.
Figure 8D:
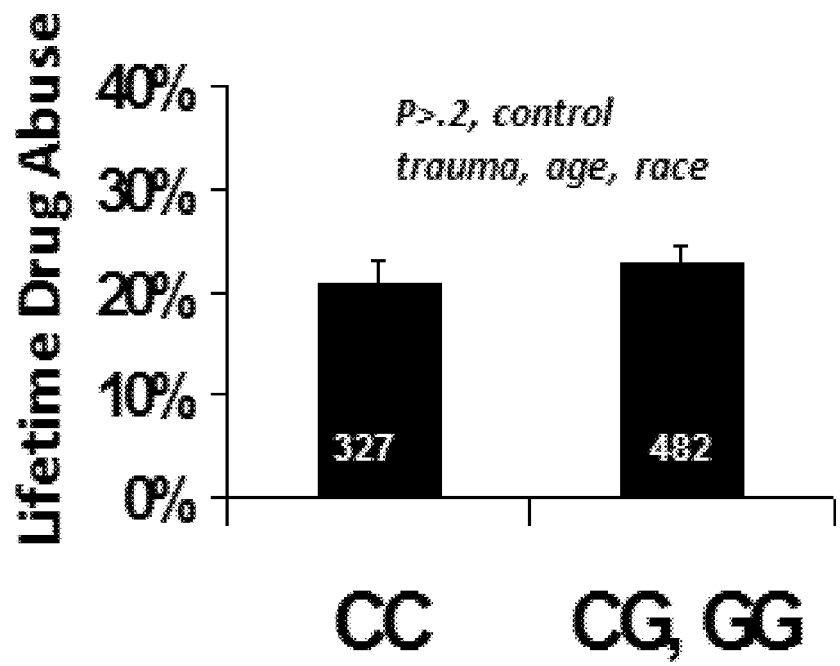
FIG. 8D shows a graph of rs2267735 correlation with drug abuse.
Figure 8E:
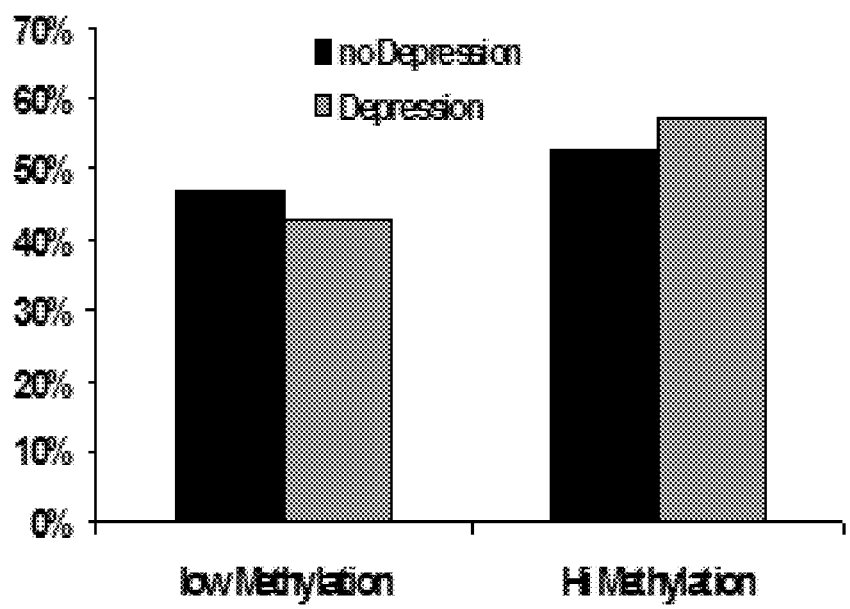
FIG. 8E show a graph of correlation between degree of methylation within the CpG island of the ADCYAP1R1 and depression.

Methylation at the first site within the ADCYAP1R1 CpG island was significantly associated with total PTSD symptoms (FIG. 4A, N=94, r=0.354, p<0.0005) in a sex-independent manner. Further, CpG methylation level (median split) was associated with PTSD diagnosis (FIG. 4B, χ2=8.1, p<0.005), but not depression (p>0.05, FIG. 8E). There was no significant association between methylation of ADCYAP1 and PTSD symptoms.

Example 10

To examine the potential relationship of genotype and brain mRNA expression a brain mRNA expression data set was utilized to test whether ADCYAP1R1 rs2267735 is associated with differential gene expression. Normalized human cortex gene expression data for ADCYAP1R1 and ADCYAP1 in 192 individuals were obtained from dataset previously published in Myers et al., 2007. As shown in FIG. 4C, cortical ADCYAP1R1 and ADCYAP1 mRNA levels were significantly inversely correlated (r=−0.219, p<0.001, including males and females).

Next, prior analyzed genome-wide association and brain mRNA expression data was utilized to examine whether ADCYAP1R1 rs2267735 imputed genotypes were associated with differential ADCYAP1R1 expression in brain. The rs2267735 SNP was not present on the AFFYMETRIX® SNP array used in the Myers et al., Nat Genet 39, 1494-9 (2007) data set and was therefore imputed using genotype data of 18 SNPs within the ADCYAP1R1 locus. Impute version 2.1.0 with 10 burn-in MCMC iterations and a total of 30 MCMC iterations and the HapMap genotype data for the CEU population as a reference was used for imputation of rs2267735 genotypes. rs2267735 genotypes were imputed with an average certainty of 0.852. 99 subjects (42 female and 57 male) had both GWAS data for the imputed rs2267735 SNP and cortex mRNA data for the genotype association with ADCYAP1R1 mRNA levels (FIG. 4D). A sex x genotype effect (FIG. 4D, $F(3,99)=4.3$, $p<0.05$) with females with the 'CC' genotype expressing significantly less ADCYAP1R1 mRNA than males($F(1,33)=5.5$, $p<0.05$) or than females who are 'G' carriers (one-tailed, $F(1, 45)=2.87$, $p<0.05$) was found.

Example 11

To evaluate a role for PACAP signaling in fear conditioning, a mouse Pavlovian fear conditioning test was conducted. This test is a means of studying acute fear and trauma responses that has been proposed to model PTSD. This conditioning paradigm consistently provides robust fear learning in mice leading to changes in gene expression within the amygdala, a region critical for fear learning and expression. Adult male 7-9 week old C57BL/6J mice (Jackson Labs) were used. Mice were housed four per cage in a temperature-controlled (24° C.) animal colony, with ad libitum access to food and water, on a 12-h light-dark cycle, with all behavioral procedures done during the light cycle. All procedures used were approved by the Institutional Animal Care and Use Committee of Emory University and in compliance with National Institutes of Health (NIH) guidelines for the care and use of laboratory animals.

Mice were fear conditioned in eight identical startle response systems (SR-LAB, San Diego Instruments). Each system consisted of a nonrestrictive PLEXIGLAS® cylinder (5.5 cm in diameter and 13 cm long) mounted on a PLEXIGLAS® platform and located in a ventilated, sound-attenuated chamber. Cylinder movements were sampled each millisecond by a piezoelectric accelerometer mounted under each platform. The footshock unconditioned stimulus (US) was generated by a programmable animal shocker (San Diego Instruments) located outside the isolation chambers and was delivered through the cage floor bars. The conditioned stimulus (CS) was a tone delivered by a speaker located about 15 cm above the chambers. Sound intensities were measured by an audiometer (Radio Shack). Stimuli presentation and data acquisition were controlled, digitized, and stored by a Dell computer using SR-LAB software.

After pre-exposure to the conditioning chambers, mice were placed in the chamber, and after 5 min presented with ten tone-shock pairings at an inter-trial interval (ITI) of 3-5 min. Each pairing consisted of a 30 s tone (6 kHz, 85 db, CS) that terminated with a 0.5 s footshock (1.0 mA, US). Freezing in startle-reflex chambers during fear acquisition was assessed as described previously (Choi et al., Proc Natl Acad Sci USA 107(6): 2675-80 (2010); Maguschak et al., Nat Neurosci. 11(11):1319-26 (2008)). Two hours after training, mice were sacrificed, brains rapidly dissected and placed in ice cold phosphate buffered saline, and amygdala or prefrontal cortex tissue removed using a micropunch form 2 mm coronal sections.

Total RNA was prepared from frozen amygdala and prefrontal cortex dissections in mice. Briefly, tissue samples were homogenized and centrifuged at 13,000 g for 3 minutes. RNA was washed with 70% ETOH and purified using RNEASY® columns (Qiagen). RNA amount and quality were determined using a nanodrop spectrophotometer.

140 µg of total RNA were reverse transcribed using the RT2-First Strand Kit (C-03, SA Biosciences). Quantitative PCR was performed using the Applied Biosystems 7500 Fast Real-Time PCR System. Online detection of reaction products was carried out using the TAQMAN® Gene Assay for mouse ADCYAP1R1 (Applied Biosystems, Assay ID: Mm01326453 m1) and for GADPH (Applied Biosystems) and the TAQMAN® Standard Universal Master mix (Applied Biosystems) according to manufacturer's instructions. Calculated values are presented as mean+/−SEM to indicate accuracy of measurement. ADCYAP1R1 values were normalized for measurements of GADPH. PCR conditions were 2 min at 50° C., 10 min at 95° C. and 40 cycles with 15 s 95° C., 60 s 60° C.

The fourth trial of the fear conditioning session demonstrated the most variance with regards to freezing across animals, thus that trial was chosen to examine the rate of acquisition compared to the levels of amygdala and mPFC ADCYAP1R1 gene expression levels. Bivariate correlations were used to demonstrate a significant relationship between level of freezing at trial 4 and level of ADCYAP1R1 gene expression post-training. Note that a significant relationship was also found of the trial 4–trial 1 freezing levels used (essentially the slope of rate of acquisition).

Figure 5A:
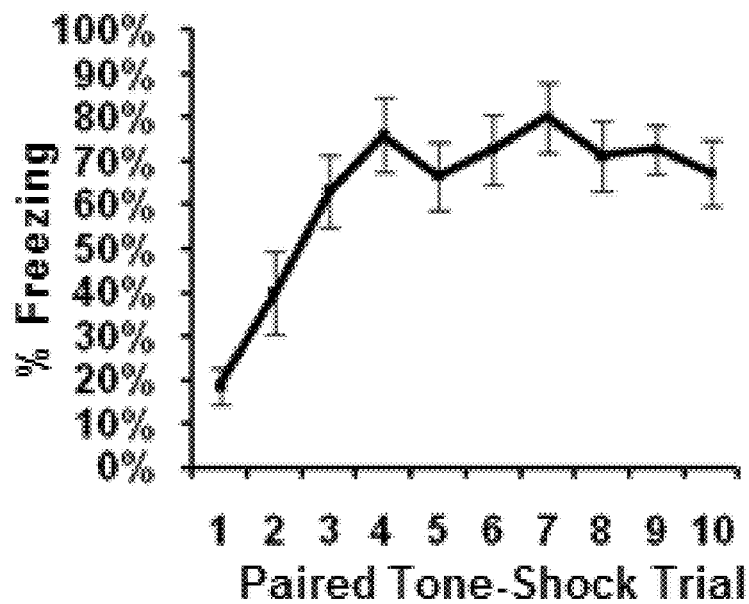
FIG. 5A shows a graph of percentage of time freezing, in mice, to the conditioned tone (CS+) following CS-US pairings (x-axis, conditioning trials 1-10) during the conditioned fear acquisition.
Figure 5B:
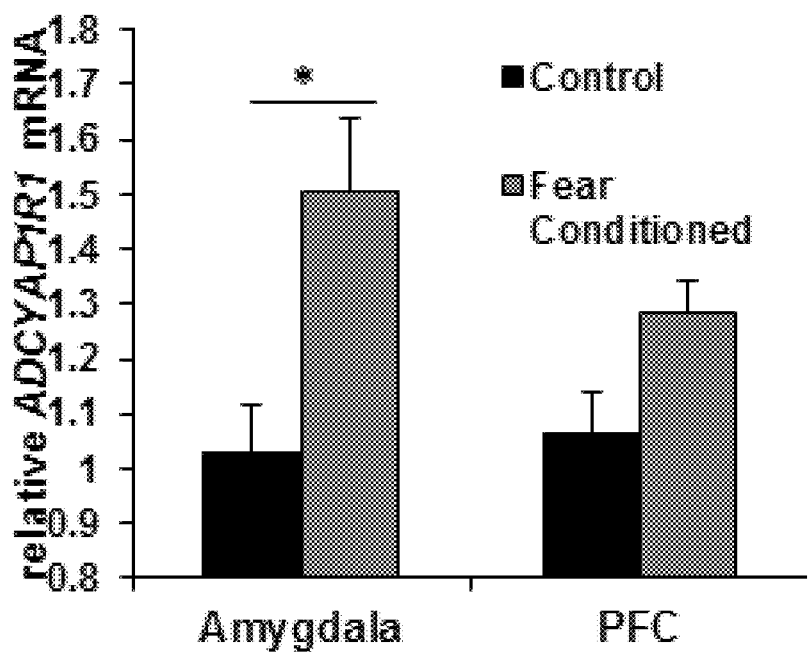
FIG. 5B shows a graph of rtPCR quantitative analyses of mRNA levels within the mouse amygdala and mPFC examined in the same mice as in FIG. 5A at 2 hrs following fear conditioning or in control handling conditions. There was a significant increase in amygdale expression (N=15, 1.47 fold, p<0.05) of ADCYAP1R1 mRNA following fear conditioning relative to control conditions. There was a non-significant trend towards an increase in mRNA within the mPFC (1.19 fold change).
Figure 5C:
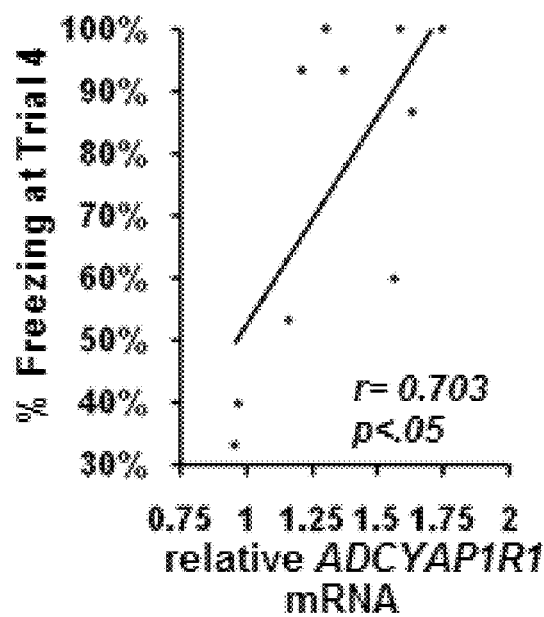
FIG. 5C shows a graph of correlation between average amygdala and PFC ADCYAP1R1 mRNA and % freezing at trial 4, demonstrating that ADCYAP1R1 in amygdala is associated with rate of fear learning (r2=0.49, p<0.05).

Quantitative PCR analyses shows that amygdala ADCYAP1R1 mRNA increased ~1.5-fold during the consolidation of fear (FIG. 5B, $p<0.05$), with a similar trend within the mPFC. When peak freezing was compared with brain mRNA levels, a significant correlation between fear learning and ADCYAP1R1 mRNA (FIG. 5C, $r2=0.49$, $p<0.05$) was found.

Example 12

To establish the relationship between PACAP/PAC1 receptors and estrogen in a validated model of sex hormone regulation, estrogen-induced changes in ADCYAP1 and ADCYAP1R1 transcripts in the bed nucleus of stria terminalis (BNST) in female rats was examined. The BNST is a component of the extended amygdala that is subject to significant gonadal hormonal control. In rodents, it is critical for emotional behavior, mediating stress responses and the light-enhanced startle response. Quantitative PCR was performed (Hammack et al., *Psychoneuroendocrinology* 34, 833-43 (2009); Girard et al., *J Neurochem* 99(2): 499-513 (2006); Braas et al., *Peptides* September 28(9):1856-70 (2007)). Rats were implanted with 21-day continuous release pellets for delivery of estrogen. After rat euthanasia, the different brain regions were quickly dissected and frozen on dry ice. The tissues were homogenized in Stat-60 total RNA/mRNA isolation reagent (Tel-Test "B", Friendswood, Tex.). The RNA (2 µg) was used to synthesize first strand cDNA using SUPERSCRIPT® II reverse transcriptase and random hexamer primers with the SUPERSCRIPT® II Preamplification System (Invitrogen, Carlsbad, Calif.) in a 20 µl final reaction volume. The same tissue regions from all rats were reverse transcribed simultaneously to obviate variability. Following the reverse transcriptase reaction, the cDNA samples were treated with RNase H to remove residual RNA. Real-time quantitative PCR methods and oligonucleotide primers were exactly as described previously. The melting profiles for amplified DNA fragments were performed to verify unique product amplification in the quantitative PCR assays. For each target sequence, all samples from the same brain region were amplified together in the same assay to minimize variability. All data were normalized to 18S RNA levels; all assays were repeated 2-3 times to verify data reproducibility.

Figure 5D:
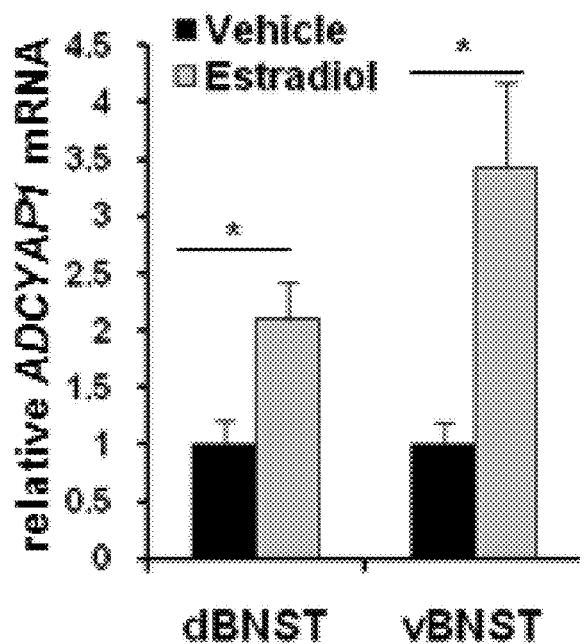
FIG. 5D shows a graph of ADCYAP1 transcripts quantified in rat bed nucleus of the stria terminalis (BNST) involved in stress in female rats (N=12/group) that had been ovarectomized and replaced with estradiol implants vs. sham vehicle implants. ADCYAP1 transcripts were significantly increased in both dorsal (2.1-fold) and ventral (3.4-fold) BNST after estradiol implantation.
Figure 5E:
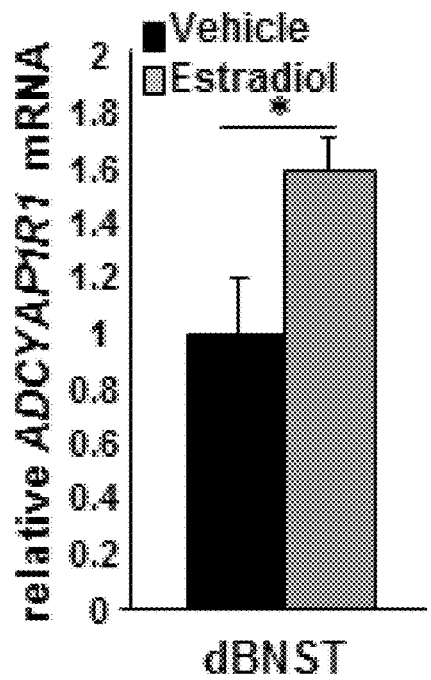
FIG. 5E shows a graph of ADCYAP1R1 transcripts significantly increased in dorsal (1.6-fold, N=4 per group) BNST after estradiol implantation.

Compared to control implants, estradiol increased ADCYAP1 transcripts in the dorsal and ventral BNST 2.1- and 3.4-fold, respectively (p<0.01, FIG. 5D) in the BNST in ovarectomized (OVX) female rats following 21-day implantation of continuous release estrogen pellets. Additionally, estradiol increased ADCYAP1R1 mRNA 1.5-fold in the dorsal BNST samples (p<0.05, FIG. 5E).

All statistical analyses were done in SPSS version 17.0. Levels of PACAP38 were analyzed relative to PTSD total symptoms and subscales (defined in PTSD Symptom Scales section) using Univariate ANOVA. PACAP38 measures were divided into two levels, designated as high (N=33; >20.8 pM) and low (N=32; <20.4 pM), at the median. These values were analyzed by sex (FIG. 1B-E). The correlation, using bivariate correlation analyses, between all PACAP38 measures and the total PTSD symptoms is shown in FIG. 1A (significant at p<0.005, r=0.497). Additionally, the correlation analysis between mRNA levels for ADCYAP1 and ADCYAP1R1 reveals an inverse and significant relationship (FIG. 4C; p=0.001, r=0.276).

Given the relationship between PACAP38 and PTSD, primary goal for statistical analysis was to determine if genetic variants in either ADCYAP1 or ADCYAP1R1 have an effect of PTSD symptoms. Furthermore, another goal was to determine if such a relationship was sex dependent. Genotypes were recoded into categorical variables representing each of the three genotypes. Missing data was designated as missing in the system so that it would be excluded from the analysis. A logistic regression with PTSD coded as a dichotomous variable for either having or not having PTSD (defined in PTSD Symptom Scale) against each of the tag-SNPs was conducted. The –log (p) values were calculated and graphed in the physical order of the tag-SNPs along the chromosome (FIG. 2A and FIG. 6). This analysis was repeated selecting cases by sex. SNPs that passed bonferroni correction for 44 SNPs at p<0.0011 (–log (p)>3.0) were examined further.

Only rs2267735 passed the criteria for further analysis. Genetic demographics (Table 1) were calculated using a dataset pared-down to include only those samples with genotypes for rs2267725. Variables suspected to have an impact on PTSD symptoms are described, relative to PTSD diagnosis, in Tables 1-2 (Initial Genetic Sample'). The same was done for PACAP demographics paring-down to only those samples that had measurements for PACAP38 (Tables 1-2; N=64, 'PACAP Blood Sample').

ADCYAP1R1 SNP rs2267735 was coded as a dichotomous variable representing a dominant model for the more rare allele. Using Univariate ANOVA, both the three level categorical genotypes and the two level categorical genotypes were analyzed relative to PTSD and the subscales, controlling for total trauma (child and adult), age and race (data only shown for original plus replication sample set; FIGS. 3B-3E). Univariate ANOVA was also used to determine if rs2267735 has an indirect impact on PTSD by effecting either depressive symptoms or drug abuse (FIGS. 8A-8D). There was no statistical difference in either BDI total or lifetime drug abuse relative to the genotype at rs2237735. These variables were subsequently removed from regression models. Similar analyses were done for PTSD by startle measures and mRNA levels (FIG. 1E, FIGS. 3F, 3G, FIG. 4D and FIG. 5).

Figure 4A:
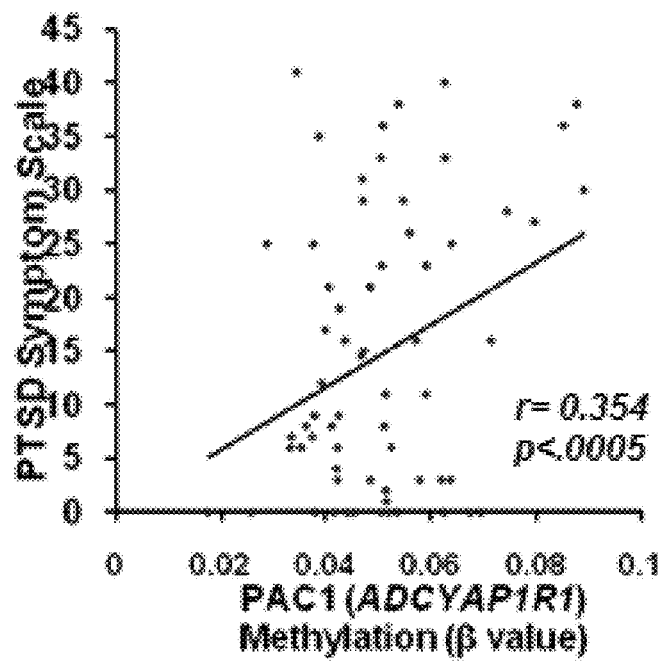
FIG. 4A shows a graph of methylation within the CpG island of the ADCYAP1R1 gene (beta value, Illumina #cg27076139) positively correlated with PTSD symptoms in both sexes (N=107; r=0.336, p<0.0005).
Figure 4B:
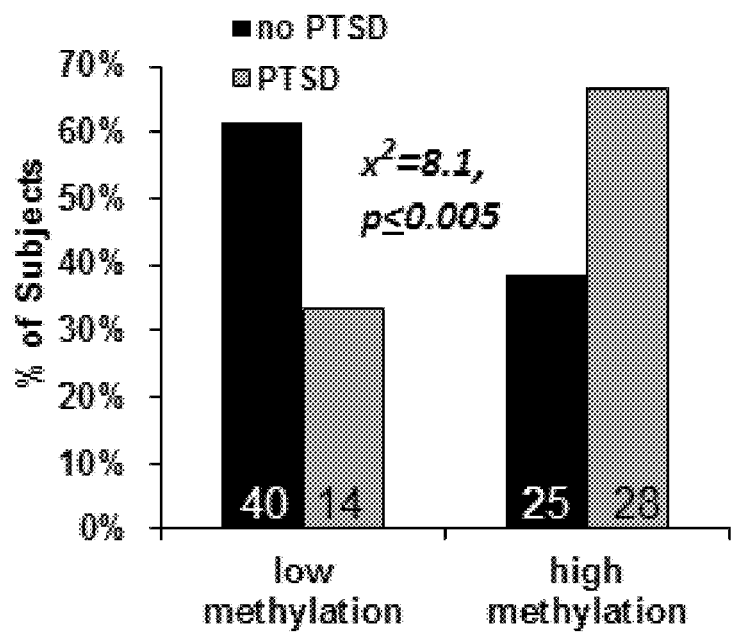
FIG. 4B shows a graph of subjects with PTSD having higher levels of ADCYAP1R1 methylation (based on median split, N=107; chi-squared analyses, p<0.005).
Figure 4C:
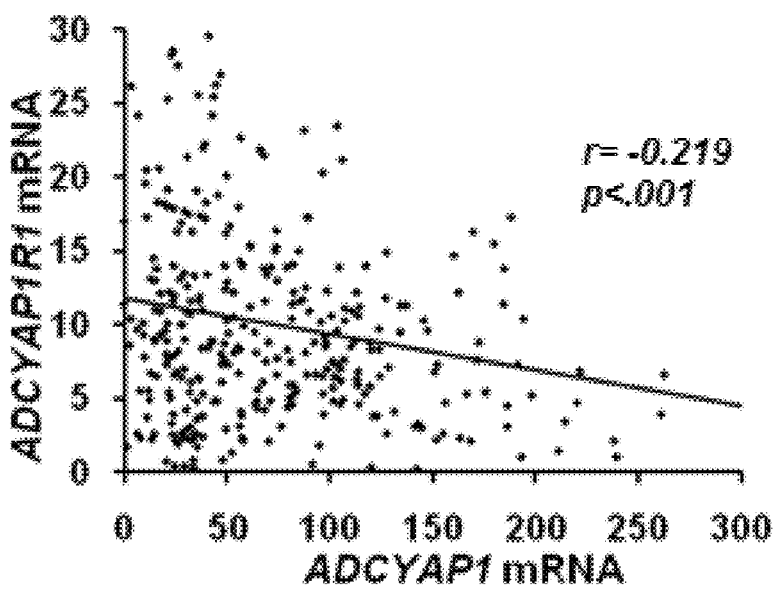
FIG. 4C shows a graph indicating that ADCYAP1 mRNA levels are significantly and inversely correlated with ADCYAP1R1 mRNA levels in cortex (from prior dataset13) (r=−0.219; p<0.001).
Figure 4D:
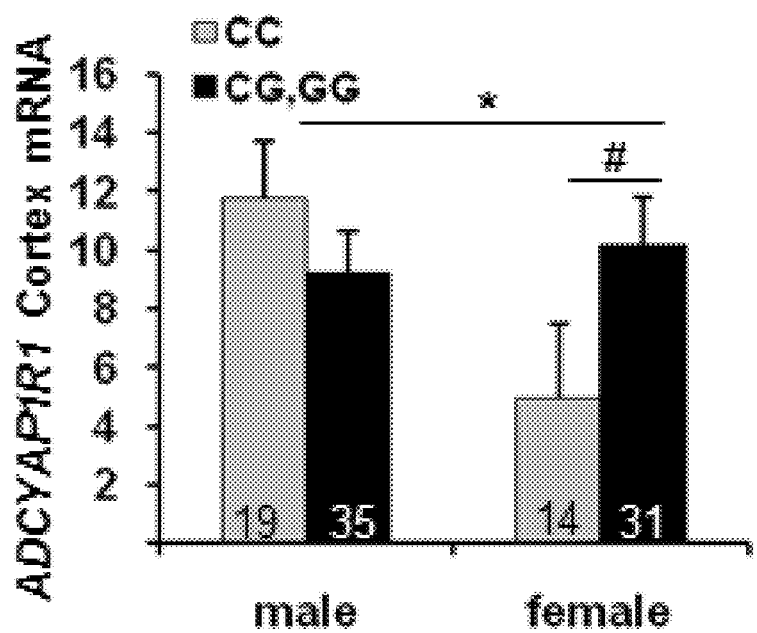
FIG. 4D shows a graph indicating that ADCYAP1R1 mRNA levels are differentially expressed in females compared to males based on imputed ADCYAP1R1 rs2267735 genotype (from prior dataset13)(*p<0.05 male vs. female CC carriers, # p<0.05, one-tailed analysis of CC vs G-carriers within females).

Correlation with a two-tailed test was used to examine the relationship between the beta values for methylation by PTSD total symptoms (FIG. 4A). The data were then spit by high and low methylation (high, N=50; low, N=45) and analyzed by a dichotomous variable, PTSD diagnosis, using Chi-square (FIG. 4B).

Example 13

Based on the findings described above, the experiments described herein were designed to investigate the role of PACAP in mediating the consequences of repeated stress.
Methods Adult male Sprague-Dawley rats (250-275 gm) were obtained from Charles River Laboratories (Wilmington, Ma). After delivery, rats were allowed to habituate in their home cages for at least one week before experimentation. Rats were single-housed and maintained on a 12-hour light/dark cycle (lights on at 07:00 h). Food and water were available ad libitum. All procedures were approved by the Institutional Animal Care and Use Committee at the University of Vermont.

For acute infusion studies, rats were anesthetized with isoflurane vapor and secured in a stereotaxic apparatus. After skin incision, the skull was exposed and four screws were inserted to provide skullcap stability. Two stainless steel cannulae (26 gauge, Plastics One, Roanoke, Va.) were lowered at a 20 degree angle just above the anterolateral bed nucleus of the stria terminalis (BNST), from bregma in mm; AP=–0.3, ML=±3.8 and DV=–5.3 from the surface of the dura. A skullcap was created with dental cement to hold the cannulae in place. One week after cannulation, the rats were acutely infused bilaterally into the BNST with PACAP38 (American Peptide Co., Sunnyvale, Calif.; 0.1, 0.5 or 1 µg in 0.5 µl) or saline/bovine serum albumin (BSA) vehicle; the infusion cannulae were left in place for 1 min before removal.

Similar procedures were followed for chronic infusions. Once the BNST cannulae (Plastics One, Roanoke, Va.; No. 328OP/SPC) and skullcap were in place, the cannulae were attached to a single bifurcation connector (Plastics One, Roanoke, Va.; No. 21y) using 3 mm catheter tubing (Alzet, Cupertino, Calif.: OC 1.14 mm, ID 0.69 mm). The bifurcation connector was attached to 6.7 cm of catheter tubing attached to a mini-osmotic pump (Alzet, Cupertino, Calif.; No. 2002, 200 µl volume, 0.5 µl/h) containing either antagonist PACAP(6-38) (American Peptide Co., Sunnyvale, Calif.; 75 µM) or vehicle (0.05% BSA in saline). Long term PACAP(6-38) stability at 37° C. was assessed separately by daily aliquot removal for intact and amidated peptide radioimmunoassays. Peptide loss was 4%/day; final minipump PACAP(6-38) concentration at the end of the study was approximately 40 µM. All catheters were filled with vehicle to delay antagonist infusion into the BNST before the repeated variate stress procedure. The minipumps were primed according to manufacturer's instructions and secured subcutaneously in the interscapular space. The rats were returned to their home cages for 6 day postsurgical recovery; all rats were monitored for food/water intake and weighed daily.

Following acclimation or postsurgery recovery, each animal was randomly assigned to either a control or chronically stressed group. Control group animals remained in their home cages until euthanasia. The stressed group of animals underwent a repeated variate stress paradigm in which rats were exposed to one of five different stressors (oscillation, forced swim, restraint, pedestal standing and footshock) each day for seven days, as described previously (Hammack et al., *Psychoneuroendocrinology* 34:833-843 (2009)). All animals within the group were exposed to the same order of stressors for the same duration.

Behavioral testing was performed one day after the last stressor. Rats were placed individually into a 55×55 cm opaque white arena with 50 cm walls (United States Plastics Corp., Lima, Ohio). A novel object (blue thermos cup) was secured to the center of the chamber and the rats were allowed to move freely for 5 min. Illumination was 14 lux. The sessions were captured digitally, and the amount of time the rat either spent actively touching the object or approached the object within 3 mm of its nose was tabulated.

A plus maze of black painted wood and elevated 74 cm from the floor consisted of two opposing open and two opposing closed arms (each arm 60 cm long and 9 cm wide), which extended perpendicularly from a central square platform (9×9 cm). The lengths of the closed arms were walled by black opaque panels 30 cm in height. Illumination with a red bulb was at 6 lux. The animals were individually placed on the central platform facing a closed arm and allowed to freely explore the maze for 7 min. The sessions were captured digitally, and the time spent in the open and closed arms and the total number of crosses into the open arms were scored. In all behavioral tests, the activities were tabulated by observers blinded to the experiment.

Upon completion of behavioral testing, the rats were deeply anesthetized and perfused transcardially with saline followed by 4% paraformaldehyde. The brains were removed, fixed for an additional 24 hours, washed and cryoprotected through graded sucrose solutions (30% sucrose final). The brains were blocked and frozen in TISSUE-TEK® medium for cryosectioning (30 µm); all slides were processed for cresyl violet staining, and cannulae placements were verified under brightfield microscopy. Rats with cannulae placements in the body of the caudate-putamen or lateral septum were not included in the studies. Anterolateral BNST infusion spread was verified in select animals by cannulae injection with dextran conjugated Texas Red (Molecular Probes/Invitrogen, Carlsbad, Calif.; 2.5 mg/ml) at experiment termination and tissue visualization under fluorescent microscopy.

Quantitative PCR was performed exactly as described previously (Girard et al., *Regulatory Peptides* 109:89-101 (2002); Girard et al., 2006; Hammack et al., 2009). Briefly, after euthanasia by rapid decapitation, the coronal rat brain sections were prepared using a rodent brain matrix (Ted Pella, Inc. Redding, Calif.). The different brain regions were quickly dissected and frozen on dry ice for total RNA extraction using STAT-60 RNA/mRNA isolation reagent (Tel-Test "B", Friendswood, Tex.). All RNA from same brain regions were reverse transcribed simultaneously using random hexamer primers with the SuperScript II Preamplification System (Invitrogen, Carlsbad, Calif.) to obviate variability. Real-time quantitative PCR was performed as described using SYBR Green I detection (Girard et al., 2002; Girard et al., 2006; Hammack et al., 2009). Briefly, cDNA templates were diluted 5-fold to minimize the inhibitory effects of the reverse transcription reaction components and assayed on an ABI Prism 7500 Fast Real-Time PCR System (Applied Biosystems, Foster City, Calif.) using SYBR Green I JUMPSTART™ Taq ReadyMix (Sigma, St. Louis, Mo.) containing 3.5 mM $MgCl_2$, 200 µM dATP, dGTP, dCTP and dTTP, 0.64 U Taq DNA polymerase and 300 nM of each primer in a final 25 µl reaction volume. Oligonucleotide primer sequences were:

```
                                   (SEQ ID NO: 7)
PACAP (S)    5'-CATGTGTAGCGGAGCAAGGTT-3';

(SEQ ID NO: 8)
PACAP (AS)   5'-GTCTTGCAGCGGGTTTCC-3';

(SEQ ID NO: 9)
CRH (S)      5'-TGGATCTCACCTTCCACCTTCTG-3';
and
                                   (SEQ ID NO: 10)
CRH (AS)     5'-CCGATAATCTCCATCAGTTTCCTG-3'.
```

The melting profiles for amplified DNA fragments were performed to verify unique product amplification in the quantitative PCR assays. For data analyses, a standard curve was constructed by amplification of serially diluted plasmids containing the target sequence (Girard et al., 2002; Girard et al., 2006). The increase in SYBR Green I fluorescence intensity ($\Delta R_n$) was plotted as a function of cycle number, and the threshold cycle ($C_T$) was determined by the software as the amplification cycle at which the $\Delta R_n$ first intersects the established baseline. The transcript levels in each sample were calculated from the $C_T$ by interpolation from the standard curve to yield the relative changes in expression. For each target sequence, all samples from the same brain region were amplified together in the same assay to minimize variability. All data were normalized to 18S RNA levels; all assays were repeated 2-3 times to verify data reproducibility.

For immunocytochemical analyses, rats were anesthetized with pentobarbital 24 hours after the last stressor (day 8) and perfused transcardially with heparinized saline followed by 4% paraformaldehyde. The brains were quickly removed, postfixed and protected in 30% sucrose for cryosectioning (30 µm). For BNST staining, tissue sections from control and stressed animals were matched using the anterior commissure and fornix as landmarks. For CeA staining, the sections were matched based on position and dimension of the optic tracts.

All immunocytochemistry reagents were chosen to permit PACAP and corticotropin releasing hormone (CRH) colocalization studies. Brain cryosections were permeabilized with 0.3% triton X-100, treated with 1% BSA blocking solution and incubated in a mouse monoclonal PACAP antibody (1:10; Jens Hannibal, Bisperg Hospital, Copenhagen, Denmark) and/or a rabbit affinity-purified CRH antibody (1:100; Phoenix Pharmaceuticals, Burlingame, Calif.) 48 hours at 4° C. The monoclonal antibody was directed to the N-terminus of PACAP and did not discriminate between PACAP27 and PACAP38. PACAP localizations were performed using tyramide amplification as previously described (Fahrenkrug and Hannibal, *Neuroscience* 83: 1261-1271

(1998)). After primary antibody incubation and washings, the cryosections were incubated in biotinylated horse anti-mouse IgG (1:200; Vector Laboratories, Burlingame, Calif.) for 2 hours. The sections were washed, treated with strep-avidin horseradish peroxidase (HRP; 1:250) for 30 min, washed again and subsequently incubated in a tyramide-biotin reagent (1:100; Perkin Elmer, Boston, Mass.) for 10 min. After extensive buffer rinses, the PACAP immunoreactivity in the sections was localized using avidin-conjugated Cy2 (1:200; Jackson ImmunoResearch, West Grove, Pa.). For CRH localizations, the cryosections were incubated in Cy3-conjugated donkey anti-rabbit IgG (1:250; Jackson ImmunoResearch, West Grove, Pa.). In some studies, the distribution of the PACAP immunocytochemical staining patterns was identified using the avidin-biotin-complex (ABC; Vector Laboratories, Burlingame, Calif.) technique. Following tyramide amplification, the sections were incubated with 1:200 ABC solution for 2 hours, washed and processed using diaminobenzidine (DAB) and hydrogen peroxide as substrates. To obviate fluorochrome signal occlusion in these dual localization studies, the cryosections with CRH localizations using Cy3 were imaged first; the sections were subsequently returned to the immunocytochemical process for PACAP staining using DAB. To compare CRH (Cy3) and PACAP (DAB) staining patterns on the same tissue sections, images of the PACAP DAB patterns were digitally extracted and superimposed onto the CRH immunofluorescence image with the aid of CNS structures as landmarks. All antibody staining was blocked with their respective blocking peptides. Omission of any one of the processing reagents also failed to produce signals.

In situ hybridization for PACAP transcripts was performed as described (Brandenburg et al., 1997; Braas and May, *J of Biol Chem* 274: 27702-27710 (1999)). After anesthesia, control and chronically stressed rats were euthanized by decapitation. The brains were rapidly removed and frozen; cryosections (20 μm) were mounted onto Superfrost Plus slides and stored at −80° C. before processing. The cryosections were fixed in 4% paraformaldehyde, acetylated, and chloroform treated before probe hybridization (approximately 500 ng/slide) in a humidified chamber at 45° C. for 24 hours. Sense and antisense PACAP cRNAs were transcribed from linearized plasmids using biotin-labeled UTP. After high stringency washes in 20× saline sodium citrate (SSC) buffer and 0.2×SSC, and RNAse A digestion of residual probe, the cryosections were incubated in strep-avidin-HRP (horseradish peroxidase) for tyramide biotin amplification. The sections were finally incubated with ABC complex for signal detection with DAB.

Quantitative image analyses were performed using NIH ImageJ (Abramoff et al., *Biophotonics International* 11: 36-42 (2004)). After background thresholding, the images were examined by pixel analyses over uniform circumscribed areas. Statistical Student's t-tests and one-way/two-way analysis of variance (ANOVA) were performed using SigmaPlot/SigmaStat (Systat Software, San Jose, Calif.). Weight change data were analyzed by repeated measures ANOVA. All values represent the mean change±SEM. $P<0.05$ was considered significant.

Repeated Variate Stress Selectively Increases PACAP Transcript Expression and Immunoreactivity in the BNST.

Figure 9A:
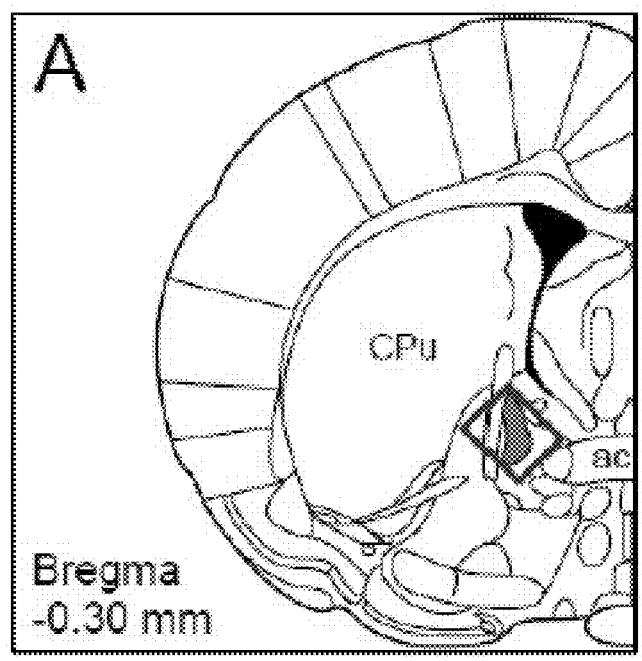
FIG. 9A depicts a coronal section of a brain, wherein the square denotes an area examined for immunocytochemical labeling. Asterisk, significantly different from control at p=0.002.

To identify discrete subregions of BNST PACAP expression, immunocytochemical and in situ hybridization approaches were used to examine PACAP immunoreactivity in the oval nucleus. In the coronal cryosections examined, (bregma −0.24 thru −0.36; FIG. 9), PACAP immunoreactivity in the anterolateral division BNST was high in the BNST oval nucleus. In tissues from control non-stressed animals, the PACAP staining appeared sparse and punctuate. The staining appeared to represent predominantly fiber structures including varicosities and terminals; few cell bodies were identified. Nonetheless, as the soma of BNST neurons are relatively small (15-20 μm) with a thin cytoplasmic rim circumscribing the nuclei, PACAP immunoreactivity in vesicles or Golgi regions could not always be readily distinguished, which may have contributed to their under-representation. In contrast to patterns for PACAP, CRH fiber immunoreactivity in control tissues was dense, intense, and pervasive throughout the oval nucleus. CRH staining in the soma was weaker and not readily identified by these procedures.

Figure 9B:
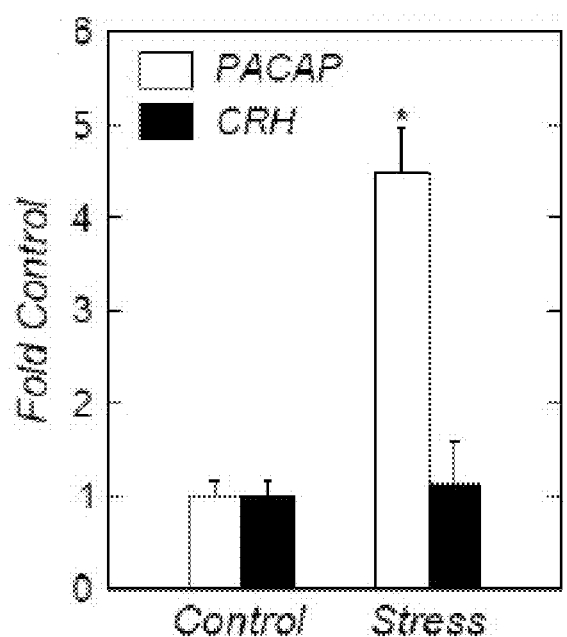
FIG. 9B shows a graph of BNST PACAP immunoreactivity in repeatedly stressed animals and non-stressed control animals. The increase in PACAP immunoreactivity in stressed animals was more than 4-fold above threshold. CRH immunoreactivity was not changed between the two animal groups.
Figure 10A:
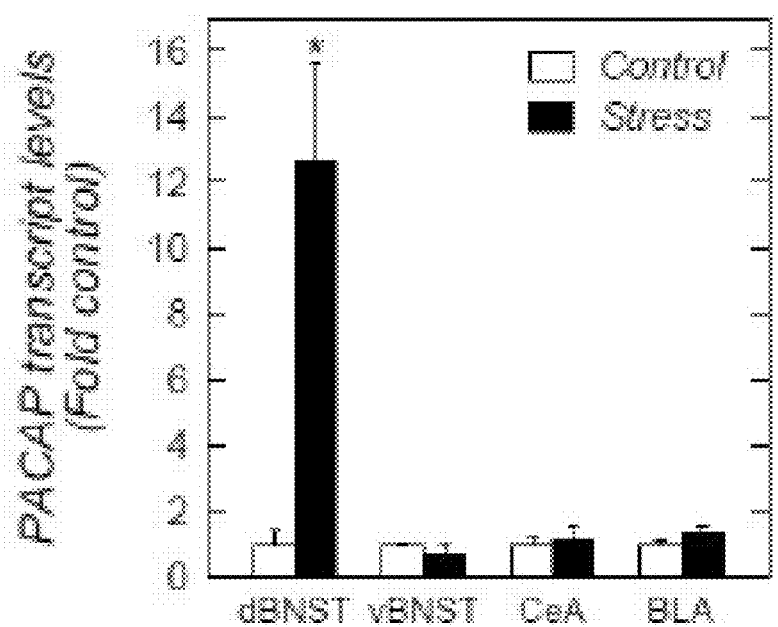
FIG. 10A shows a graph comparing PACAP mRNA transcript levels in the dBNST, cBNST, central amygdala (CeA), and basolateral amygdala (BLA) under stress and control conditions.
Figure 10B:
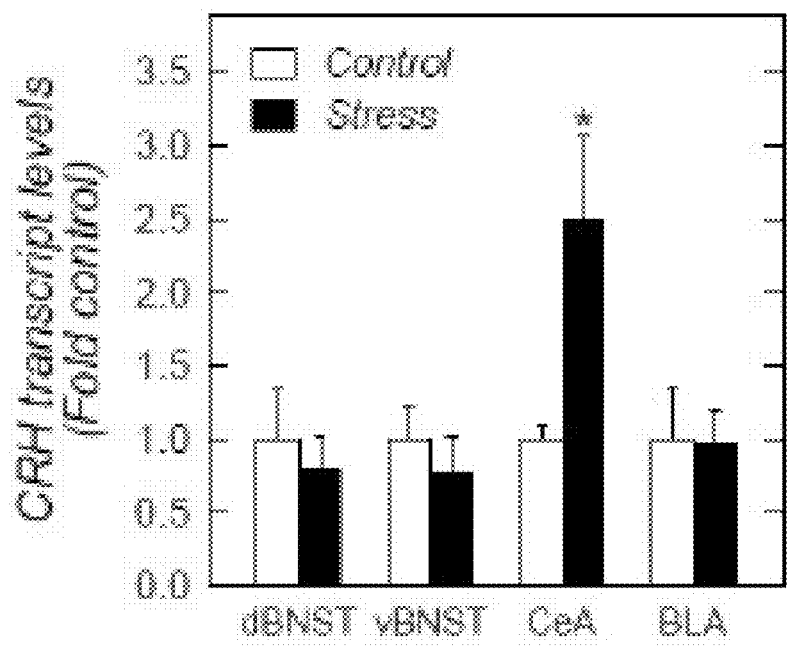
FIG. 10B shows a graph comparing CRH mRNA transcript levels in the dBNST, cBNST, CeA, and BLA under stress and control conditions. n=6, data represent mean fold change+SEM. Asterisk, significantly different at p<0.05.
Figure 10C:
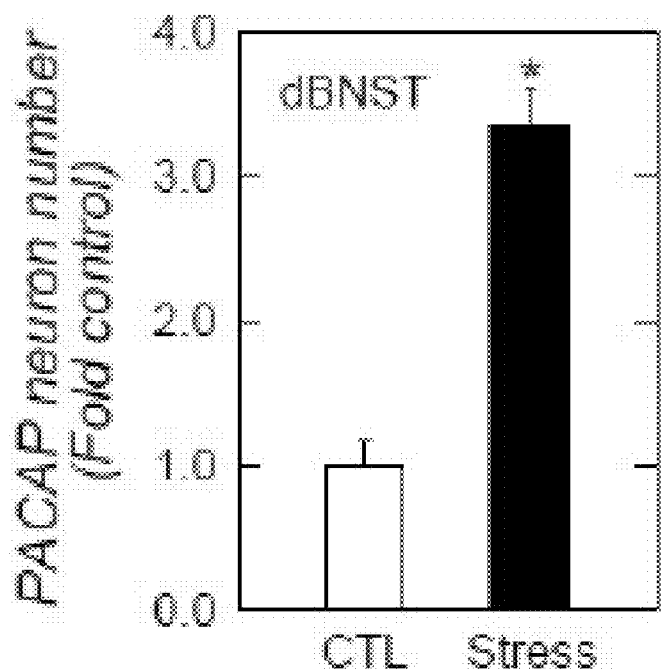
FIG. 10C shows a graph demonstrating that the number of BNST neuronal soma with PACAP labeling was increased in stressed animals compared to controls. n=3, data represent mean+SEM. Asterisk, significantly different from control at p=0.001.

Repeated variate stress selectively increased PACAP immunoreactivity in the oval nucleus. Compared to control non-stressed animals, PACAP immunoreactivity in the stressed group appeared dense and more pervasive throughout the BNST. Repeated variate stress increased PACAP immunoreactivity in the oval nucleus more than 4-fold compared to the control group (FIG. 9B; df=4, t=−7.17, $p<0.002$); CRH immunoreactivity by contrast was not altered by stress (FIGS. 9B-9D; df=4, t=−0.28, p=0.80). Consistent with these data, quantitative PCR measurements for BNST CRH transcript expression did not reveal significant changes between control and stressed animals (FIG. 10B). The PACAP immunocytochemical and quantitative PCR data were further corroborated by in situ hybridization studies. While PACAP mRNA expression was apparent in only a few somal profiles in the oval nucleus of control animals, the number of PACAP expressing neurons was increased significantly after chronic stress (FIG. 10C; df=4, t=−8.35, $p<0.001$).

PACAP and CRH have Distinct Immunoreactive Staining Patterns in the BNST.

To further evaluate the relationships between CRH and PACAP in the oval nucleus, immunocytochemical colocalization studies were performed, and results showed that the two peptides were not localized within the same fiber elements, suggesting that CRH and PACAP represented separate and distinct peptidergic systems in the BNST. In these analyses, it was also apparent that the CRH fiber staining was not uniform across the oval nucleus and associated BNST regions. CRH staining was prominent in the lateral and ventral areas of the nucleus, but relatively sparse in the central area, particularly environs bregma −0.24 where the dimensions of the oval nucleus were maximal. PACAP immunoreactivity was heaviest in this low CRH staining area and this difference was especially evident in the stressed tissues where PACAP expression was induced. As these staining patterns may have reflected differences in PACAP and CRH staining sensitivity, PACAP was then localized using amplification procedures as described above. Even under these enhanced procedures, PACAP immunoreactive staining patterns were distinct from those for CRH. The overlay of PACAP immunoreactivity onto that for CRH again demonstrated that PACAP staining appeared restricted to areas of low CRH density. Unlike the oval nucleus, PACAP and CRH immunoreactivity in the ventrolateral and posterior BNST of control and stressed animals appeared diffuse and poorly defined.

Repeated Variate Stress Selectively Increases CRH Immunoreactivity in the CeA.

Figure 11:
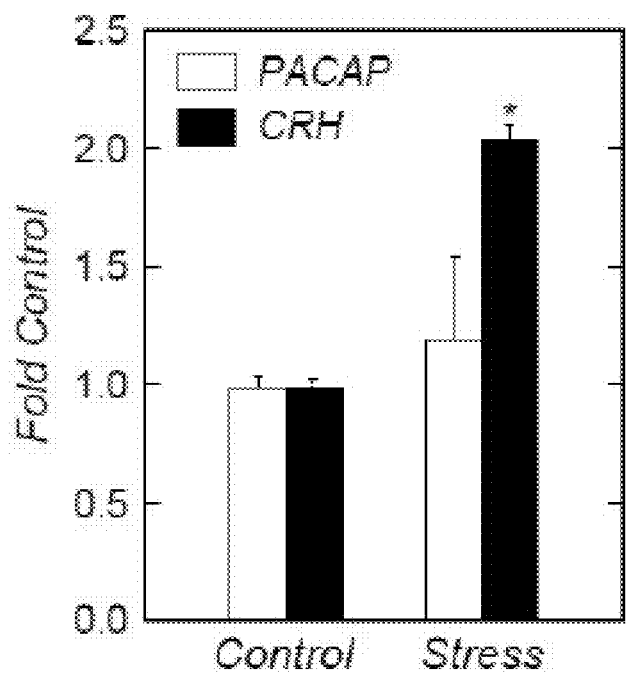
FIG. 11 shows a graph of data from an image analyses demonstrated that CRH immunoreactivity was augmented by stress. n=4, Data represent Mean+SEM. Asterisk, significantly different from control at p=0.001.

The apparent dichotomy of PACAP and CRH expression in the oval nucleus of the BNST was even more striking in the CeA (FIG. 11). While CRH immunoreactivity in the CeA was robust and prominent in the lateral and medial subdivisions of the CeA, PACAP immunoreactivity was distinct and restricted to the lateral capsular division of the nuclei. Distribution patterns were similar for other CeA peptides (Cassell et al., *J Comp Neurol* 246: 478-499 (1986)). Upon analyses of the immunocytochemically stained sections, the PACAP and CRH expression patterns following repeated stress appeared converse of those in the BNST oval nucleus. Whereas PACAP immunoreactivity in the BNST oval nucleus was augmented after stress, no stress-mediated PACAP changes were observed in the CeA (FIGS. 10 and 13; df=5, t=−1.53, p=0.19). By contrast, stress had no apparent effects on BNST CRH expression but increased CeA CRH immunoreactivity and transcript levels approximately 2-fold (FIGS. 10 and 13; df=5, t=−13.81, p<0.001). The differential regulated expression of PACAP and CRH in the BNST and CeA may be indicative of their distinct but complementary roles in fear- and anxiety-like behavioral responses.

BNST PACAP38 Infusions Mimic the Behavioral Effects of Repeated Stressor Exposure.

Figure 12A:
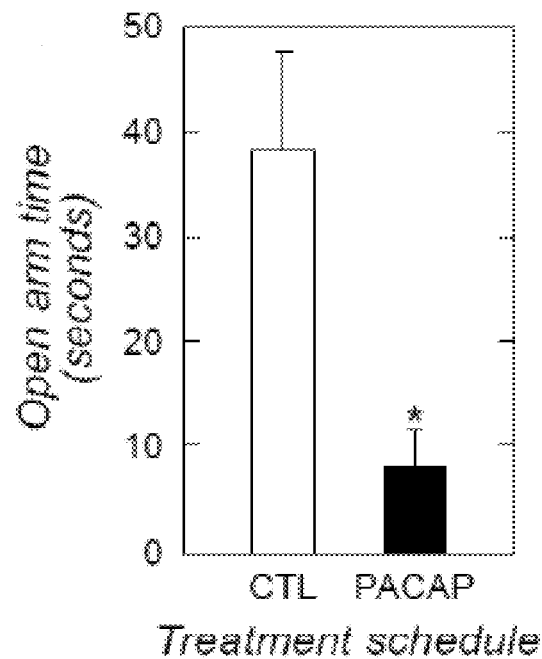
FIG. 12A shows a graph demonstrating PACAP38-infused animals having greater anxiety-like behavior as reflected by decreased open arm times compared to vehicle-treated animals.
Figure 12B:
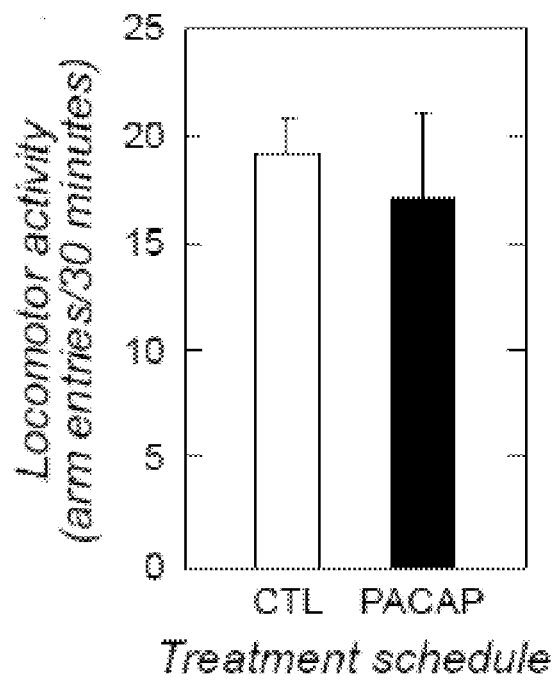
FIG. 12B shows a graph demonstrating that locomotor activity was not changed between PACAP38-infused animals and vehicle-treated animals.
Figure 12C:
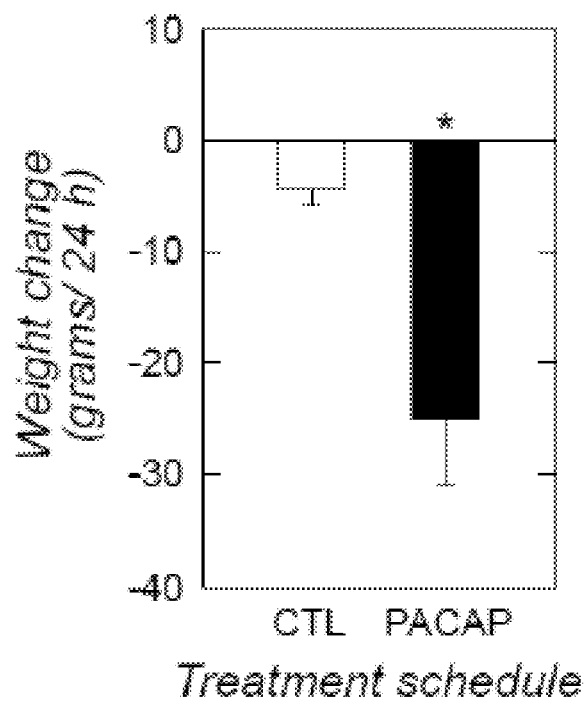
FIG. 12C shows a graph demonstrating that PACAP38-infused animals presented significant weight loss (approximately 8% of body weight) after 24 hours compared to vehicle controls. n=5, Data represent Mean+SEM. Asterisk, significantly different from vehicle control animal group at p<0.01.

To further characterize the behavioral consequences of BNST PACAP38 infusion, rats were implanted with bilateral cannulae targeted at the BNST. One week following implantation, rats received BNST infusions of PACAP38 (1 µg/0.5 µl) or vehicle, and were tested for anxiety-like responses. Consistent with an anxiogenic effect of BNST PACAP on baseline acoustic startle responding, BNST PACAP38 infusion was anxiogenic on the elevated-plus maze as measured by open arm time (FIG. 12A, df=8, t=3.3, p=0.01). Notably, locomotor activity as measured by the total number of arm entries was not affected (FIG. 12B, df=8, t=0.53, p=0.61). Moreover, rats demonstrated significantly more weight loss 24 hours after BNST PACAP38 infusions as compared to vehicle-infused rats (FIG. 12C; df=19, t=3.38, p<0.003).

BNST PAC1 Receptor Antagonist Infusions Block the Behavioral Consequences of Repeated Variate Stress.

Figure 13A:
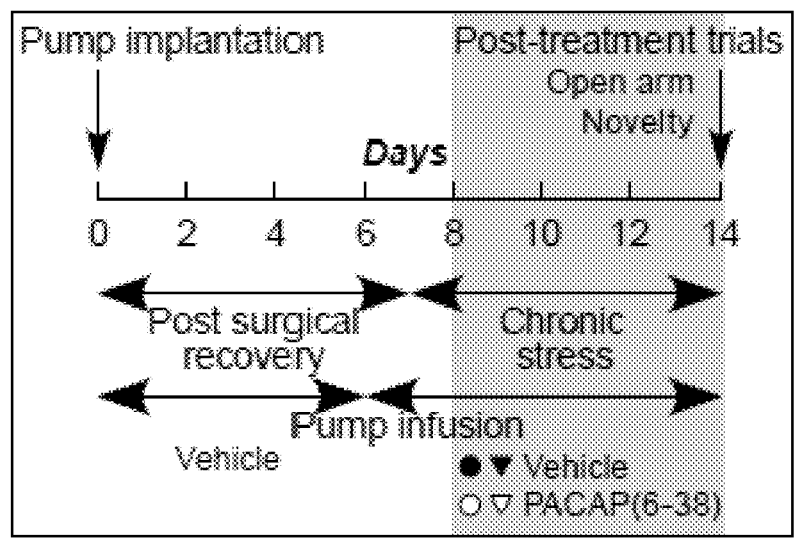
FIG. 13A depicts an experimental protocol for testing if PACAP receptor antagonist blocks the behavioral consequences of repeated variate stress.

To determine whether BNST PACAP receptor signaling mediates the behavioral consequences of repeated stress, osmotic minipumps were attached to bilateral indwelling cannulae to chronically infuse the BNST with PACAP(6-38), a PAC1 receptor antagonist, during the seven day repeated variate stress procedure (see above, FIG. 13A). Animal weight and food intake were monitored daily during the entire duration of the experiment, and the animals were evaluated on the elevated plus-maze and novel-object exploration tests 24-48 hours after the last stressor exposure. Only rats whose cannulae tips were located within the BNST were included for analysis.

Repeated variate stress was anxiogenic on the novel object test. ANOVA revealed a significant effect of stress (F(1,30)=18.15, p<0.001), and a significant effect of chronic PACAP antagonism (FIG. 13D; F(1,30)=4.57, p=0.041), but no interaction between antagonist and stress (F(1,30)=0.48, p=0.49). Planned contrast did reveal a significant difference between stress/vehicle and stress/PACAP(6-38) treatment (df=30, t=2.06, p=0.047). Thus, chronic BNST PACAP antagonism was anxiolytic on novel object tests irrespective of whether rats received repeated variate stress, and this reduction in anxiety was able to reverse the anxiogenic effect of stress.

ANOVA also revealed that repeated variate stress produced a strong trend towards increased anxiety-like behavior on the elevated plus maze (F(1,30)=2.98, p=0.066). Nonetheless, regardless of whether stress was anxiogenic, there was a significant effect of chronic PACAP antagonism on anxiety-like behavior (FIG. 13C; F(1,30)=4.95, p=0.034). There was no interaction between PACAP(6-38) and repeated stress (F(1,30)=0.45, p=0.63). Thus, chronic BNST PACAP antagonism was anxiolytic on the elevated-plus maze irrespective of whether rats received repeated variate stress. Together, these data suggest that chronic BNST PAC1 receptor antagonism is anxiolytic, and can mitigate the anxiogenic consequences of repeated stressor exposure.

Figure 13B:
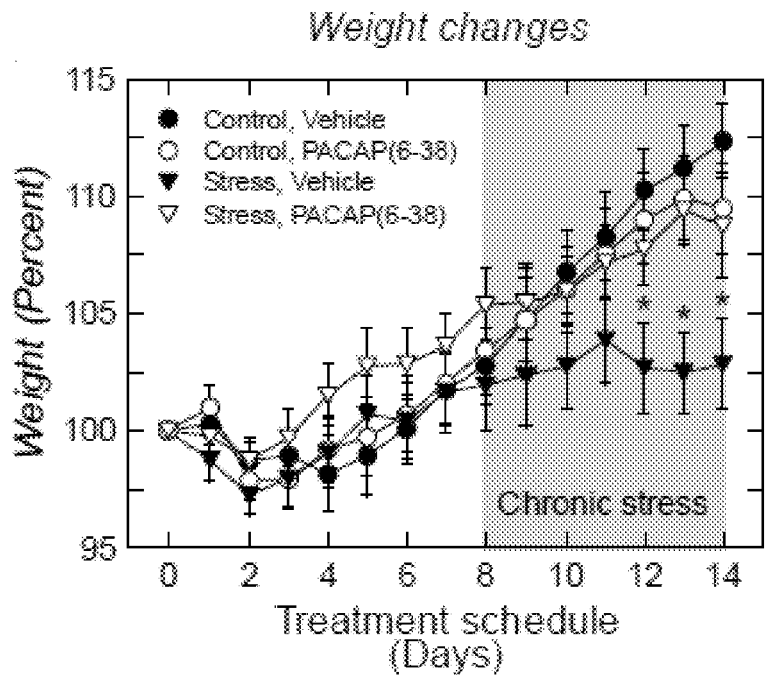
FIG. 13B shows a graph demonstrating that after transient post-surgical weight loss, non-stressed rats receiving vehicle (closed circles) or PACAP(6-38) (open circle) gained weight steadily during the experimental course. Stressed rats receiving vehicle BNST infusions (filled triangles) failed to gain weight; stressed rats receiving PACAP(6-38) infusions (open triangle) gained weight comparable to controls. n=9, Data represent mean percent weight change from start+ SEM. Asterisks, different from control and PACAP(6-38) groups at p<0.001.
Figure 13C:
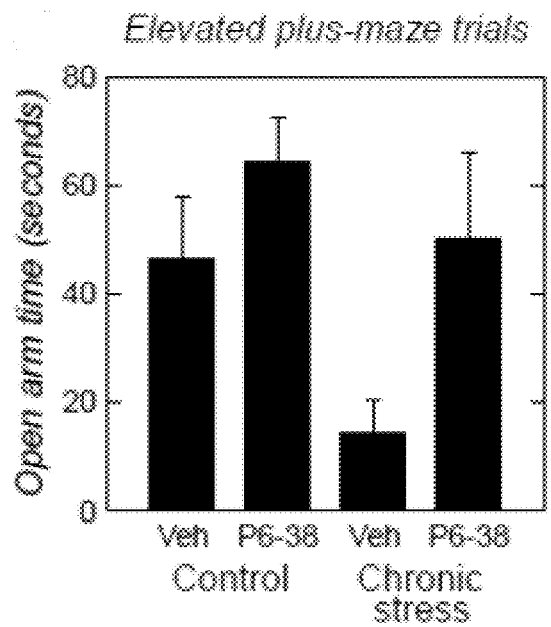
FIG. 13C shows a graph of data from an elevated plus-maze behavioral test demonstrating that chronic infusion with PACAP receptor antagonist was anxiolytic and attenuated the stress induced anxiety-related responses.
Figure 13D:
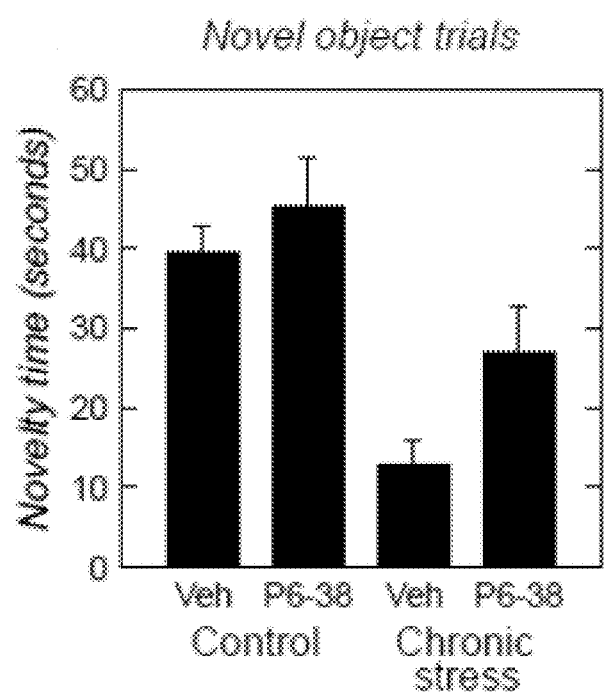
FIG. 13D shows a graph of data from a novel objects behavioral test demonstrating that chronic infusion with PACAP receptor antagonist was anxiolytic and attenuated the stress induced anxiety-related responses.

After cannulae placement and postsurgical recovery (day 2-7), non-stressed vehicle-infused rats exhibited a steady increase in body weight (FIG. 13B, filled circles); non-stressed animals receiving PACAP(6-38) gained weight similarly (FIG. 13B; closed circles) demonstrating that there were no apparent effects of the antagonist alone on weight. By contrast, repeated variate stress over the last week of study, attenuated weight gain in the vehicle-treated rats (FIG. 13B; closed triangles). Continuous BNST PACAP(6-38) infusions during the repeated stress period blocked the stress-induced changes in weight gain (FIG. 13B; open triangles); thus, unlike the plateau in weight change observed in the stress/vehicle group, stressed rats receiving PACAP(6-38) increased their body weight at rates comparable to those of non-stressed controls.

Weight data were analyzed using a 2×2×7 mixed ANOVA with stress and antagonist treatment as between subjects variables and percent weight change during the stress period as within subjects variables. Because data did not meet assumptions of sphericity, Greenhouse-Geisser corrections were used for all tests on weight change. There was a main effect of day, such that overall weight reliably increased over the seven day span F(1.878/58.203)=91.406, p<0.001, and interaction between day and stress treatment F(1.878/58.203)=18.847, p<0.001. There was no interaction between day and antagonist treatment F(1.878/58.203)=1.042, p=0.356; however, there was a three-way interaction between day, stress treatment and antagonist treatment F(1.878/58.203)=4.264, p=0.021. Thus, chronic BNST PAC1 antagonism blunted the effect of repeated variate stress on weight gain.

The data demonstrated in this Example, showed that PACAP is expressed in the CRH-rich BNST oval nucleus and CeA; however, PACAP and CRH immunoreactivities were not colocalized. Repeated variate stress substantially increased PACAP transcript and protein expression selectively in the BNST oval nucleus, but not the CeA, and chronic BNST PAC1 receptor antagonism was anxiolytic and attenuated the effects of repeated variate stress on weight gain. Further, BNST PACAP infusion was anxiogenic on the elevated plus maze. Without being bound by any particular theory, these data suggested that BNST PACAP mediates many of the consequences of chronic and repeated stressor exposure. The data in this Example also corroborated the studies presented herein in Examples 1-12, suggesting that the BNST is a critical brain region mediating the behavioral effects of PACAP.

Example 14

Three antibodies, designated VT026, VT027 and VT028, were generated for use in inhibiting PACAP activity. Tables 5-7 show radioimmunoassay (RIA) data for antisera designated VT026, VT027, and VT028, respectively. Each antibody was directed to the carboxyl-terminal end of PACAP38. The specific sequence used to generate the antibodies was Cys-Tyr-Lys-Gln-Arg-Val-Lys-Asn-Lys-NH2 (SEQ ID NO:2). The Cys was added to facilitate peptide conjugation to a carrier protein for rabbit immunization; the remaining sequence is unique to PACAP38. The three antisera had a working dilution of 1:100K-1:200K in radioimmunoassays against iodinated PACAP(31-38) and demonstrated an assay midpoint (a measure of sensitivity) of 9-20 fmol. The summary of the antisera characteristics are shown in Tables 5-7.

TABLE 1

|  | PTSD | No PTSD | $x^2$ | Sig. |
|---|---|---|---|---|
| Initial PACAP Blood Sample | | | | |
| Sex | | | .82 | .37 |
| Female | 45.8% (n = 11) | 57.5% (n = 23) | | |
| Male | 54.2% (n = 13) | 42.5% (n = 17) | | |
| Race/Ethnicity | | | 1.69 | .20 |
| African American | 95.8% (n = 23) | 100% (n = 40) | | |
| White/Biracial/Latino/Asian | 4.2% (n = 1) | 0% (n = 0) | | |
| Employment | | | .215 | .64 |
| Unemployed | 83.3% (n = 20) | 87.5% (n = 35) | | |
| Employed | 16.7% (n = 4) | 12.5% (n = 5) | | |
| Total Household Monthly Income | | | .01 | .91 |
| <$1000 | 82.6% (n = 19) | 83.8% (n = 34) | | |
| ≥$1000 | 17.4% (n = 4) | 16.2% (n = 6) | | |
| Current Substance Abuse | | | 4.18 | .04 |
| No | 83.3% (n = 20) | 97.5% (n = 39) | | |
| Yes | 16.7% (n = 4) | 2.5% (n = 1) | | |
| Lifetime Suicide Attempt | | | 3.05 | .08 |
| No | 69.6% (n = 16) | 87.5% (n = 35) | | |
| Yes | 30.4% (n = 7) | 12.5% (n = 5) | | |
| Replication PACAP Blood Sample | | | | |
| Sex | | | | |
| Female | 100% (n = 30) | 100% (n = 45) | | |
| Male | 0% (n = 0) | 0% (n = 0) | | |
| Race/Ethnicity | | | 3.96 | .52 |
| African American | 96.7% (n = 29) | 93.3% (n = 42) | | |
| White/Biracial/Latino/Asian | 3.3% (n = 1) | 6.7% (n = 3) | | |
| Employment | | | .376 | .54 |
| Unemployed | 73.3% (n = 22) | 66.7% (n = 30) | | |
| Employed | 26.7% (n = 8) | 33.3% (n = 15) | | |
| Total Household Monthly Income | | | .14 | .70 |
| <$1000 | 65.5% (n = 19) | 69.8% (n = 30) | | |
| ≥$1000 | 34.5% (n = 10) | 30.2% (n = 13) | | |
| Current Substance Abuse | | | 1.52 | .22 |
| No | 96.7% (n = 29) | 100% (n = 45) | | |
| Yes | 3.3% (n = 1) | 0% (n = 0) | | |
| Lifetime Suicide Attempt | | | 1.25 | .27 |
| No | 62.1% (n = 18) | 74.4% (n = 32) | | |
| Yes | 37.9% (n = 11) | 25.6% (n = 11) | | |

Note that totals for each column are not always equal due to occasional subjects with missing data.

TABLE 2

|  | PTSD | No PTSD | $x^2$ | Sig. |
|---|---|---|---|---|
| Initial Genetics Sample | | | | |
| Sex | | | .45 | .50 |
| Female | 64.7% (n = 165) | 62.2% (n = 338) | | |
| Male | 35.3% (n = 90) | 37.8% (n = 205) | | |
| Race/Ethnicity | | | .02 | .88 |
| African American | 92.5% (n = 235) | 92.2% (n = 498) | | |
| White/Bi-racial/Latino/Asian | 7.5% (n = 19) | 7.8% (n = 42) | | |
| Employment | | | 2.47 | .12 |
| Unemployed | 77.6% (n = 198) | 72.4% (n = 391) | | |
| Employed | 22.4% (n = 57) | 27.6% (n = 149) | | |
| Total Household Monthly Income | | | 1.36 | .24 |
| <$1000 | 73.6% (n = 184) | 69.5% (n = 365) | | |
| ≥$1000 | 26.4% (n = 66) | 30.5% (n = 160) | | |
| Current Substance Abuse | | | 24.5 | <.001 |
| Yes | 87.7% (n = 222) | 96.8% (n = 515) | | |
| No | 12.3% (n = 31) | 3.2% (n = 17) | | |
| Lifetime Suicide Attempt | | | 42.9 | <.001 |
| No | 69.8% (n = 171) | 88.9% (n = 466) | | |
| Yes | 30.2% (n = 74) | 11.1% (n = 58) | | |
| Replication Genetics Sample | | | | |
| Sex | | | .23 | .63 |
| Female | 60.8% (n = 87) | 58.4% (n = 173) | | |
| Male | 39.2% (n = 56) | 41.6% (n = 123) | | |
| Race/Ethnicity | | | .48 | .49 |
| African American | 93.7% (n = 134) | 91.8% (n = 270) | | |
| White/Bi-racial/Latino/Asian | 6.3% (n = 9) | 8.2% (n = 24) | | |
| Employment | | | 4.63 | .03 |
| Unemployed | 72.0% (n = 103) | 61.6% (n = 181) | | |
| Employed | 28.0% (n = 40) | 38.4% (n = 113) | | |
| Total Household Monthly Income | | | 2.23 | .14 |
| <$1000 | 67.9% (n = 91) | 60.4% (n = 172) | | |
| ≥$1000 | 32.1% (n = 43) | 39.6% (n = 113) | | |
| Current Substance Abuse | | | .94 | .33 |
| No | 95.0% (n = 132) | 96.9% (n = 278) | | |
| Yes | 5.0% (n = 7) | 3.1% (n = 9) | | |
| Lifetime Suicide Attempt | | | 7.45 | .01 |
| No | 78.7% (n = 111) | 88.6% (n = 257) | | |
| Yes | 21.3% (n = 30) | 11.4% (n = 33) | | |

Note that totals for each column are not always equal due to occasional subjects with missing data

TABLE 3

| Variable | PTSD status | N | Mean | F | Sig. |
|---|---|---|---|---|---|
| Initial PACAP Blood Sample | | | | | |
| Age | No PTSD | 40 | 41.52 | 1.68 | .20 |
| | PTSD | 24 | 45.79 | | |
| BDI | No PTSD | 39 | 7.72 | 56.9 | <.001 |
| | PTSD | 24 | 26.4 | | |
| CTQ | No PTSD | 39 | 39.35 | 6.87 | .011 |
| | PTSD | 24 | 50.94 | | |
| TEI | No PTSD | 40 | 2.39 | 9.99 | .002 |
| | PTSD | 23 | 4.05 | | |
| PSS | No PTSD | 40 | 4.3 | 145.57 | <.001 |
| | PTSD | 24 | 29.25 | | |

TABLE 3-continued

| Variable | PTSD status | N | Mean | F | Sig. |
|---|---|---|---|---|---|
| Replication PACAP Blood Sample | | | | | |
| Age | No PTSD | 45 | 30.44 | 3.33 | .07 |
|  | PTSD | 30 | 34.97 | | |
| BDI | No PTSD | 45 | 12.93 | 38.57 | <.001 |
|  | PTSD | 29 | 28.37 | | |
| CTQ | No PTSD | 45 | 42.72 | 7.09 | .01 |
|  | PTSD | 30 | 56.25 | | |
| TEI | No PTSD | 45 | 2.55 | 1.48 | .23 |
|  | PTSD | 30 | 3.16 | | |
| PSS | No PTSD | 45 | 7.65 | 116.84 | <.001 |
|  | PTSD | 30 | 29.24 | | |
| Initial Gene Sample | | | | | |
| Age | No PTSD | 538 | 39.71 | 5.26 | .02 |
|  | PTSD | 254 | 41.98 | | |
| BDI[1] | No PTSD | 524 | 10.33 | 293.12 | <.001 |
|  | PTSD | 243 | 24.10 | | |
| CTQ[2] | No PTSD | 533 | 38.53 | 72.12 | <.001 |
|  | PTSD | 246 | 49.51 | | |
| TEI[3] | No PTSD | 537 | 2.33 | 60.24 | <.001 |
|  | PTSD | 247 | 3.45 | | |
| PSS[4] | No PTSD | 545 | 6.16 | 1308.9 | <.001 |
|  | PTSD | 256 | 26.87 | | |
| Replication Genetics Sample | | | | | |
| Age | No PTSD | 294 | 38.09 | .024 | .877 |
|  | PTSD | 143 | 38.29 | | |
| BDI | No PTSD | 275 | 9.45 | 159.20 | <.001 |
|  | PTSD | 127 | 23.29 | | |
| CTQ | No PTSD | 295 | 37.50 | 42.34 | <.001 |
|  | PTSD | 143 | 48.15 | | |
| TEI | No PTSD | 292 | 2.14 | 48.28 | <.001 |
|  | PTSD | 141 | 3.43 | | |
| PSS | No PTSD | 296 | 6.23 | 582.77 | <.001 |
|  | PTSD | 143 | 26.77 | | |

Note that totals for each column are not always equal due to occasional subjects with missing data
[1]BDI = Beck Depression Inventory,
[2]CTQ = Childhood Trauma Questionnaire Total Score,
[3]TEI = Total types of non-childhood abuse trauma,
[4]PSS = PTSD symptoms

TABLE 4

(SEQ ID NO: 11-92, top to bottom)

|  | Start pos. | Strand | Matrix sim. | Core sim. | Sequence | SNP |
|---|---|---|---|---|---|---|
| 1 | 31084308 | − | 0.818 | 0.809 | ctgggacagggcCACCcac | no SNP |
| 2 | 31085588 | + | 0.914 | 1 | ctatcacAAGGacagaaaa | no SNP |
| 3 | 31085910 | − | 0.93 | 1 | gtttgtcAAGGccacagga | rs78430287 |
| 4 | 31086075 | − | 0.813 | 1 | tacaGTCAaagtgagccag | no SNP |
| 5 | 31086111 | − | 0.883 | 1 | atggGTCAgagtctcctgc | no SNP |
| 6 | 31088143 | − | 0.936 | 1 | gccctagaAGGTcaagtgc | no SNP |
| 7 | 31088391 | − | 0.872 | 1 | tgggGTCAgatggccagag | no SNP |
| 8 | 31089400 | + | 0.974 | 1 | ggcttacaAGGTcagagct | no SNP |
| 9 | 31089695 | − | 0.935 | 1 | ctagcccAAGGacacacag | no SNP |
| 10 | 31090164 | − | 0.992 | 1 | gaagatcaAGGTcatctat | no SNP |
| 11 | 31090794 | + | 0.837 | 0.779 | cctggacaaggtGGCCata | no SNP |
| 11 | 31090794 | − | 0.818 | 0.794 | tatggccaccttGTCCagg | no SNP |
| 12 | 31091057 | − | 0.85 | 0.806 | acagGTAAaggtggcctag | no SNP |
| 12 | 31091057 | + | 0.846 | 0.779 | ctaggccaccttTACCtgt | no SNP |
| 13 | 31092118 | + | 0.852 | 1 | cagggacacacgGACCcg | no SNP |
| 14 | 31093439 | + | 0.873 | 0.781 | ggagGGCAacttgccctgg | no SNP |
| 14 | 31093439 | − | 0.884 | 0.781 | ccaGGGCAagttgccctcc | no SNP |
| 15 | 31093485 | + | 0.952 | 1 | catcctgaAGGTcaagcta | no SNP |
| 16 | 31093678 | − | 0.983 | 1 | cctccccaAGGTcagtgag | no SNP |
| 17 | 31094278 | − | 0.877 | 1 | ccagccccAGGTcaatgaa | no SNP |
| 18 | 31094433 | + | 0.831 | 0.774 | ggagGTGAcaatgagtttc | no SNP |
| 19 | 31095813 | + | 0.983 | 1 | ggagggcaAGGTcataaag | no SNP |
| 20 | 31095819 | + | 0.87 | 1 | caagGTCAtaaagggcggg | no SNP |
| 21 | 31095878 | − | 0.882 | 1 | atcctccAAGGccaactca | no SNP |

TABLE 4-continued (SEQ ID NO: 11-92, top to bottom)

| | Start pos. | Strand | Matrix sim. | Core sim. | Sequence | SNP |
|---|---|---|---|---|---|---|
| 22 | 31096906 | + | 0.887 | 0.778 | actcctcCAGGtcaggaga | no SNP |
| 23 | 31096978 | - | 0.904 | 1 | caagGTCAtgctgcagagt | no SNP |
| 24 | 31096984 | - | 0.986 | 1 | cttccccaAGGTcatgctg | no SNP |
| 25 | 31098160 | - | 0.983 | 1 | actttccaAGGTcacacaa | no SNP |
| 26 | 31101000 | + | 0.875 | 1 | ccagtgctAGGTcacgcca | no SNP |
| 27 | 31101407 | + | 0.827 | 1 | gagggacacaaaGACCcct | no SNP |
| 28 | 31102744 | - | 0.838 | 0.809 | cggggcaagacCACCtcc | no SNP |
| 29 | 31103256 | - | 0.853 | 0.791 | gcagGGCAttgtgggctgg | no SNP |
| 30 | 31103402 | + | 0.843 | 0.794 | gtgggtgaggctGTCCtca | no SNP |
| 30 | 31103402 | - | 0.843 | 0.809 | tgaggacagcctCACCcac | no SNP |
| 31 | 31104740 | - | 0.837 | 1 | gtgaggcatccaGACCaca | no SNP |
| 32 | 31106735 | + | 0.914 | 1 | ggagGTCAgggtgtgaagg | no SNP |
| 33 | 31108105 | + | 0.93 | 1 | agggtgaaAGGTcatacag | no SNP |
| 34 | 31108438 | - | 0.974 | 1 | tgacagcaAGGTcaatgct | no SNP |
| 35 | 31108993 | + | 0.94 | 1 | ctggccaaAGGTcagctga | no SNP |
| 36 | 31109007 | - | 0.928 | 1 | gtgtttcAAGGacatcagc | no SNP |
| 37 | 31111801 | + | 0.859 | 0.787 | atagGCCAgtgtgatcagc | no SNP |
| 38 | 31114138 | - | 0.913 | 1 | cgagGTCAcagggccactt | no SNP |
| 39 | 31114144 | - | 0.877 | 1 | cactgccgAGGTcacaggg | RS57410846 |
| 40 | 31114269 | + | 0.888 | 1 | cacgGTCAacatgggctgc | no SNP |
| 41 | 31114313 | + | 0.933 | 1 | ctctttcAAGGacatgatg | no SNP |
| 42 | 31114319 | - | 0.83 | 0.794 | ctgtgacatcatGTCCttg | no SNP |
| 43 | 31115668 | - | 0.821 | 0.809 | gctggacaccccCACCttg | no SNP |
| 44 | 31115903 | - | 0.985 | 1 | tctcaccaAGGTcaccagc | no SNP |
| 45 | 31117734 | + | 0.882 | 0.772 | ttagGCCAcgctggcctag | no SNP |
| 46 | 31117734 | - | 0.884 | 0.772 | ctagGCCAgcgtggcctaa | no SNP |
| 47 | 31117779 | + | 0.914 | 1 | aagcaccAAGGacagggag | no SNP |
| 48 | 31119037 | - | 0.908 | 1 | ccagGTCAcatggccacac | no SNP |
| 49 | 31119043 | - | 0.875 | 1 | ctaaggccAGGTcacatgg | no SNP |
| 50 | 31120724 | + | 0.826 | 1 | gcatgtcagctgGACCttg | no SNP |
| 51 | 31121902 | + | 0.837 | 1 | agtaggcacaatGACCgcg | no SNP |
| 52 | 31121902 | - | 0.901 | 1 | cgcgGTCAttgtgcctact | no SNP |
| 53 | 31122642 | - | 0.905 | 1 | tgtggccAAGGccacctcc | no SNP |
| 54 | 31125315 | + | 0.941 | 1 | gaagaggaAGGTcaggtgg | no SNP |
| 55 | 31126976 | + | 0.845 | 0.774 | actgGTGAtactgacttttt | no SNP |
| 56 | 31127311 | - | 0.93 | 1 | tcatcccAAGGacactcac | no SNP |
| 57 | 31131686 | + | 0.857 | 1 | tcctGTCAttgtgccttgt | no SNP |
| 58 | 31132443 | - | 0.872 | 1 | ctgatgctAGGTcaccctat | no SNP |

TABLE 4-continued (SEQ ID NO: 11-92, top to bottom)

|    | Start pos. | Strand | Matrix sim. | Core sim. | Sequence              | SNP       |
|----|------------|--------|-------------|-----------|-----------------------|-----------|
| 59 | 31132860   | +      | 0.811       | 0.779     | tcggggcagctcTACCtct   | no SNP    |
| 60 | 31133995   | -      | 0.894       | 1         | cagacacAAGGgcagtgtc   | no SNP    |
| 61 | 31134660   | -      | 0.857       | 1         | cagggtctccttGACCctg   | no SNP    |
| 61 | 31134660   | +      | 0.915       | 1         | caggGTCAaggagaccctg   | no SNP    |
| 62 | 31135494   | -      | 0.877       | 1         | tcagGTCAgagaggacgag   | rs2267735 |
| 63 | 31135669   | +      | 0.876       | 1         | gtagGTCAgggttaactgg   | no SNP    |
| 64 | 31135884   | -      | 0.874       | 1         | tggggccaaggaGACCcca   | no SNP    |
| 65 | 31136983   | -      | 0.869       | 1         | agatGTCAgaatgtcttaa   | no SNP    |
| 66 | 31139247   | -      | 0.891       | 1         | gaagGTCAacttgggtgtc   | no SNP    |
| 67 | 31139253   | -      | 0.952       | 1         | ggctgtgaAGGTcaacttg   | no SNP    |
| 68 | 31140809   | -      | 0.886       | 1         | acagtccAAGGgcaacacc   | no SNP    |
| 69 | 31142030   | -      | 0.839       | 1         | ctaggacacctgGACCatg   | no SNP    |
| 70 | 31143664   | -      | 0.942       | 1         | ggtggagaAGGTcaagtca   | no SNP    |
| 71 | 31143686   | +      | 0.888       | 1         | ttaatccAAGGccatttaa   | no SNP    |
| 72 | 31143723   | -      | 0.828       | 0.809     | catagtcagtctCACCaga   | no SNP    |
| 73 | 31144368   | +      | 0.88        | 1         | ccccatccAGGTcatggtg   | no SNP    |
| 74 | 31144374   | +      | 0.914       | 1         | ccagGTCAtggtgtatttc   | no SNP    |
| 75 | 31147441   | -      | 0.917       | 1         | caaggtcAAGGgcataaaa   | no SNP    |
| 76 | 31147447   | -      | 0.994       | 1         | gtgagtcaAGGTcaagggc   | no SNP    |
| 77 | 31147886   | -      | 0.933       | 1         | actggccAAGGacacagag   | no SNP    |

TABLE 5

| ANTIBODY | VT027 |
| --- | --- |
| ANTIBODY DILUTION | 1:200K |

| STANDARD MW (g/mole) | 4,531.5 |
| --- | --- |
| STANDARD INPUT (ng) | 4.08 |
| STANDARD DILUTION | 2 |
| SAMPLE DILUTION | 2 |
| SAMPLE VOLUME (µl) | 50.00 |
| TOTAL SAMPLE VOLUME (µl) | 120.00 |

| TUBE | TOTAL INPUT | MINUS Ab | MINUS COLD |
| --- | --- | --- | --- |
| 1 | 24393 | 252 | 7937 |
| 2 | 24387 | 251 | 8371 |
| 3 | | | |
| 4 | | | |
| 5 | | | |
| 6 | | | |
| MEAN | 24390.00 | 251.50 | 8154.00 |

| SLOPE | −0.94 |
| --- | --- |
| INTERCEPT | 1.52 |
| MIDPOINT (lmol) | 9.2 |
| MIDPOINT (pg) | 41 |
| DETECTION LIMIT (pg) | 2.19 |
| MINUS Ab (% INPUT) | 1.0 |
| MINUS COLD (% INPUT) | 33.4 |
| ASSAY DELTA | 7902.5 |

TABLE 5-continued

| STD | CPM | PEPTIDE (pg) | CALC'D (pg) | ERROR (%) | WT*ERR | LOG (pg) | BINDING | LOGIT | WEIGHT | d1 | d2 | d3 | d4 |
|---|---|---|---|---|---|---|---|---|---|---|---|---|---|
| 1 | 490 | 2,040 | 1,887 | 18 | 0.5543 | 3.3098 | 0.0302 | −1.5070 | 0.0303 | 0.1002 | 0.3318 | −0.0458 | −0.1511 |
| 2 | 656 | 1,020 | 928 | 9 | 0.9794 | 3.0088 | 0.0512 | −1.2880 | 0.1085 | 0.3263 | 0.9818 | −0.1375 | −0.4138 |
| 3 | 875 | 510 | 587 | 11 | 2.9880 | 2.7075 | 0.0789 | −1.0872 | 0.2880 | 0.7203 | 1.9502 | −0.2839 | −0.7687 |
| 4 | 1,413 | 255 | 270 | 6 | 3.8437 | 2.4085 | 0.1470 | −0.7837 | 0.6725 | 1.8184 | 3.8948 | −0.5138 | −1.2380 |
| 5 | 2,190 | 128 | 137 | 8 | 7.1983 | 2.1055 | 0.2453 | −0.4881 | 0.9485 | 1.9971 | 4.2048 | −0.4629 | −0.9747 |
| 6 | 3,503 | 64 | 61 | 5 | 4.7738 | 1.8045 | 0.4115 | −0.1555 | 0.9999 | 1.8043 | 3.2558 | −0.1554 | −0.2805 |
| 7 | 4,865 | 32 | 29 | 9 | 9.2453 | 1.5035 | 0.5538 | 0.1470 | 0.9999 | 1.5034 | 2.2602 | 0.1470 | 0.2209 |
| 8 | 5,900 | 18 | 16 | 2 | 2.0925 | 1.2024 | 0.7148 | 0.3990 | 0.9813 | 1.1799 | 1.4187 | 0.3915 | 0.4708 |
| 9 | 8,553 | 6 | 7 | 8 | 5.7283 | 0.9014 | 0.8354 | 0.7054 | 0.7509 | 0.8759 | 0.6101 | 0.5297 | 0.4775 |
| 10 | 7,276 | 4 | 5 | 14 | 6.5040 | 0.8004 | 0.8889 | 0.9031 | 0.4720 | 0.2834 | 0.1701 | 0.4293 | 0.2559 |
| 11 | 7,615 | 2 | 3 | 29 | 185.3458 | 0.2993 | 0.9318 | 1.1355 | 0.2004 | 0.0600 | 0.0180 | 0.2275 | 0.0681 |
| 12 | 7,964 | 1 | 1 | 19 | 0.3222 | −0.0017 | 0.9780 | 1.5084 | 0.0168 | 0.0000 | 0.0000 | 0.0270 | 0.0000 |
| | | | | SUM | 229.5751 | | | | | | | | |
| | | | WTD ERR (%) | 36 | | | | | SUM | 6.4470 | 10.2701 | 19.0955 | 0.1499 | −2.3316 |

TABLE 6

| | | |
|---|---|---|
| ANTIBODY | | VT027 |
| ANTIBODY DILUTION | | 1:200K |
| STANDARD MW (g/mole) | | 4,531.5 |
| STANDARD INPUT (ng) | | 4.08 |
| STANDARD DILUTION | | 2 |
| SAMPLE DILUTION | | 2 |
| SAMPLE VOLUME (μl) | | 50.00 |
| TOTAL SAMPLE VOLUME (μl) | | 120.00 |

| TUBE | TOTAL INPUT | MINUS Ab | MINUS COLD |
|---|---|---|---|
| 1 | 24393 | 252 | 7937 |
| 2 | 24387 | 251 | 8371 |
| 3 | | | |
| 4 | | | |
| 5 | | | |
| 6 | | | |
| MEAN | 24390.00 | 251.50 | 8154.00 |

| | |
|---|---|
| SLOPE | −0.94 |
| INTERCEPT | 1.52 |
| MIDPOINT (lmol) | 9.2 |
| MIDPOINT (pg) | 41 |
| DETECTION LIMIT (pg) | 2.19 |
| MINUS Ab (% INPUT) | 1.0 |
| MINUS COLD (% INPUT) | 33.4 |
| ASSAY DELTA | 7902.5 |

| STD | CPM | PEPTIDE (pg) | CALC'D (pg) | ERROR (%) | WT*ERR | LOG (pg) | BINDING | LOGIT | WEIGHT | d1 | d2 | d3 | d4 |
|---|---|---|---|---|---|---|---|---|---|---|---|---|---|
| 1 | 490 | 2,040 | 1,687 | 15 | 0.5543 | 3.3095 | 0.0302 | −1.5070 | 0.0303 | 0.1002 | 0.3318 | −0.0458 | −0.1511 |
| 2 | 558 | 1,020 | 928 | 9 | 0.9794 | 3.0085 | 0.0512 | −1.2880 | 0.1085 | 0.3263 | 0.9818 | −0.1375 | −0.4138 |
| 3 | 875 | 510 | 567 | 11 | 2.9860 | 2.7078 | 0.0789 | −1.0672 | 0.2880 | 0.7203 | 1.9502 | −0.2839 | −0.7687 |
| 4 | 1,413 | 255 | 270 | 8 | 3.8437 | 2.4055 | 0.1470 | −0.7637 | 0.8725 | 1.6184 | 3.5948 | −0.5135 | −1.2360 |
| 5 | 2,190 | 128 | 137 | 8 | 7.1983 | 2.1055 | 0.2453 | −0.4881 | 0.9485 | 1.9971 | 4.2048 | −0.4629 | −0.9747 |
| 6 | 3,503 | 64 | 61 | 5 | 4.7738 | 1.6045 | 0.4115 | −0.1555 | 0.9999 | 1.8043 | 3.2558 | −0.1554 | −0.2805 |
| 7 | 4,885 | 32 | 29 | 9 | 9.2453 | 1.5035 | 0.5838 | 0.1470 | 0.9999 | 1.5034 | 2.2602 | 0.1470 | 0.2209 |
| 8 | 5,900 | 18 | 16 | 2 | 2.0925 | 1.2024 | 0.7148 | 0.3990 | 0.9813 | 1.1799 | 1.4187 | 0.3915 | 0.4708 |
| 9 | 5,853 | 8 | 7 | 8 | 5.7269 | 0.9014 | 0.8354 | 0.7054 | 0.7509 | 0.6769 | 0.5101 | 0.5297 | 0.4775 |
| 10 | 7,276 | 4 | 5 | 14 | 8.5040 | 0.8004 | 0.8889 | 0.9031 | 0.4720 | 0.2834 | 0.1701 | 0.4293 | 0.2559 |
| 11 | 7,615 | 2 | 3 | 29 | 155.3456 | 0.2993 | 0.9318 | 1.1355 | 0.2004 | 0.0600 | 0.0180 | 0.2275 | 0.0881 |
| 12 | 7,984 | 1 | 1 | 19 | 0.3222 | −0.0017 | 0.9780 | 1.8084 | 0.0188 | 0.0000 | 0.0000 | 0.0270 | 0.0000 |
| | | | | SUM | 229.5751 | | | | | | | | |
| | | | WTD ERR (%) | 36 | | | | | SUM | 6.4470 | 10.2701 | 19.0955 | 0.1499 | −2.3316 |

TABLE 7

| ANTIBODY | VT028 |
|---|---|
| ANTIBODY DILUTION | 1:200K |

| | |
|---|---|
| STANDARD MW (g/mole) | 4,531.5 |
| STANDARD INPUT (ng) | 4.08 |
| STANDARD DILUTION | 2 |
| SAMPLE DILUTION | 2 |
| SAMPLE VOLUME (µl) | 50.00 |
| TOTAL SAMPLE VOLUME (µl) | 120.00 |

| TUBE | TOTAL INPUT | MINUS Ab | MINUS COLD |
|---|---|---|---|
| 1 | 24393 | 275 | 11415 |
| 2 | 24387 | 228 | 11397 |
| 3 | | | |
| 4 | | | |
| 5 | | | |
| 6 | | | |
| MEAN | 24390.00 | 250.50 | 11407.50 |

| | |
|---|---|
| SLOPE | −1.08 |
| INTERCEPT | 2.09 |
| MIDPOINT (fmol) | 19.3 |
| MIDPOINT (pg) | 87 |
| DETECTION LIMIT (pg) | 6.69 |
| MINUS Ab (% INPUT) | 1.0 |
| MINUS COLD (% INPUT) | 46.8 |
| ASSAY DELTA | 11157 |

| STD | CPM | PEPTIDE (pg) | CALC'D (pg) | ERROR (%) | WT*ERR | LOG (pg) | BINDING | LOGIT | WEIGHT | d1 | d2 | d3 | d4 |
|---|---|---|---|---|---|---|---|---|---|---|---|---|---|
| 1 | 684 | 2,040 | 1,722 | 16 | 0.8874 | 3.3098 | 0.0389 | −1.3933 | 0.0589 | 0.1882 | 0.6228 | −0.0792 | −0.2622 |
| 2 | 1,018 | 1,020 | 985 | 3 | 0.6836 | 3.0086 | 0.0886 | −1.1327 | 0.2028 | 0.8102 | 1.6358 | −0.2297 | −0.6912 |
| 3 | 1,733 | 510 | 499 | 2 | 1.2996 | 2.7076 | 0.1329 | −0.8146 | 0.5997 | 1.8238 | 4.3968 | −0.4889 | −1.3228 |
| 4 | 2,783 | 255 | 273 | 7 | 6.3895 | 2.4085 | 0.2270 | −0.5322 | 0.9226 | 2.2202 | 5.3431 | −0.4910 | −1.1815 |
| 5 | 4,349 | 128 | 145 | 13 | 13.4395 | 2.1055 | 0.3673 | −0.2361 | 0.9990 | 2.1033 | 4.4285 | −0.2358 | −0.4965 |
| 6 | 7,008 | 54 | 59 | 8 | 8.1571 | 1.8045 | 0.5058 | 0.1855 | 0.9997 | 1.8040 | 3.2553 | 0.1865 | 0.3365 |
| 7 | 8,843 | 32 | 28 | 11 | 10.2007 | 1.5035 | 0.7701 | 0.5251 | 0.9272 | 1.3940 | 2.0958 | 0.4869 | 0.7320 |
| 8 | 10,072 | 16 | 14 | 14 | 7.4876 | 1.2024 | 0.5803 | 0.8655 | 0.5244 | 0.8305 | 0.7581 | 0.4544 | 0.5484 |
| 9 | 10,448 | 5 | 10 | 22 | 6.7727 | 0.9014 | 0.9140 | 1.0264 | 0.3113 | 0.2808 | 0.2530 | 0.3198 | 0.2881 |
| 10 | 10,800 | 4 | 6 | 54 | 6.7580 | 0.6004 | 0.9455 | 1.2397 | 0.1245 | 0.0747 | 0.0449 | 0.1543 | 0.0927 |
| 11 | 11,200 | 2 | 2 | 10 | 55.8035 | 0.2993 | 0.9814 | 1.7224 | 0.0084 | 0.0025 | 0.0008 | 0.0145 | 0.0043 |
| 12 | 11,324 | 1 | 1 | 7 | 0.0044 | −0.0017 | 0.9925 | 2.1228 | 0.0006 | 0.0000 | 0.0000 | 0.0014 | 0.0000 |
| | | | SUM | | 117.8839 | | | | | | | | |
| | | | WTD ERR (%) | 21 | | | | SUM | 5.6771 | 10.9321 | 23.0346 | 0.0932 | −1.9544 |

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The content of each patent and scientific publication, and any other reference listed herein, is hereby incorporated by reference in its entirety to the extent that it contains relevant technical information.

What is claimed is:

1. A method for diagnosing an anxiety disorder in a subject, comprising:
   a. collecting a DNA sample from the subject;
   b. analyzing the DNA sample for the presence of a SNP in a PAC1 receptor gene and/or for epigenetic methylation at a first site within a ADCYAP1R1 CpG island;
   c. diagnosing the anxiety disorder in the subject having the SNP in the PAC1 receptor gene and/or having elevated levels of epigenetic methylation; and
   d. administering a therapeutically effective amount of a PACAP inhibitor or PACAP receptor antagonist.

2. The method of claim 1, wherein the anxiety disorder is PTSD.

3. The method of claim 1, wherein the gene encoding the PAC1 receptor is ADCYAP1R1.

4. The method of claim 3, wherein the SNP is located at position rs2267735 of the ADCYAP1R1 gene.

5. The method of claim 4, wherein the SNP is a G→C allelic mutation.

6. The method of claim 1, wherein the subject has been exposed to a trauma.

* * * * *